United States Patent
Caldwell et al.

[11] Patent Number: 6,140,349
[45] Date of Patent: Oct. 31, 2000

[54] CYCLIC AMINE MODULATORS OF CHEMOKINE RECEPTOR ACTIVITY

[75] Inventors: Charles G. Caldwell, Scotch Plains; Malcolm Maccoss, Freehold; Paul E. Finke, Milltown; Sander G. Mills, Scotch Plains; Bryan Oates, Wayne; Shankaran Kothandaraman, Kendall Park; Dooseop Kim, Westfield; Liping Wang, Plainsboro, all of N.J.

[73] Assignee: Merck & Co., Inc., Rahway, N.J.

[21] Appl. No.: 09/241,486

[22] Filed: Feb. 1, 1999

Related U.S. Application Data

[60] Provisional application No. 60/073,446, Feb. 2, 1998.

[51] Int. Cl.[7] ........................ A61K 31/445; C07D 409/10
[52] U.S. Cl. ........................ 514/326; 514/322; 514/329; 546/199; 546/210; 546/212; 546/213; 546/214; 546/224
[58] Field of Search ...................... 514/322, 326, 514/329; 546/199, 210, 212, 213, 214, 224

[56] References Cited

U.S. PATENT DOCUMENTS

| | | | |
|---|---|---|---|
| 4,452,803 | 6/1984 | Errland et al. | 514/326 |
| 4,556,714 | 12/1985 | Karrer | 546/190 |
| 5,082,847 | 1/1992 | Pascal et al. | 514/312 |
| 5,580,872 | 12/1996 | Chu et al. | 514/254 |

FOREIGN PATENT DOCUMENTS

| | | |
|---|---|---|
| 2145000 | 3/1995 | Canada . |
| 09249566 | 3/1996 | Japan . |
| WO 97/10211 | 3/1997 | WIPO . |
| WO 98/25604 | 6/1998 | WIPO . |
| WO 98/25605 | 6/1998 | WIPO . |
| WO 98/25617 | 6/1998 | WIPO . |

OTHER PUBLICATIONS

Chu et al. "Preparation of quinolizinone– and . . . " CA 126:117990, 1996.
Yao, et al., *Chem. Abstr.* vol. 127, No. 1, p. 606, 1997.
Hirschmann, *Books of Abst. 213th ACS National Meeting*, San Francisco, Apr. 13–17, 1997, Abs. No. 001.
Budhu, et al., U.S. application No. 09/141,227 (filed Aug. 27, 1998).

*Primary Examiner*—Ceila Chang
*Attorney, Agent, or Firm*—J. Eric Thies; David L. Rose

[57] ABSTRACT

The present invention is directed to cyclic amines of the formula I:

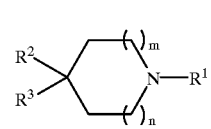

(wherein $R^1$, $R^2$, $R^3$, m and n are defined herein) which are useful as modulators of chemokine receptor activity. In particular, these compounds are useful as modulators of the chemokine receptors CCR-1, CCR-2, CCR-2A, CCR-2B, CCR-3, CCR-4, CCR-5, CXCR-3, and/or CXCR-4.

32 Claims, No Drawings

CYCLIC AMINE MODULATORS OF CHEMOKINE RECEPTOR ACTIVITY

This application claims priority benefits of Provisional Application No. 60/073,446, filed Feb. 2, 1998.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15,159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al.,*J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al.,*J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al.,*J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. Macrophage-tropic HIV and SIV envelope proteins have been shown to induce a signal through CCR-5 on CD4+ cells resulting in chemotaxis of T cells which may enhance the replication of the virus (Weissman, et al., *Nature*, 389, 981–985 (1997)). It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Similarly, an alteration in the CCR-2 gene, CCR2-64I, can prevent the onset of full-blown AIDS (Smith, et al., *Science*, 277,959–965 (1997). Absence of CCR-5 appears to confer protection from HIV-1 infection (*Nature*, 382, 668–669 (1996)). An inherited mutation in the gene for CCR5, Delta 32, has been shown to abolish functional expression of the gene and individuals homozygous for the mutation are apparently not susceptible to HIV infection. Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). The $\beta$-chemokine macrophage-derived chemokine (MDC) has been shown to inhibit HIV-1 infection (Pal, et al., *Science*, 278 (5338), 695–698 (1997). The chemokines RANTES, MIP-1α, MIP-1β, vMIP-I, vMIP-II, SDF-1 have also been shown to suppress HIV. A derivative of RANTES, (AOP)-RANTES, is a subnanomolar antagonist of CCR-5 function in monocytes (Simmons, et al., *Science*, 276, 276–279 (1997)). Monoclonal antibodies to CCR-5 have been reported to block infection of cells by HIV in vitro. Accordingly, an agent which could block chemokine receptors in humans who possess normal chemokine receptors should prevent infection in healthy individuals and slow or halt viral progression in infected patients (see *Science*, 275, 1261–1264 (1997)). By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β. PCT Patent Publication WO 97/10211 and EPO Patent Publication EP 0,673,928 disclose certain piperidines as tachykinin antagonists. PCT Patent Publications WO 97/24325 and WO 97/44329, and Japan Patent Publication JP 09,249,566 disclose certain compounds as chemokine antagonists.

SUMMARY OF THE INVENTION

The present invention is directed to compounds which are modulators of chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of formula I:

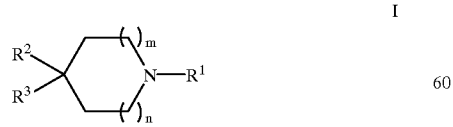

wherein:
$R^1$ is selected from a group consisting of:
linear or branched $C_{1-8}$ alkyl, linear or branched $C_{2-8}$ alkenyl, wherein the $C_{1-8}$ alkyl or $C_{2-8}$ alkenyl is optionally mono, di, tri or tetra substituted, where the substituents are independently selected from:
(a) hydroxy,
(b) oxo,
(c) cyano,
(d) halogen which is selected from F, Cl, Br, and I,
(e) trifluoromethyl,
(f) phenyl
(g) mono, di or tri-substituted phenyl, where the substituents are independently selected from:
(1') phenyl,
(2') hydroxy,
(3') $C_{1-6}$alkyl,
(4') cyano,
(5') halogen,
(6') trifluoromethyl,
(7') —NR$^6$COR$^7$,
(8') —NR$^6$CO$_2$R$^7$,
(9') —NR$^6$CONHR$^7$,
(10') —NR$^6$S(O)jR$^7$, wherein j is 1 or 2,
(11') —CONR$^6$R$^7$,
(12') —COR$^6$,
(13') —CO$_2$R$^6$,
(14') —OR$^6$,
(15') —S(O)$_k$R$^6$, wherein k is 0, 1 or 2,
(h) —NR$^6$R$^7$,
(i) —NR$^6$COR$^7$,
(j) —NR$^6$CO$_2$R$^7$,
(k) —NR$^6$CONHR$^7$,
(l) —NR$^6$S(O)j—R$^7$,
(m) —CONR$^6$R$^7$,
(n) —COR$^7$,
(o) —CO$_2$R$^7$,
(p) —OR$^7$,
(q) —S(O)$_k$R$^7$,
(r) —NR$^6$CO-heteroaryl,
(s) —NR$^6$S(O)j-heteroaryl, and
(t) heteroaryl, wherein heteroaryl is selected from the group consisting of:
(1') benzimidazolyl,
(2') benzofuranyl,
(3') benzoxazolyl,
(4') furanyl,
(5') imidazolyl,
(6') indolyl,
(7') isooxazolyl,
(8') isothiazolyl,
(9') oxadiazolyl,
(10') oxazolyl,
(11') pyrazinyl,
(12') pyrazolyl,
(13') pyridyl,
(14') pyrimidyl,
(15') pyrrolyl,
(16') quinolyl,
(17') tetrazolyl,
(18') thiadiazolyl,
(19') thiazolyl,
(20') thienyl, and
(21') triazolyl,
wherein the heteroaryl is unsubstituted or mono di or tri-substituted, where the substituents are independently selected from:
(a") phenyl,
(b") hydroxy,
(c") oxo,
(d") cyano, (e") halogen,
(f") $C_{1-6}$alkyl, and
(g") trifluoromethyl;

$R^2$ is selected from the group consisting of:
(1) hydrogen,
(2) hydroxy,
(3) $C_{1-6}$ alkyl,
(4) substituted $C_{1-6}$ alkyl, where the substituents are independently selected from:
  (a) phenyl,
  (b) hydroxy,
  (c) oxo,
  (d) halogen,
  (e) trifluoromethyl,
  (f) —$N(R^4)(R^5)$, wherein $R^4$ and $R^5$ are independently selected from hydrogen, $C_{1-6}$ alkyl, and $C_{1-6}$ alkyl substituted with $C_{5-8}$ cycloalkyl,
  (g) —$N(R^4)$—CO—O—$(R^5)$, and
  (h) —$N(R^{4'})$—CO—$N(R^4)(R^5)$, wherein $R^{4'}$ is selected from the definitions of $R^4$,
(5) —O—$C_{1-6}$ alkyl, and
(6) phenyl;

$R^3$ is selected from the group consisting of:
(1) —$N(R^8)$—CO—O—$(C_{1-6}$ alkyl)-Ar, and
(2) —$N(R^8)$—CO—O—$R^7$;

Ar is selected from the group consisting of:
(1) phenyl,
(2) pyridyl,
(3) pyrimidyl,
(4) naphthyl,
(5) furyl,
(6) pyrryl,
(7) thienyl,
(8) isothiazolyl,
(9) imidazolyl,
(10) benzimidazolyl,
(11) tetrazolyl,
(12) pyrazinyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) isoxazolyl,
(23) thiazolyl,
(24) oxazolyl,
(25) triazinyl, and
(26) benzthiazolyl,
(27) benzoxazolyl,
(28) imidazopyrazinyl,
(29) triazolopyrazinyl,
(30) naphthyridinyl,
(31) furopyridinyl,
(32) thiopyranopyrimidyl and the 5-oxide and 5-dioxide thereof,
(33) pyridazinyl,
(34) quinazolinyl,
(35) pteridinyl,
(36) triazolopyrimidyl,
(37) triazolopyrazinyl,
(38) thiapurinyl,
(39) oxapurinyl, and
(40) deazapurinyl, wherein Ar items (1) to (40) are unsubstituted or mono or di-substituted, where the substituents are independently selected from:
(a) $C_{1-6}$ alkyl, unsubstituted or substituted with a substituent selected from:
  (1') oxo,
  (2') hydroxy,
  (3') —$OR^7$,
  (4') phenyl,
  (5') trifluoromethyl, and
  (6') phenyl or mono, di or tri-substituted phenyl, where the substituents are independently selected from: hydroxy, cyano, halogen, and trifluoromethyl,
(b) halogen,
(c) —$OC_{1-6}$ alkyl,
(d) trifluoromethyl,
(e) hydroxy,
(f) —$NO_2$,
(g) —$(CH_2)_pS(O)_k$—$(C_{1-6}$ alkyl), wherein p is 0, 1 or 2,
(h) —$(CH_2)_pS(O)j$—$NH_2$,
(i) —$(CH_2)_pS(O)j$—$NH(C_{1-6}$ alkyl),
(J) —$(CH_2)_pS(O)j$—$NHR^6$,
(k) —$(CH_2)_pS(O)j$—$NR^6$—$(C_{1-6}$ alkyl),
(l) —$(CH_2)_pCONH_2$,
(m) —$(CH_2)_pCONH$—$(C_{1-6}$ alkyl),
(n) —$(CH_2)_pCONHR^6$,
(o) —$(CH_2)_pCONR^6$—$(C_{1-6}$ alkyl),
(p) —$(CH_2)_pCO_2H$,
(q) —$(CH_2)_pCO_2$—$(C_{1-6}$ alkyl),
(r) —$(CH_2)_pNR^6R^7$,
(s) —$(CH_2)_pNH$—$C(O)$—$C_{1-6}$alkyl,
(t) —$(CH_2)_pNH$—$C(O)$—$NH_2$,
(u) —$(CH_2)_pNH$—$C(O)$—$NHC_{1-6}$alkyl,
(v) —$(CH_2)_pNH$—$C(O)$—$N(C_{1-6}$ alkyl$)_2$,
(w) —$(CH_2)_pNH$—$S(O)_k$—$C_{1-6}$alkyl,
(x) —$(CH_2)_pN(C_{1-3}$alkyl)—$C(O)$—$N(diC_{1-6}$ alkyl),
(y) —$(CH_2)_p$—heteroaryl, —$C(O)$-heteroaryl or —$(CH_2)_p$—O-heteroaryl, wherein the heteroaryl is selected from the group consisting of:
  (1') benzimidazolyl,
  (2') benzofuranyl,
  (3') benzothiophenyl,
  (4') benzoxazolyl,
  (5') furanyl,
  (6') imidazolyl,
  (7') indolyl,
  (8') isooxazolyl,
  (9') isothiazolyl,
  (10') oxadiazolyl,
  (11') oxazolyl,
  (12') pyrazinyl,
  (13') pyrazolyl,
  (14') pyridyl,
  (15') pyrimidyl,
  (16') pyrrolyl,
  (17') quinolyl,
  (18') tetrazolyl,
  (19') thiadiazolyl,
  (20') thiazolyl,
  (21') thienyl,
  (22') triazolyl,
  (23') dihydrobenzimidazolyl, (24') dihydrobenzofuranyl,
(25') dihydrobenzothiophenyl,
(26') dihydrobenzoxazolyl,
(27') dihydrofuranyl
(28') dihydroimidazolyl,
(29') dihydroindolyl,
(30') dihydroisooxazolyl,
(31') dihydroisothiazolyl,
(32') dihydrooxadiazolyl,
(33') dihydropyrazinyl,
(34') dihydropyrazolyl,
(35') dihydropyridinyl,
(36') dihydropyrimidinyl,
(37') dihydroquinolinyl,
wherein the heteroaryl group of items (1') to (37') is unsubstituted, or mono, di or tri-substituted, where the substituents are selected from:
(a') hydrogen,
(b') $C_{1-6}$ alkyl, branched or unbranched, unsubstituted or mono or di-substituted, where the substituents are selected from:
hydrogen and hydroxy,
(c') hydroxy,
(d') oxo,
(e') —$OR^6$,
(f') halogen,
(g') trifluoromethyl,
(h') nitro,
(i') cyano,
(j') —$NHR^6$,
(k') —$NR^6R^7$,
(l') —$NHCOR^6$,
(m') —$NR^6COR^7$,
(n') —$NHCO_2R^6$,
(o') —$NR^6CO_2R^7$,
(p') —$NHS(O)jR^6$,
(q') —$NR_6S(O)jR^7$,
(r') —$CONR^6R^7$,
(s') —$COR^6$,
(t') —$CO_2R^6$, and
(u') —$S(O)jR^6$;
$R^6$ is selected from the group consisting of:
(1) hydrogen,
(2) $C_{1-6}$ alkyl,
(3) substituted $C_{1-6}$ alkyl, where the substituents are independently selected from:
(a) phenyl,
(b) hydroxy,
(c) oxo,
(d) cyano,
(e) halogen,
(f) trifluoromethyl, and
(g) $C_{5-8}$ cycloalkyl,
(4) phenyl,
(5) mono, di or tri-substituted phenyl, where the substituents are independently selected from:
(a) hydroxy,
(b) $C_{1-6}$alkyl,
(c) cyano,
(d) halogen, and
(e) trifluoromethyl;
$R^7$ is selected from the group consisting of:
(1) hydrogen,
(2) $C_{1-6}$ alkyl or $C_{5-8}$ cycloalkyl,
(3) substituted $C_{1-6}$ alkyl or $C_{5-8}$ cycloalkyl, where the substituents are independently selected from:
(a) phenyl,
(b) mono, di or tri-substituted phenyl, where the substituent is independently selected from:
(1') hydroxy,
(2') $C_{1-3}$alkyl,
(3') cyano,
(4') halogen,
(5') trifluoromethyl, and
(6') $C_{1-3}$alkyloxy,
(c) hydroxy,
(d) oxo,
(e) cyano,
(f) halogen, and
(g) trifluoromethyl,
(4) phenyl,
(5) mono, di or tri-substituted phenyl, where the substituents are independently selected from:
(a) hydroxy,
(b) $C_{1-6}$alkyl,
(c) $C_{1-6}$alkoxy
(d) cyano,
(e) halogen, and
(f) trifluoromethyl;
or $R^6$ and $R^7$ may be joined together to form a 5-, 6-, or 7-membered monocyclic saturated ring containing 1 or 2 heteroatoms independently selected from nitrogen, oxygen, and sulfur, and in which the ring is unsubstituted or mono or di-substituted, the substituents independently selected from:
(1) hydroxy,
(2) oxo,
(3) cyano,
(4) halogen,
(5) trifluoromethyl,
$R^8$ is selected from the group consisting of:
(1) $C_{2-10}$ alkenyl,
(2) $C_{1-10}$ alkynyl,
(3) heteroaryl,
(3) substituted $C_{1-10}$ alkyl, $C_{1-10}$ alkenyl or $C_{2-10}$ alkynyl, where the substituents are independently selected from:
(a) $C_{3-4}$ cycloalkyl,
(b) hydroxy,
(c) $C_{1-6}$ alkyloxy,
(d) cyano,
(e) heteroaryl,
(f) halogen,
(g) trifluoromethyl,
(h) —$CO_2H$,
(i) —$SO_3H$,
(j) —$CO_2R^6$,
(k) —$CONR^6R^7$,
(l) —$NR^4CONR^6R^7$,
(m) —$NR^4CO_2R^6$,
(n) —$NR^4COR^6$, and
(o) —$SR^4$;
m is an integer selected from 0, 1 and 2,
n is an integer selected from 0, 1 and 2,
and pharmaceutically acceptable salts thereof.

Preferred compounds of the present invention include those of formula Ia:

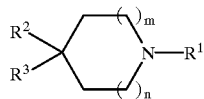

Ia wherein:

R¹ is selected from a group consisting of:
C₃, C₄, C₅, C₆, C₇, or C₈ linear or branched alkyl, which is unsubstituted or mono, di or tri-substituted, where the substituents are independently selected from:
(a) hydroxy,
(b) Cl or F,
(c) phenyl,
(d) mono, di or tri-substituted phenyl, where the substituents are independently selected from:
(1') phenyl,
(2') hydroxy,
(3') $C_{1-6}$alkyl,
(4') cyano,
(5') halogen, and
(6') trifluoromethyl,
(e) —NR⁶CO—R⁷, wherein R⁶ is hydrogen or $C_{1-6}$ alkyl, unsubstituted or substituted with $C_{5-8}$ cycloalkyl, and R⁷ is $C_{1-6}$ alkyl, benzyl or phenyl which is unsubstituted or substituted with halo, $CF_3$, $C_{1-6}$alkyl, or $C_{1-3}$alkoxy,
(f) —COR⁷,
(g) —OR⁷,
(h) —NR⁶S(O)j-R⁷, where j is 1 or 2,
(i) —NR⁶S(O)j-heteroaryl, wherein heteroaryl is selected from the group consisting of:
(1') benzimidazolyl,
(2') benzofuranyl,
(3') benzothiophenyl,
(4') benzoxazolyl,
(5') furanyl,
(6') imidazolyl,
(7') indolyl,
(8') isooxazolyl,
(9') isothiazolyl,
(10') oxadiazolyl,
(11') oxazolyl,
(12') pyrazinyl,
(13') pyrazolyl,
(14') pyridyl,
(15') pyrimidyl,
(16') pyrrolyl,
(17') quinolyl,
(18') tetrazolyl,
(19') thiadiazolyl,
(20') thiazolyl,
(21') thienyl,
(22') triazolyl,
(23') dihydrobenzimidazolyl,
(24') dihydrobenzofuranyl,
(25') dihydrobenzothiophenyl,
(26') dihydrobenzoxazolyl,
(27') dihydrofuranyl
(28') dihydroimidazolyl,
(29') dihydroindolyl,
(30') dihydroisooxazolyl,
(31') dihydroisothiazolyl,
(32') dihydrooxadiazolyl,
(33') dihydropyrazinyl,
(34') dihydropyrazolyl,
(35') dihydropyridinyl,
(36') dihydropyrimidinyl,
(37') dihydroquinolinyl,
wherein the heteroaryl is unsubstituted or mono di or tri-substituted, where the substituents are independently selected from:
(a') phenyl,
(b') hydroxy,
(c') oxo,
(d') cyano,
(e') halogen,
(f') $C_{1-6}$alkyl, and
(g') trifluoromethyl;

R² is selected from the group consisting of:
(1) hydrogen,
(2) hydroxy,
(3) $C_{1-6}$ alkyl,
(4) —O—$C_{1-6}$ alkyl,
(5) phenyl,
(6) —N(CH₃)—CO—N(H)(CH₃),
(7) —N(H)—CO—O—CH₃, and
(8) —CO—CH₃;

R³ is selected from the group consisting of:
(1) —N(R⁸)—CO—O—($C_{1-6}$ alkyl)-Ar, and
(2) —N(R⁸)—CO—O—R⁷;

Ar is selected from the group consisting of:
(1) phenyl,
(2) pyrazinyl,
(3) pyrazolyl,
(4) pyridyl,
(5) pyrimidyl, and
(6) thienyl,
wherein the Ar is unsubstituted or mono or di-substituted, and the substituents are independently selected from:
(a) $C_{1-6}$ alkyl, unsubstituted or substituted with
(1') oxo,
(2') hydroxy,
(3') —OR⁷,
(4') phenyl, and
(5') trifluoromethyl,
(b) halogen,
(c) —$OC_{1-6}$ alkyl,
(d) trifluoromethyl,
(e) —NO₂,
(f) CONR⁶—($C_{1-2}$ alkyl),
(g) CO₂H,
(h) CO₂—($C_{1-2}$ alkyl),
(i) CH₂NR⁶—($C_{1-2}$ alkyl),
(j) CH₂NH—C(O)—$C_{1-3}$alkyl,
(k) CH₂NH—C(O)NH₂,
(l) CH₂NH—C(O)NH$C_{1-3}$alkyl,
(m) CH₂NH—C(O)N-di$C_{1-3}$ alkyl),
(n) CH₂NH—S(O)j-$C_{1-3}$alkyl,
(o) CH₂-heteroaryl, with the heteroaryl is selected from the group consisting of:
(1') imidazolyl,
(2') oxazolyl,
(3') pyridyl,
(4') tetrazolyl,
(5') triazolyl,
and the heteroaryl is unsubstituted, mono, di or tri-substituted, where the substituents selected from:
(a') hydrogen,
(b') $C_{1-6}$ alkyl, branched or unbranched, unsubstituted or mono or di-substituted, the substituents being selected from hydrogen and hydroxy;

$R^8$ is selected from the group consisting of:
(1) $C_{2-10}$ alkenyl,
(2) $C_{2-10}$ alkynyl,
(3) heteroaryl,
(4) substituted $C_{1-10}$ alkyl, $C_{1-10}$ alkenyl or $C_{2-10}$ alkynyl, where the substituents are independently selected from:
  (a) $C_{3-4}$ cycloalkyl,
  (b) hydroxy,
  (c) $C_{1-6}$ alkyloxy,
  (d) cyano,
  (e) heteroaryl,
  (f) halogen,
  (g) trifluoromethyl,
  (h) —$CO_2H$,
  (i) —$SO_3H$,
  (j) —$CO_2R^6$,
  (k) —$CONR^6R^7$,
  (l) —$NR^4CONR^6R^7$,
  (m) —$NR^4CO_2R^6$,
  (n) —$NR^4COR^6$, and
  (o) —$SR^4$;

m is an integer selected from 0, 1 and 2,
n is an integer selected from 0, 1 and 2, with the proviso that the sum of m+n is 2;
and pharmaceutically acceptable salts thereof.

More preferred compounds of the present invention include those of formula Ib:

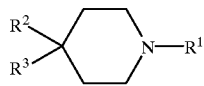

Ib wherein:
$R^1$, $R^2$ and $R^3$ are as defined herein;
and pharmaceutically acceptable salts thereof.

In the present invention it is preferred that
$R^1$ is selected from the group consisting of:
$C_3$, $C_4$, $C_5$, $C_6$, $C_7$, or $C_8$ linear or branched alkyl, which is unsubstituted or mono, di or tri-substituted, where the substituents are independently selected from:
(a) hydroxy,
(b) Cl or F,
(c) phenyl,
(d) mono, di or tri-substituted phenyl, where the substituents are independently selected from:
  (1') phenyl,
  (2') hydroxy,
  (3') $C_{1-6}$alkyl,
  (4') cyano,
  (5') halogen, and
  (6') trifluoromethyl,
(e) —$NR^6CO$—$R^7$, wherein $R^6$ is hydrogen or $C_{1-6}$ alkyl, unsubstituted or substituted with $C_{5-8}$ cycloalkyl, and $R^7$ is $C_{1-6}$ alkyl, benzyl or phenyl which is unsubstituted or substituted with halo, $CF_3$, $C_{1-6}$alkyl, or $C_{1-3}$alkoxy,
(f) —$COR^7$,
(g) —$OR^7$,
(h) —$NR^6S(O)j$-$R^7$, where j is 1 or 2,
(i) —$NR^6S(O)j$-heteroaryl, wherein heteroaryl is selected from the group consisting of:
  (1') benzimidazolyl,
  (2') benzofuranyl,
  (3') benzoxazolyl,
  (4') furanyl,
  (5') imidazolyl,
  (6') indolyl,
  (7') isooxazolyl,
  (8') isothiazolyl,
  (9') oxadiazolyl,
  (10') oxazolyl,
  (11') pyrazinyl,
  (12') pyrazolyl,
  (13') pyridyl,
  (14') pyrimidyl,
  (15') pyrrolyl,
  (16') quinolyl,
  (17') tetrazolyl,
  (18') thiadiazolyl,
  (19') thiazolyl,
  (20') thienyl, and
  (21') triazolyl,
wherein the heteroaryl is unsubstituted or mono di or tri-substituted, where the substituents are independently selected from:
  (a') phenyl,
  (b') hydroxy,
  (c') oxo,
  (d') cyano,
  (e') halogen,
  (f') $C_{1-6}$alkyl, and
  (g') trifluoromethyl.

In the present invention it is preferred that
$R^1$ bears at least one substituent which is selected from:
(a) —$NR^6CO$—$R^7$, wherein $R^6$ is $C_{1-6}$ alkyl, unsubstituted or substituted with cyclohexyl, and $R^7$ is $C_{1-6}$ alkyl, benzyl or phenyl which is unsubstituted or substituted with halo, $CF_3$, $C_{1-3}$alkyl, or $C_{1-3}$alkoxy, and
(b) —$NR^6S(O)j$-$R^7$, where j is 1 or 2.

In the present invention it is more preferred that
$R^1$ is selected from the group consisting of:
$C_4$, $C_5$, $C_6$, $C_7$ or $C_8$ linear or branched alkyl, which is mono, di- or tri-substituted, where the substituents are independently selected from:
(a) hydroxy,
(b) Cl or F,
(c) phenyl,
(d) mono, di or tri-substituted phenyl, where the substituents are independently selected from:
  (1') hydroxy,
  (2') methyl or ethyl,
  (3') Cl or F, and
  (4') trifluoromethyl,
(e) —$NR^6CO$—$R^7$, wherein $R^6$ is $C_{1-3}$ alkyl, unsubstituted or substituted with cyclohexyl, and $R^7$ is $C_{1-6}$ alkyl, benzyl or phenyl which is unsubstituted or substituted with halo, $CF_3$, $C_{1-3}$alkyl, or $C_{1-3}$alkoxy,
(f) —$NR^6S(O)j$-$R^7$, where j is 1 or 2.

In the present invention it is still more preferred that
$R^1$ is selected from the group consisting of:
$C_4$, $C_5$, or $C_6$ linear alkyl, which is substituted, where the substituents are independently selected from:
(a) phenyl,
(b) mono, di or tri-substituted phenyl, where the substituents are independently selected from:
  (1') hydroxy,
  (2') methyl or ethyl,
  (3') Cl or F, and
  (4') trifluoromethyl, (c) $C_{1-6}$ alkyl,
(d) —NR$^6$CO—R$^7$, wherein R$^6$ is methyl, unsubstituted or substituted with cyclohexyl, and R$^7$ is phenyl which is unsubstituted or substituted with Cl, F, CF$_3$, $C_{1-3}$alkyl or $C_{1-3}$alkoxy, and
(e) —NR$^6$S(O)j-R$^7$, where j is 1 or 2.

In the present invention it is still more preferred that R$^1$ is $C_4$ linear alkyl, which is substituted, where the substituents are independently selected from:
(a) phenyl,
(b) mono, di or tri-substituted phenyl, where the substituents are independently selected from:
(1') hydroxy,
(2') methyl or ethyl,
(3') Cl or F, and
(4') trifluoromethyl,
(c) $C_{1-6}$ alkyl, and
(d) —NR$^6$S(O)j-R$^7$, where R$^6$ is methyl, unsubstituted or substituted with cyclohexyl, and R$^7$ is phenyl which is unsubstituted or substituted with Cl, F, CF$_3$, $C_{1-3}$alkyl or $C_{1-3}$alkoxy, and j is 1 or 2.

In the present invention it is even more preferred that R$^1$ is:

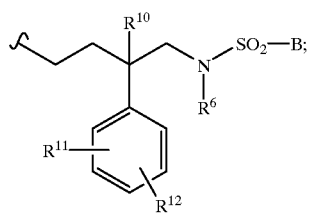

wherein:
B is selected from the group consisting of:
(a) phenyl, and
(b) di or tri-substituted phenyl, wherein the substituents on phenyl are independently selected from: chloro, methyl, phenyl, $C_{1-3}$alkoxy, and CF$_3$;
R$^6$ is $C_{1-3}$ alkyl, unsubstituted or substituted with cyclohexyl;
R$^{10}$ is selected from the group consisting of:
(1) hydrogen, and
(2) $C_{1-6}$ alkyl;
R$^{11}$ and R$^{12}$ are independently selected from the group consisting of:
(1) hydrogen,
(2) hydroxy,
(3) methyl or ethyl,
(4) Cl or F, and
(5) trifluoromethyl.

In the present invention it is most preferred that R$^1$ is selected from the group consisting of:

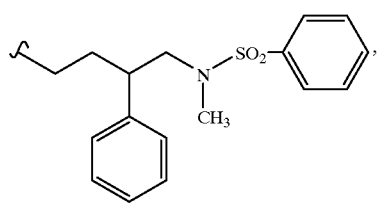

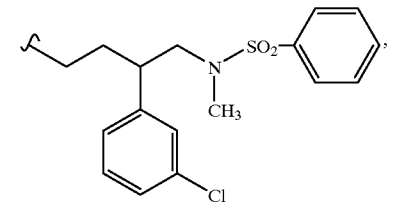

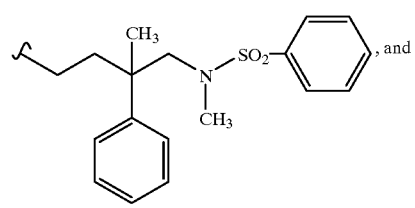

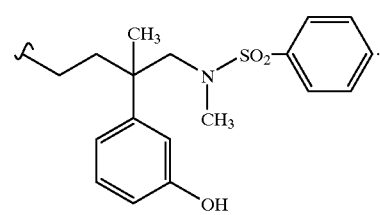

In the present invention it is most preferred that R$^1$ is selected from the group consisting of:

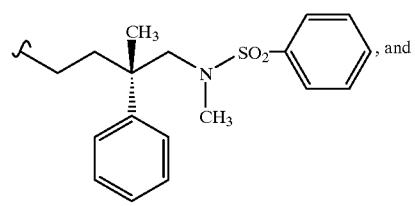

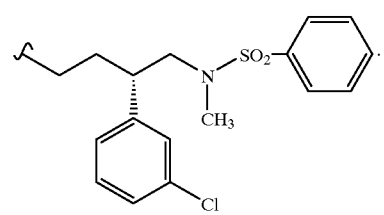

In the present invention it is preferred that R$^2$ is selected from the group consisting of:
(1) hydrogen,
(2) hydroxy,
(3) $C_{1-6}$ alkyl,
(4) —O—$C_{1-6}$ alkyl, and
(5) phenyl.

In the present invention it is more preferred that R$^2$ is selected from the group consisting of:
(1) hydrogen,
(2) hydroxy, and
(3) phenyl.

In the present invention it is most preferred that R$^2$ is hydrogen.

In the present invention it is preferred that Ar is selected from the group consisting of:
(1) phenyl,
(2) pyrazinyl,
(3) pyrazolyl,
(4) pyridyl, (5) pyrimidyl, and
(6) thienyl,
wherein the Ar is unsubstituted or mono or di-substituted, and substituents are independently selected from:
(a) $C_{1-3}$ alkyl, unsubstituted or substituted with
(1') oxo,
(2') hydroxy,
(3') —$OR^7$,
(4') phenyl, and
(5') trifluoromethyl,
(b) —$NO_2$,
(c) —$CONH_2$,
(d) —$CONR^6$—($C_{1-2}$ alkyl),
(e) —$CO_2H$,
(f) —$CO_2$—($C_{1-2}$ alkyl),
(g) —$CH_2NR^6$—($C_{1-2}$ alkyl),
(h) —$CH_2NH$—$C(O)$—$C_{1-3}$alkyl,
(i) —$CH_2NH$—$C(O)NH_2$,
(j) —$CH_2NH$—$C(O)NHC_{1-3}$alkyl,
(k) —$CH_2NH$—$C(O)N$-$diC_{1-3}$ alkyl),
(l) —$CH_2NH$—$S(O)j$-$C_{1-3}$alkyl,
(m) —$CH_2$-heteroaryl, with the heteroaryl is selected from the group consisting of:
(1') imidazolyl,
(2') oxazolyl,
(3') pyridyl,
(4') tetrazolyl,
(5') triazolyl, and the heteroaryl is unsubstituted, mono, di or tri-substituted, where the substituents selected from:
(a') hydrogen,
(b') $C_{1-6}$ alkyl, branched or unbranched, unsubstituted or mono or di-substituted, the substituents being selected from hydrogen and hydroxy.

In the present invention it is more preferred that
Ar is selected from:
phenyl, mono substituted phenyl or di-substituted phenyl, wherein the substituents are selected from the group consisting of:
(a) $C_{1-3}$ alkyl, unsubstituted or substituted with
(1') oxo,
(2') hydroxy, or
(3') —$OR^6$, wherein $R^6$ is hydrogen or $C_{1-3}$ alkyl,
(b) —$NO_2$,
(c) —$CONH_2$,
(d) —$CO_2H$,
(e) —$CH_2NR^6$—($C_{1-2}$ alkyl),
(f) —$CH_2NH$—$C(O)$—$C_{1-3}$alkyl,
(g) —$CH_2NH$—$C(O)NH_2$,
(h) —$CH_2NH$—$C(O)NHC_{1-3}$alkyl,
(i) —$CH_2NH$—$C(O)N$-$diC_{1-3}$ alkyl),
(j) —$CH_2NH$—$S(O)j$-$C_{1-3}$alkyl, and
(k) —$CH_2$-heteroaryl, where heteroaryl is selected from the group consisting of:
(1') imidazolyl,
(2') oxazolyl,
(3') pyridyl,
(4') tetrazolyl,
(5') triazolyl, and where heteroaryl is unsubstituted, mono, di or tri substituted, where the substituents are independently selected from:
(a') hydrogen,
(b') $C_{1-6}$ alkyl, branched or unbranched, unsubstituted or mono or disubstituted, where the substituents are selected from: hydrogen and hydroxy.

In the present invention it is even more preferred that
Ar is selected from:
phenyl, or mono substituted phenyl wherein the substituent is selected from: —$NO_2$, —$CONH_2$, and —$CO_2H$.

In the present invention it is even more preferred that
Ar is selected from:
phenyl, or para-$NO_2$ phenyl.

In the present invention it is preferred that
$R^3$ is:
—$N(R^8)$—$CO$—$O$—($C_{1-6}$ alkyl)-Ar.

In the present invention it is more preferred that
$R^3$ is:
—$N(R^8)$—$CO$—$O$—$(CH_2)$-Ar.

In the present invention it is still more preferred that
$R^3$ is selected from:
(1) —$N(R^8)$—$CO$—$O$—$(CH_2)$-phenyl,
(2) —$N(R^8)$—$CO$—$O$—$(CH_2)$-(phenyl-$NO_2$),
(3) —$N(R^8)$—$CO$—$O$—$(CH_2)$-(phenyl-$CONH_2$), and
(4) —$N(R^8)$—$CO$—$O$—$(CH_2)$-(phenyl-$CO_2H$).

In the present invention it is preferred that
$R^8$ is selected from the group consisting of:
(1) $C_{2-10}$ alkenyl,
(2) $C_{2-10}$ alkynyl,
(3) heteroaryl,
(4) substituted $C_{1-10}$ alkyl, $C_{2-10}$ alkenyl or $C_{1-10}$ alkynyl, where the substituents are independently selected from:
(a) $C_{3-4}$ cycloalkyl,
(b) hydroxy,
(c) $C_{1-6}$ alkyloxy,
(d) cyano,
(e) heteroaryl,
(f) halogen,
(g) —$CO_2H$,
(h) —$CO_2R^6$, and
(i) —$CONR^6R^7$.

In the present invention it is more preferred that
$R^8$ is selected from the group consisting of:
(1) $C_{2-10}$ alkenyl,
(2) $C_{2-10}$ alkynyl,
(3) substituted $C_{1-10}$ alkyl, $C_{1-10}$ alkenyl or $C_{2-10}$ alkynyl, where the substituents are independently selected from:
(a) $C_{3-4}$ cycloalkyl,
(b) hydroxy,
(c) $C_{1-6}$ alkyloxy,
(d) cyano,
(e) tetrazolyl,
(f) fluoro,
(g) —$CO_2H$,
(h) —$CO_2R^6$, and
(i) —$CONR^6R^7$.

In the present invention it is even more preferred that $R^8$ is selected from the group consisting of:
(1) $C_{3-5}$ alkenyl,
(2) $C_{3-4}$ alkynyl,
(3) substituted $C_{1-4}$ alkyl, where the substituents are independently selected from:
(a) cyclopropyl,
(b) cyclobutyl,
(c) cyano,
(d) fluoro,
(e) —$CO_2CH_3$,
(f) —$CONH_2$,
(g) $C_{1-2}$ alkyloxy, and
(h) hydroxy.

In the present invention it is still more preferred that $R^8$ is selected from the group consisting of:
(1) —$CH_2$—$CH$=$CH_2$,
(2) —$(CH_2)_2$—$CH$=$CH_2$,
(3) —$(CH_2)_3$—$CH$=$CH_2$,
(4) —$CH_2$—$C$≡$CH$,
(5) —$CH_2$—$C$≡$N$,
(6) —$CH_2$-cyclopropyl,
(7) —$CH_2$-cyclobutyl,
(8) —$(CH_2)_2$—$F$,
(9) —$CH_2$—$CO_2$—$CH_3$,
(10) —$CH_2$—$CO$—$NH_2$,
(11) —$(CH_2)_2$—$OCH_3$,
(12) —$(CH_2)_2$—$OH$,
(13) —$(CH_2)_3$—$OH$, and
(14) —$CH_2$—$CH(OH)$—$CH_2$—$OH$.

In the present invention it is preferred that
m is an integer selected from 0, 1 and 2,
n is an integer selected from 0, 1 and 2, with the proviso that the sum of m+n is 2.

In the present invention it is more preferred that m is 1, and n is 1.

As appreciated by those of skill in the art, halo as used herein are intended to include chloro, fluoro, bromo and iodo. Similarly, $C_{1-6}$, as in $C_{1-6}$alkyl is defined to identify the group as having 1, 2, 3, 4, 5, or 6 carbons, such that $C_{1-6}$alkyl specifically includes methyl, ethyl, propyl, butyl, pentyl, hexyl, and cyclohexyl.

Exemplifying the invention is the use of the compounds disclosed in the Examples and herein.

Preferred compounds of the present invention include the compounds of the formula:

wherein:

| $R_a$ | $R_b$ |
|---|---|
| —$CH_2$—$CH$=$CH_2$ | hydrogen |
| —$(CH_2)_2$—$CH$=$CH_2$ | hydrogen |
| —$(CH_2)_3$—$CH$=$CH_2$ | hydrogen |
| —$CH_2$—$C$≡$CH$ | hydrogen |
| —$CH_2$—$C$≡$N$ | hydrogen |
| —$CH_2$-cyclopropyl | hydrogen |
| —$CH_2$-cyclobutyl | hydrogen |
| —$(CH_2)_2$—$F$ | hydrogen |
| —$CH_2$—$CO_2$—$CH_3$ | hydrogen |
| —$CH_2$—$CO_2$—$NH_2$ | hydrogen |
| —$(CH_2)_2$—$OCH_3$ | hydrogen |
| —$(CH_2)_2$—$OH$ | hydrogen |
| —$(CH_2)_3$—$OH$ | hydrogen |
| —$CH_2$—$CH(OH)$—$CH_2$—$OH$ | hydrogen |
| —$CH_2$—$CH$=$CH_2$ | —$NO_2$ |
| —$(CH_2)_2$—$CH$=$CH_2$ | —$NO_2$ |
| —$(CH_2)_3$—$CH$=$CH_2$ | —$NO_2$ |
| —$CH_2$—$C$≡$CH$ | —$NO_2$ |
| —$CH_2$—$C$≡$N$ | —$NO_2$ |
| —$CH_2$-cyclopropyl | —$NO_2$ |
| —$CH_2$-cyclobutyl | —$NO_2$ |
| —$(CH_2)_2$—$F$ | —$NO_2$ |
| —$CH_2$—$CO_2$—$CH_3$ | —$NO_2$ |
| —$CH_2$—$CO_2$—$NH_2$ | —$NO_2$ |
| —$(CH_2)_2$—$OCH_3$ | —$NO_2$ |
| —$(CH_2)_2$—$OH$ | —$NO_2$ |
| —$(CH_2)_3$—$OH$ | —$NO_2$ |
| —$CH_2$—$CH(OH)$—$CH_2$—$OH$ | —$NO_2$ | and pharmaceutically acceptable salts thereof.

Specific compounds within the present invention include a compound which selected from the group consisting of:

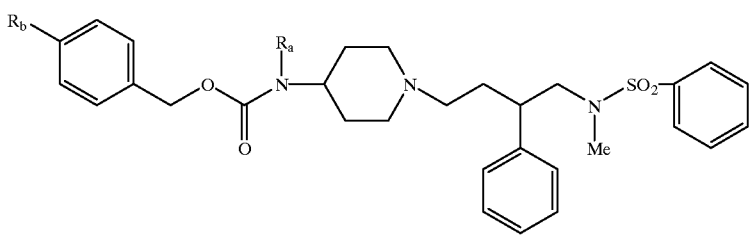

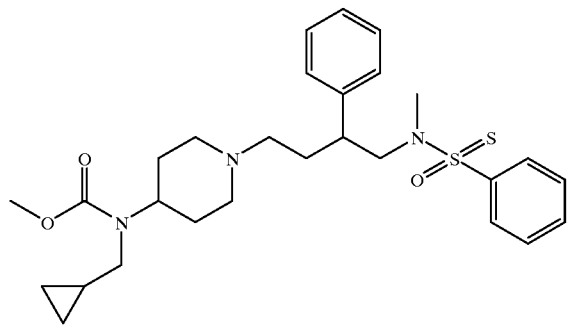
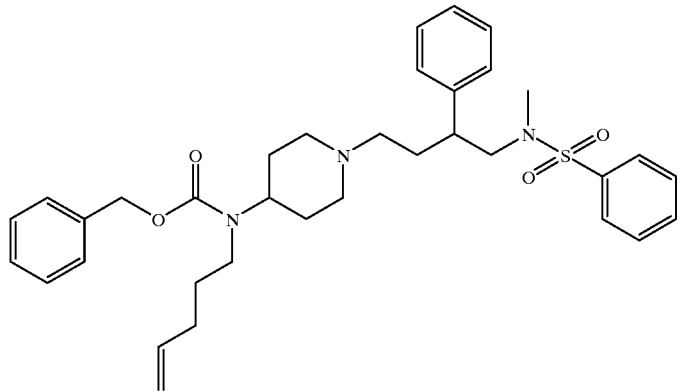
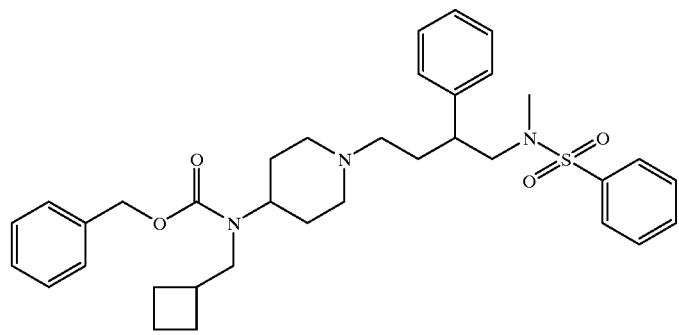
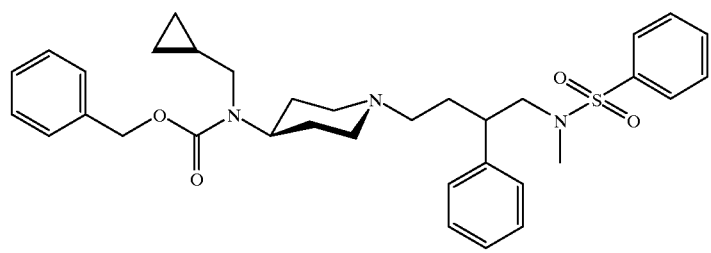
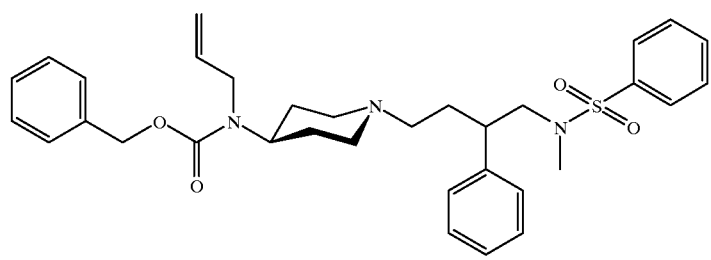

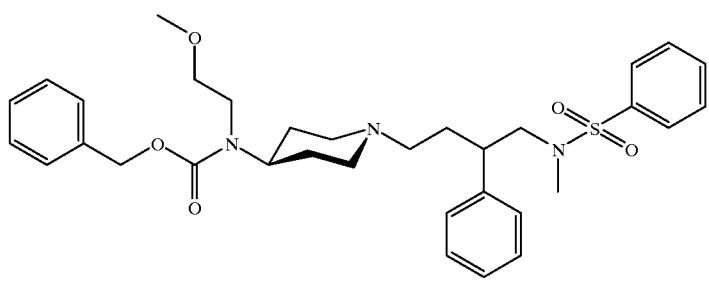
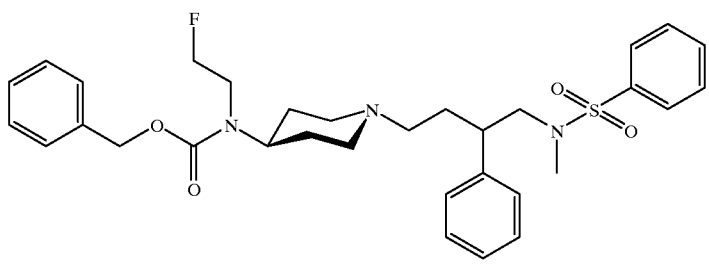
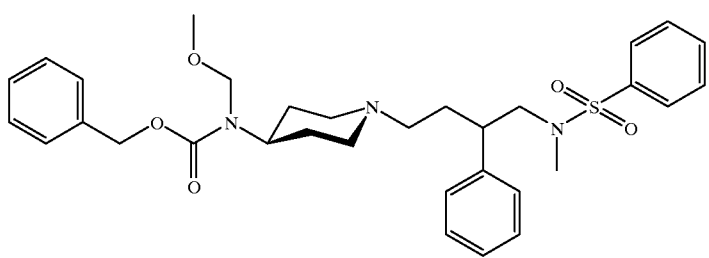
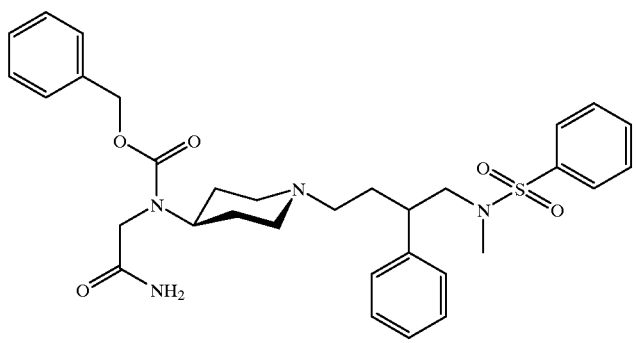
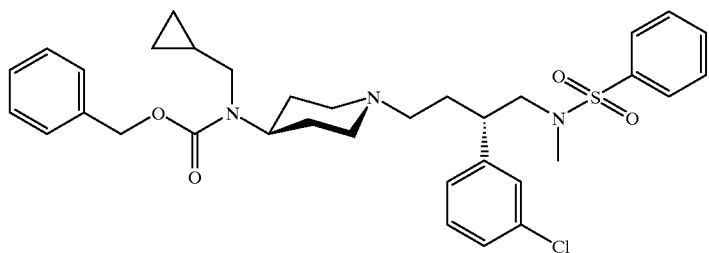

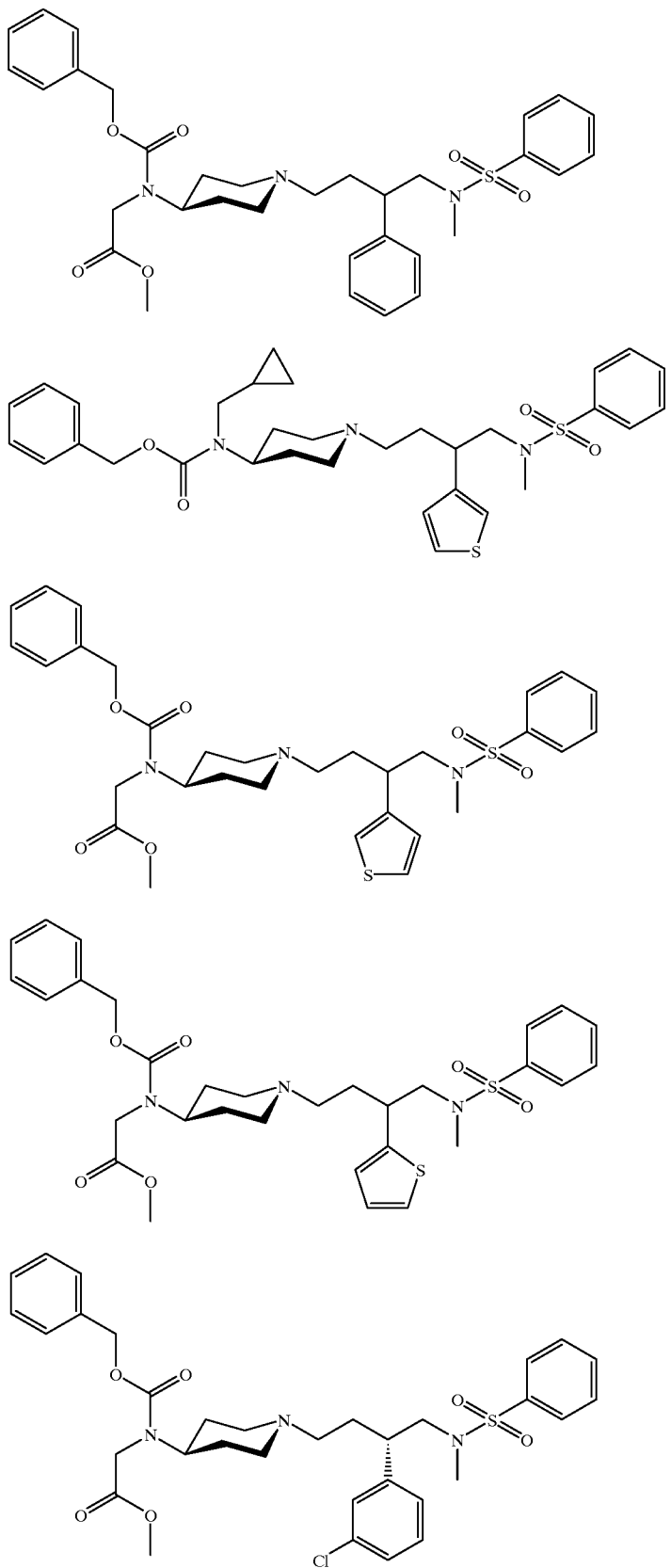

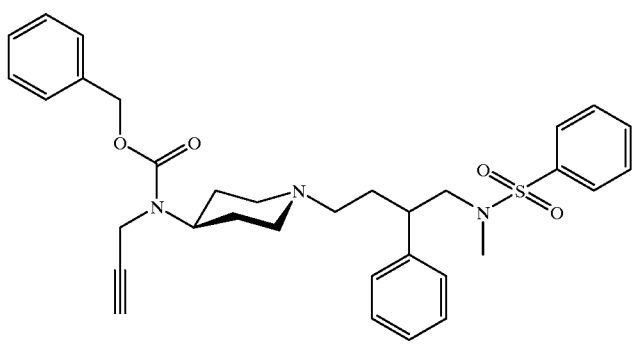
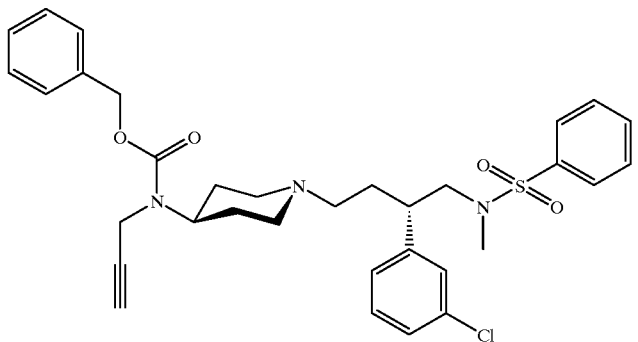
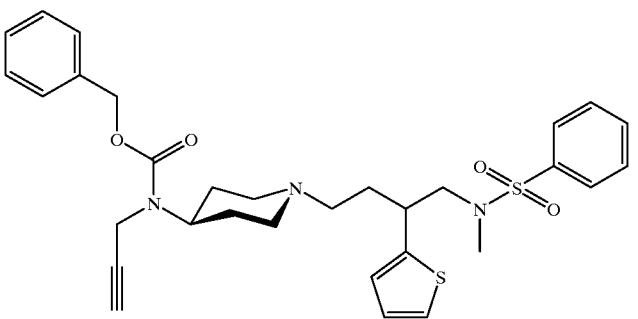
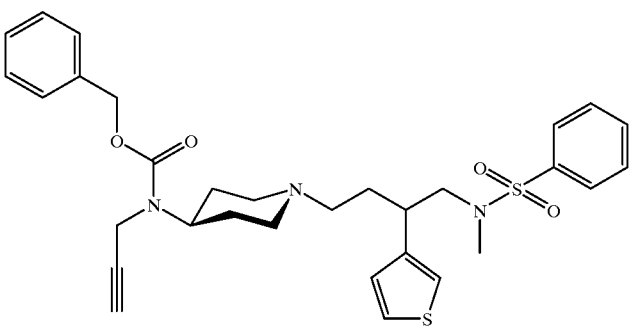
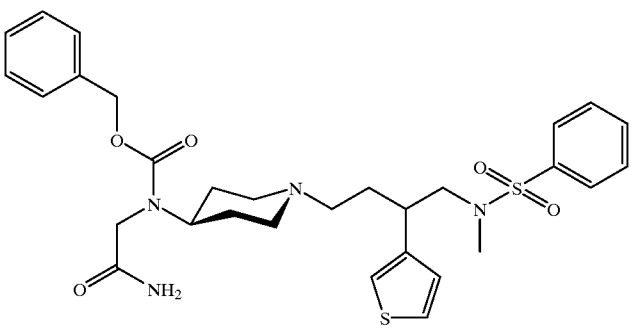

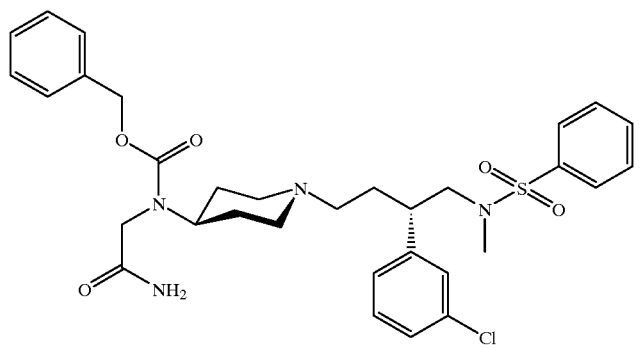
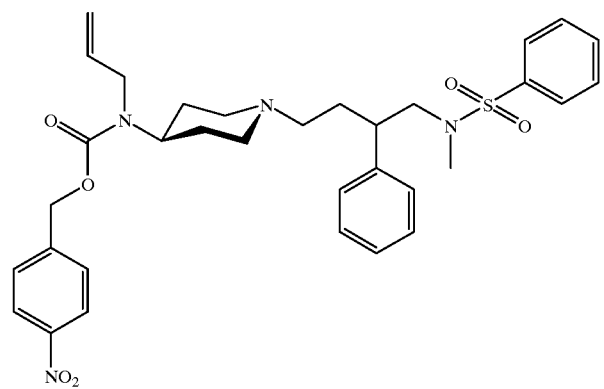
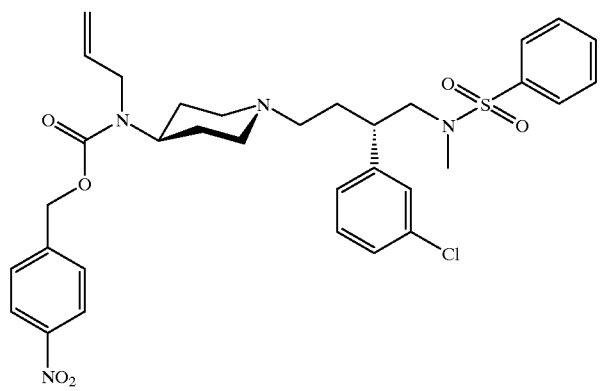
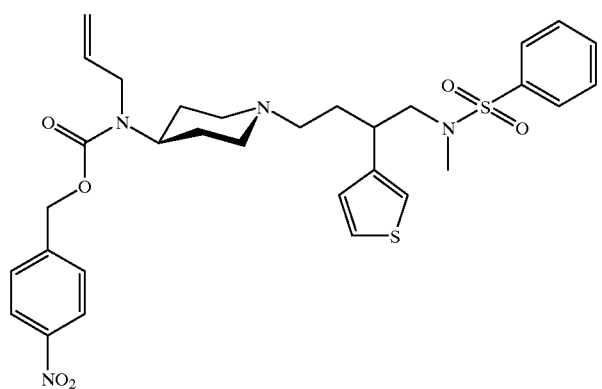

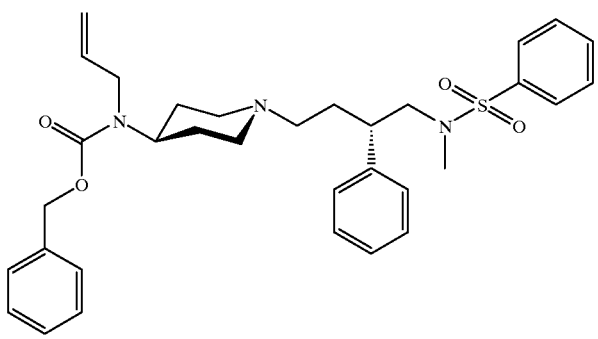
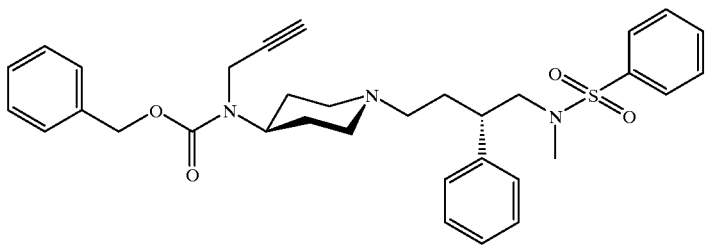
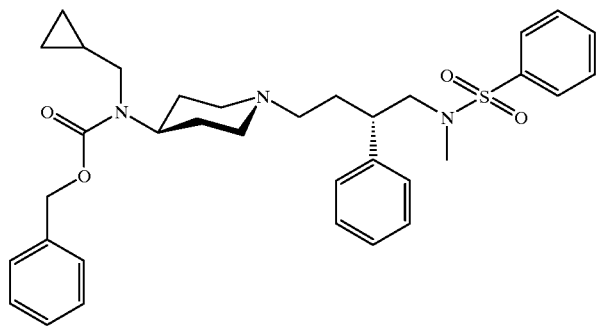
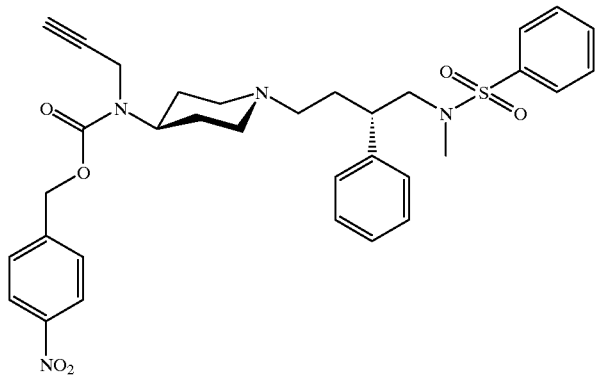
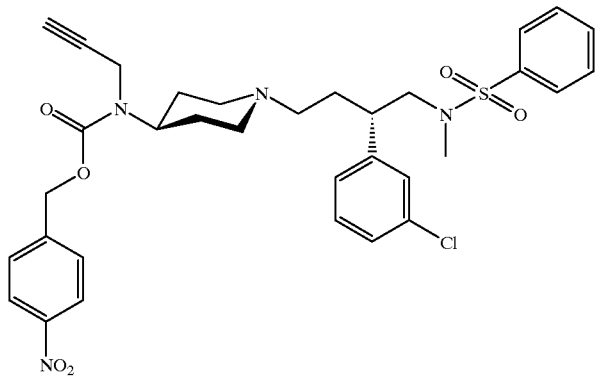

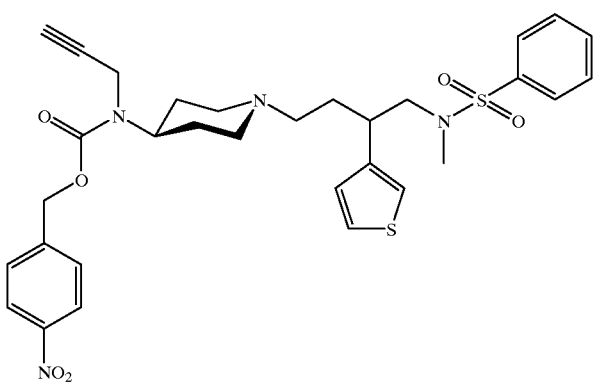
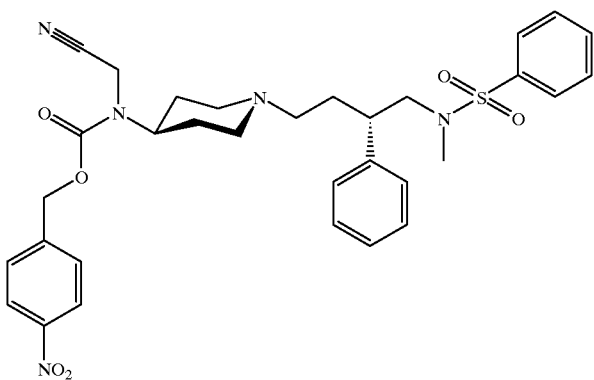
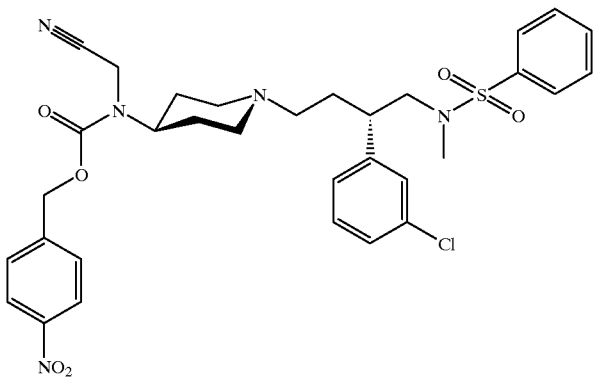
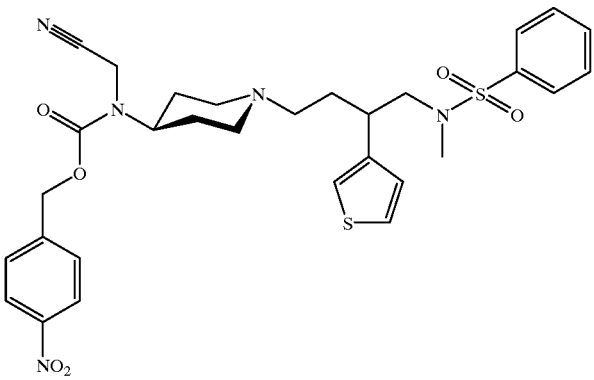

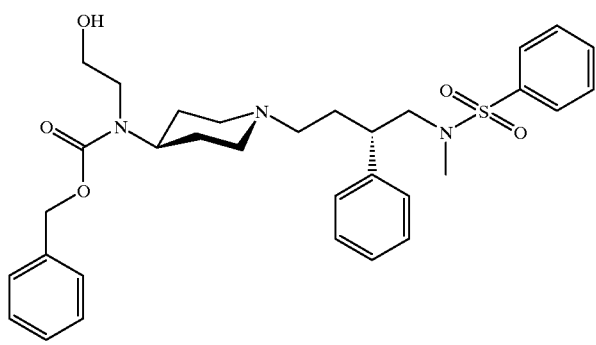
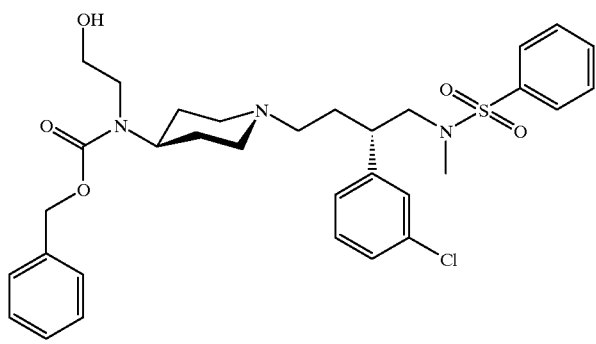
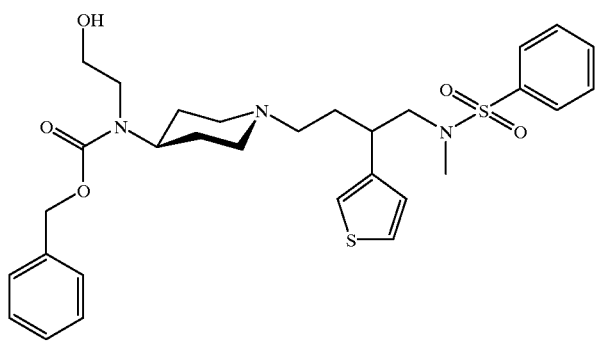
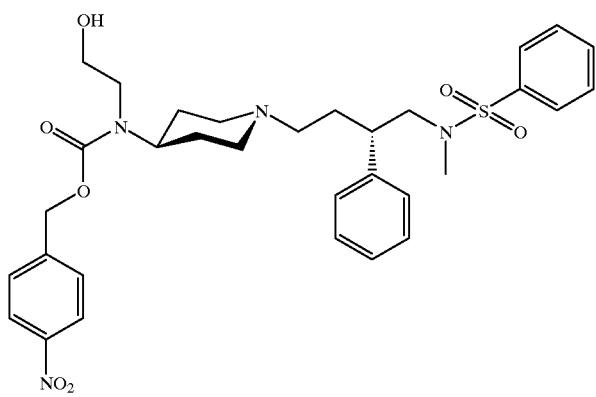

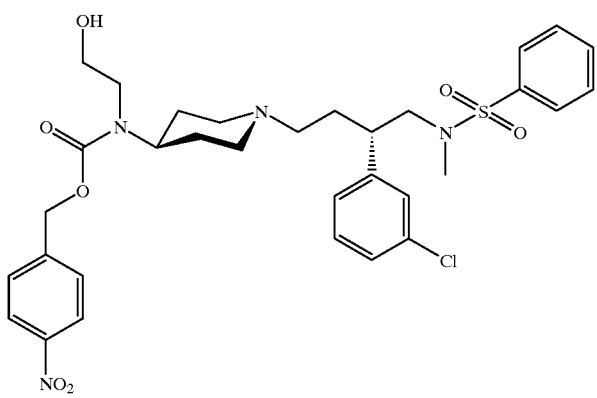
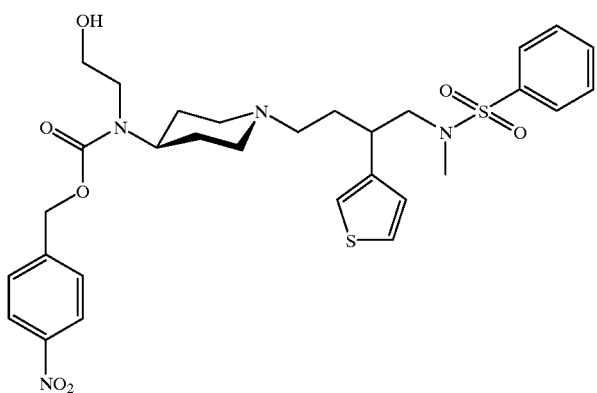
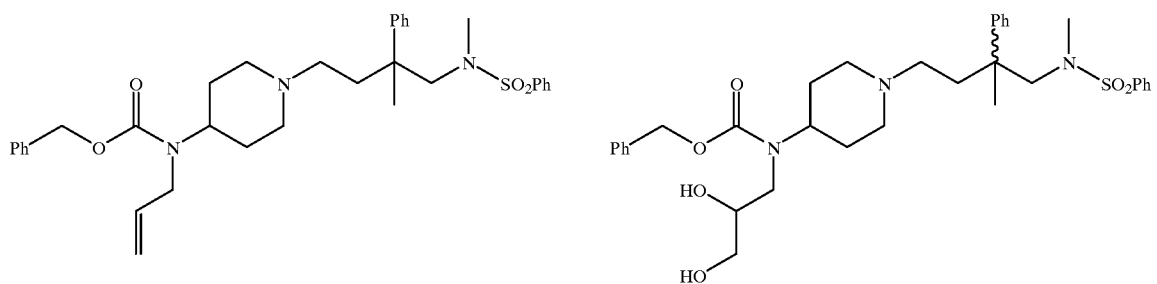
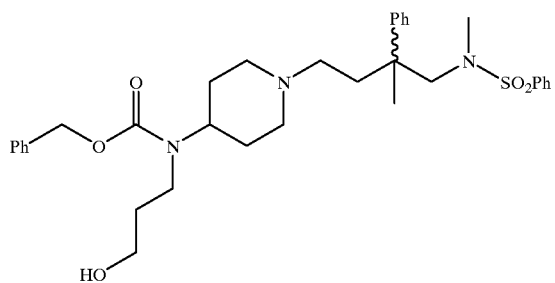
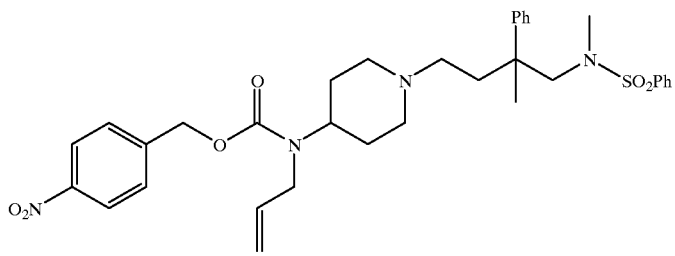

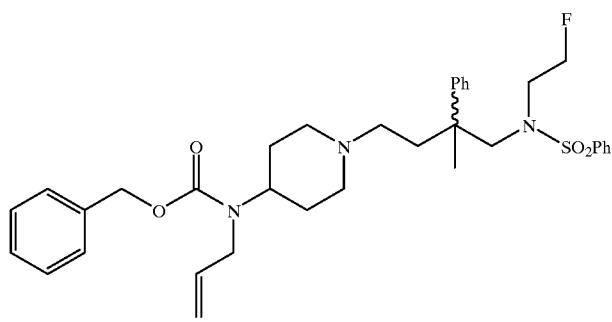
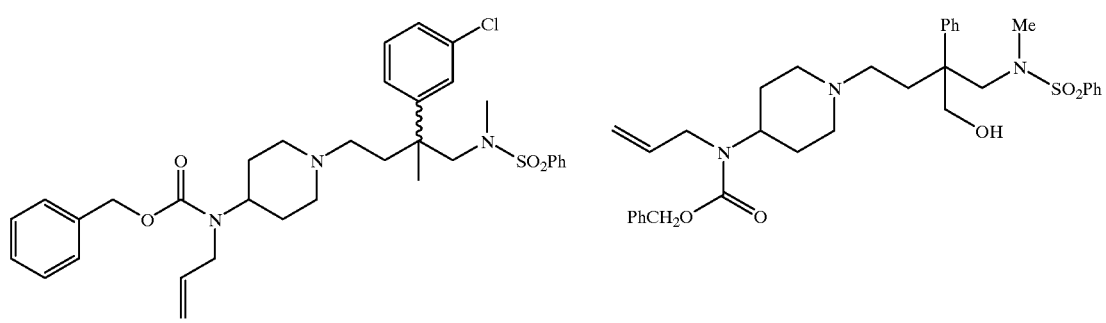
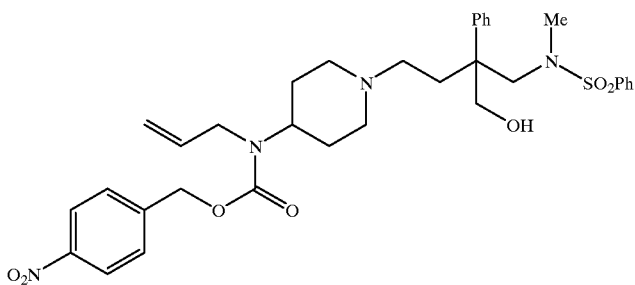
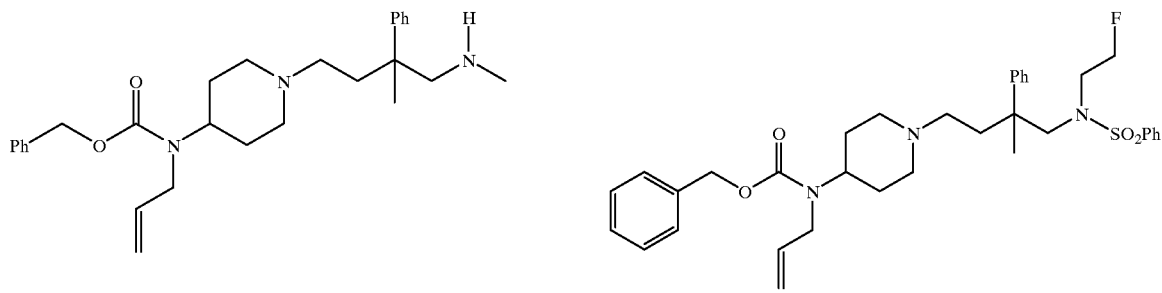
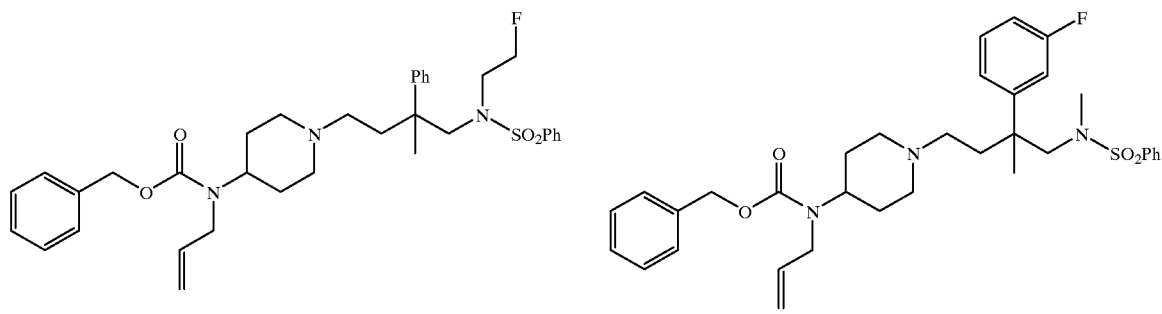

39
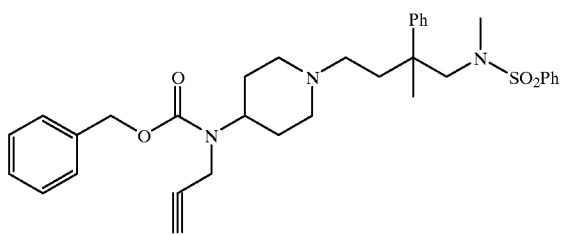
40
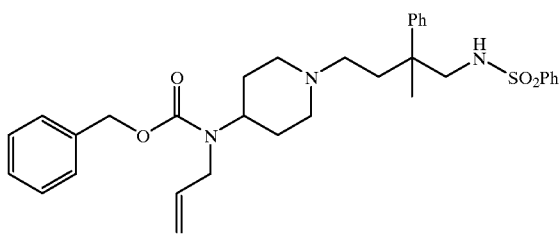
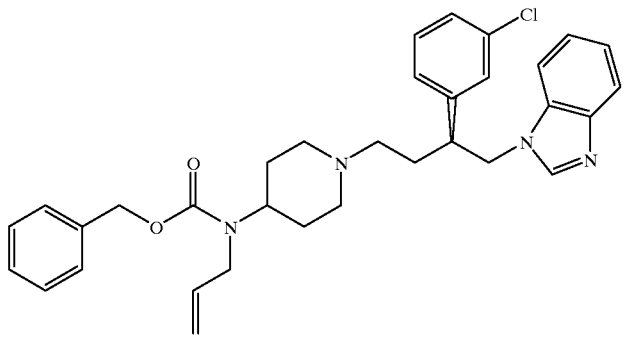
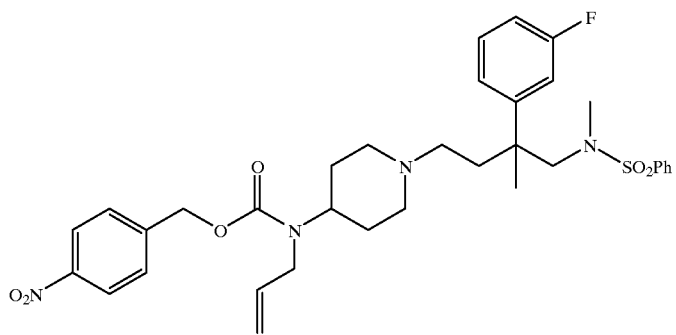
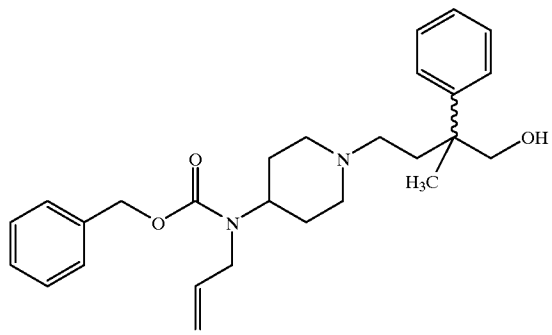
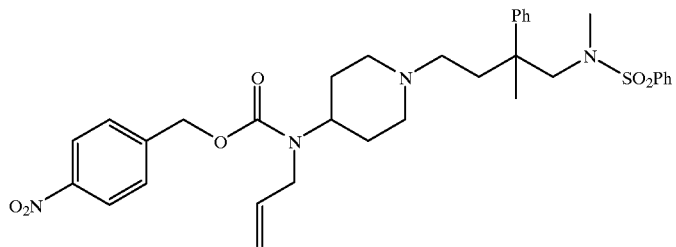

-continued
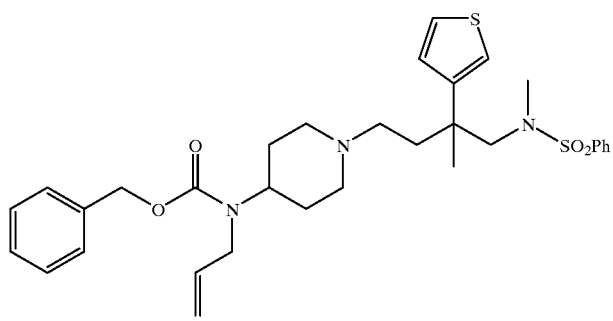
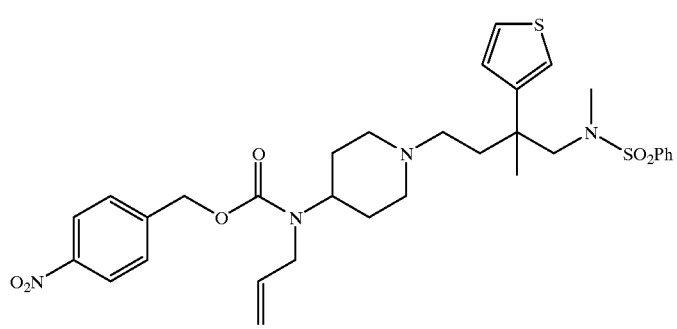
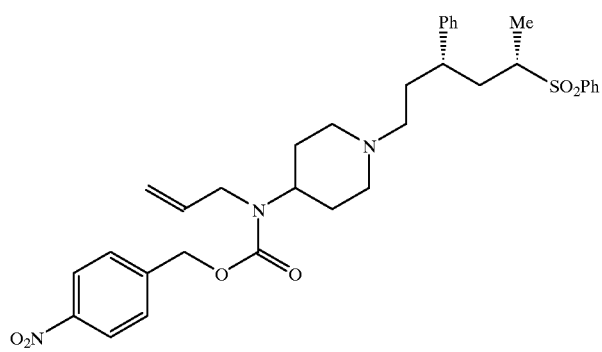
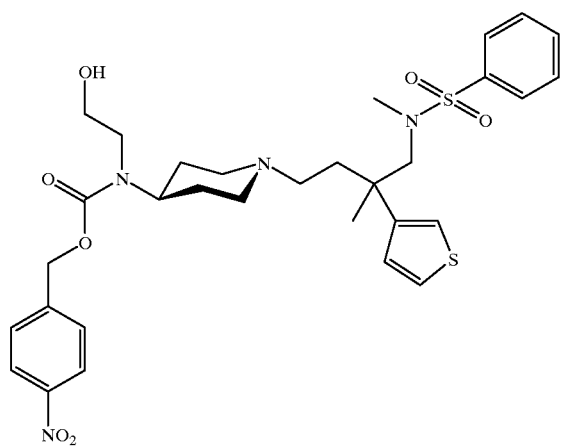

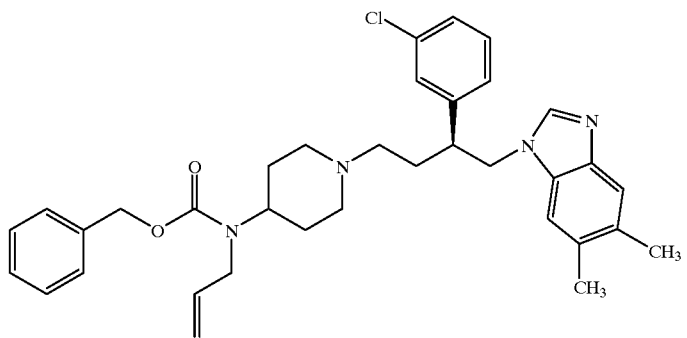
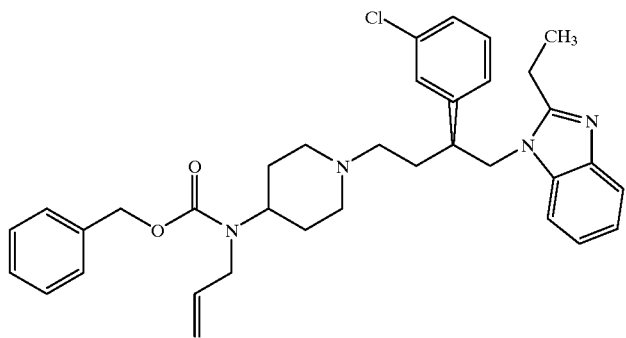
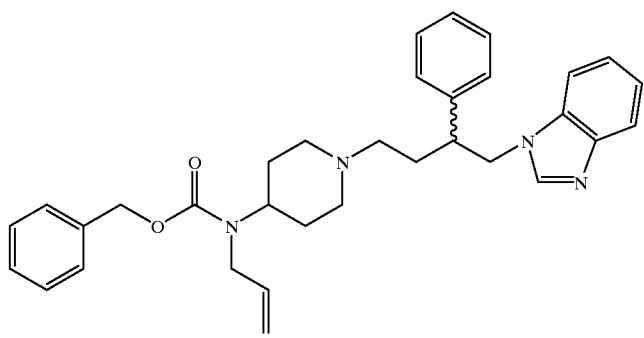
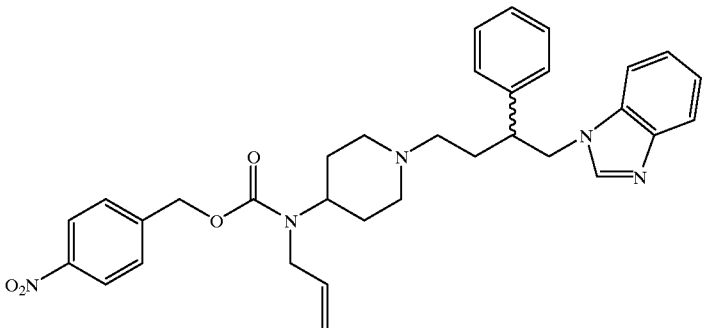
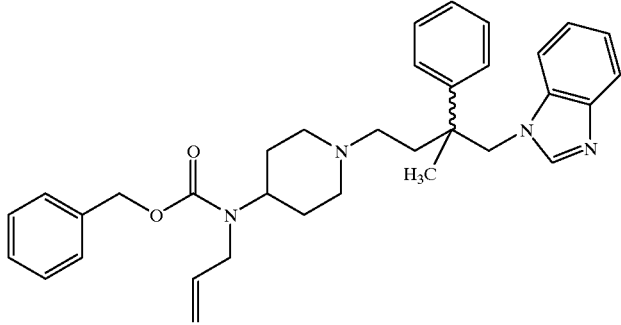

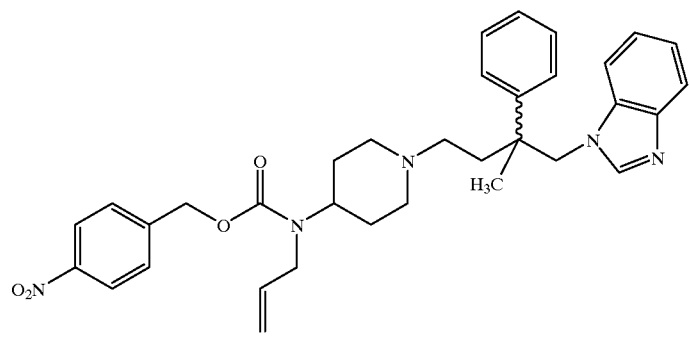
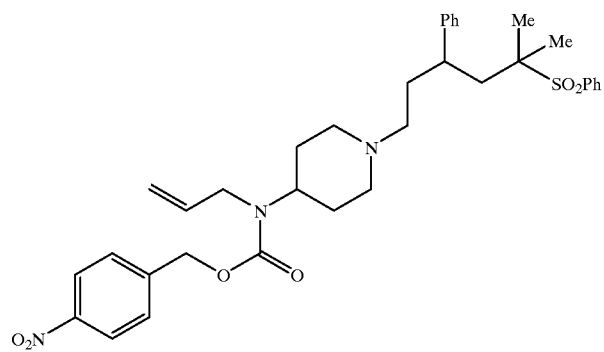
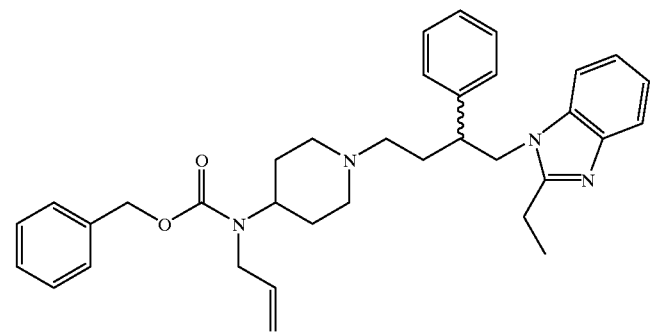
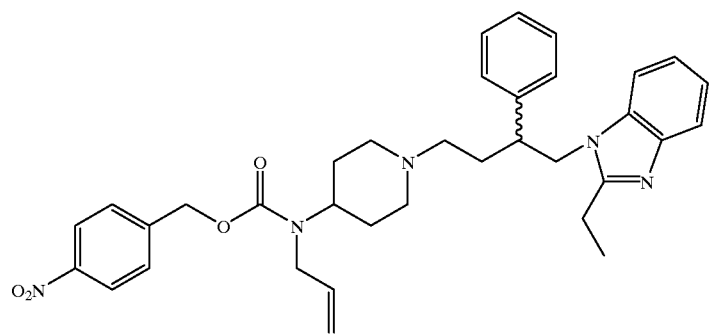

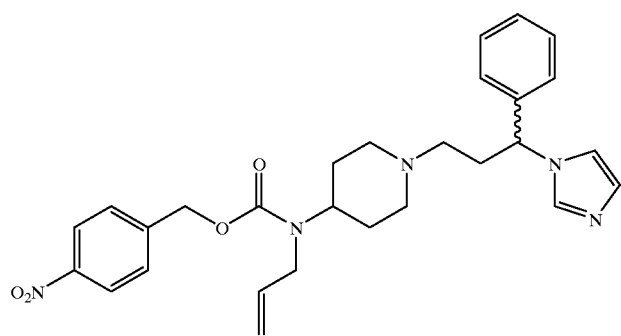
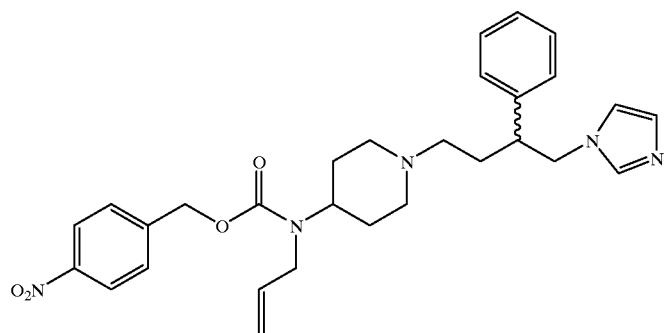
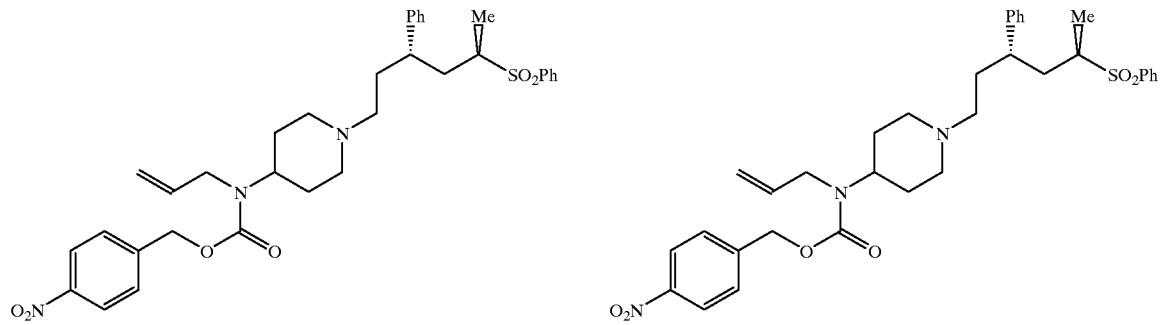
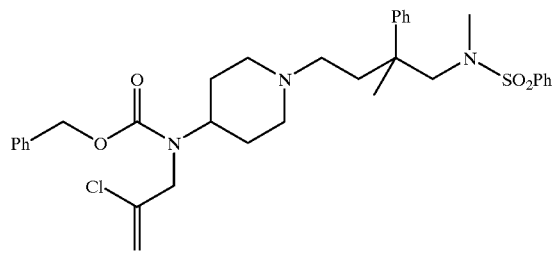
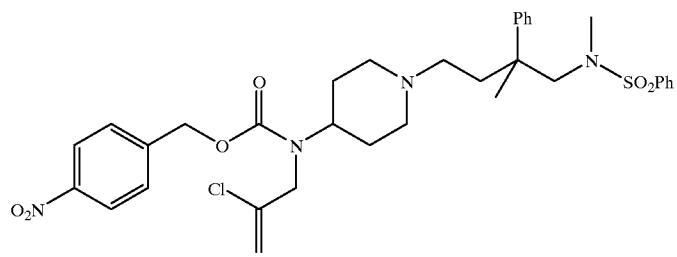

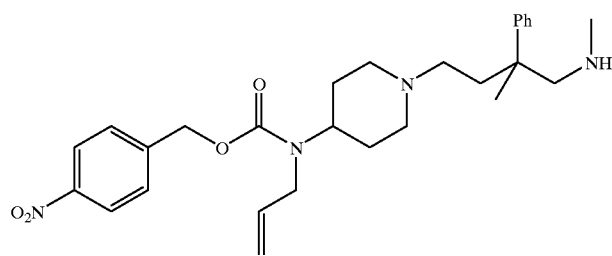
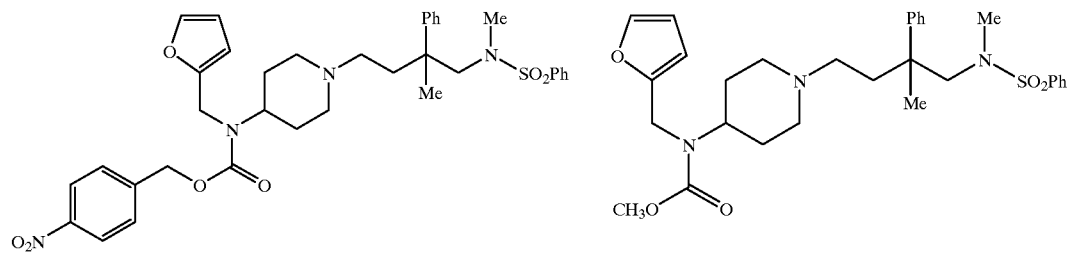
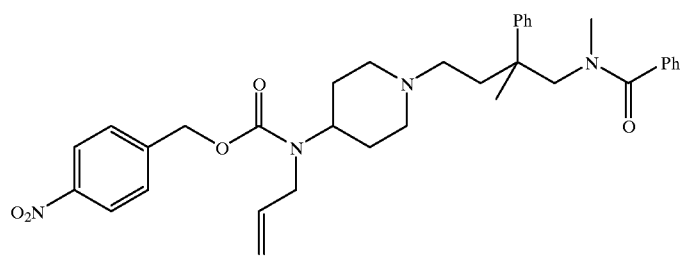
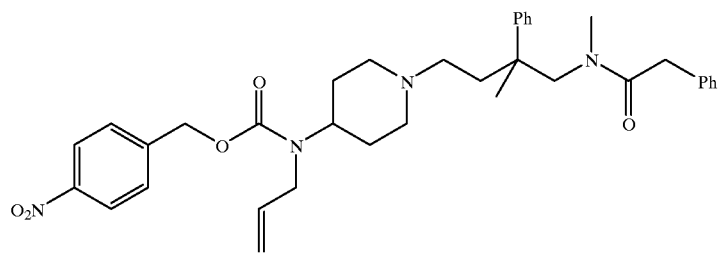
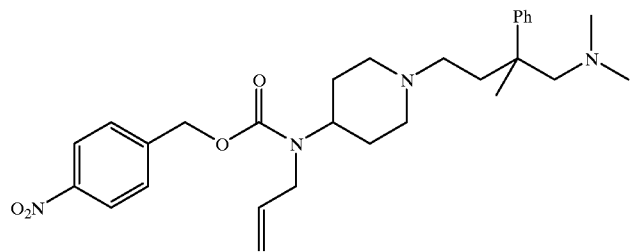
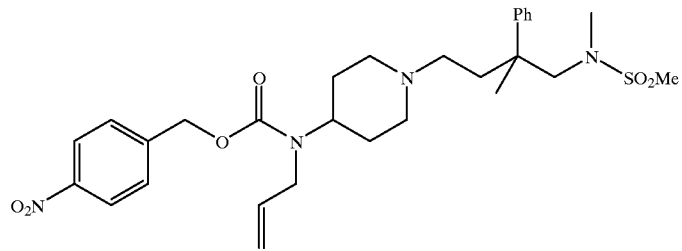

-continued
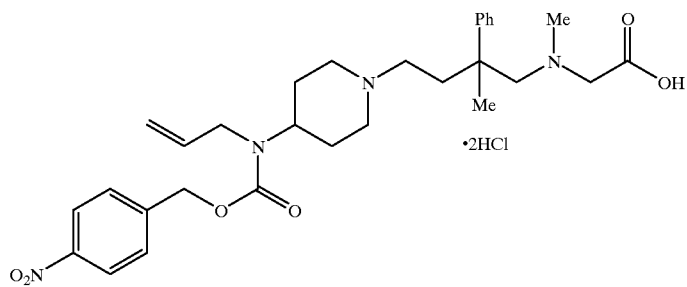
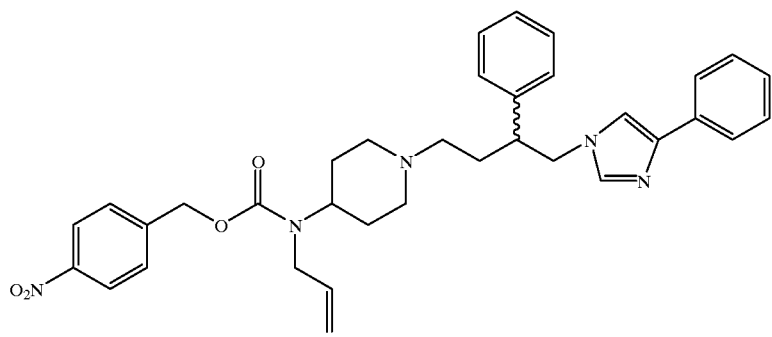
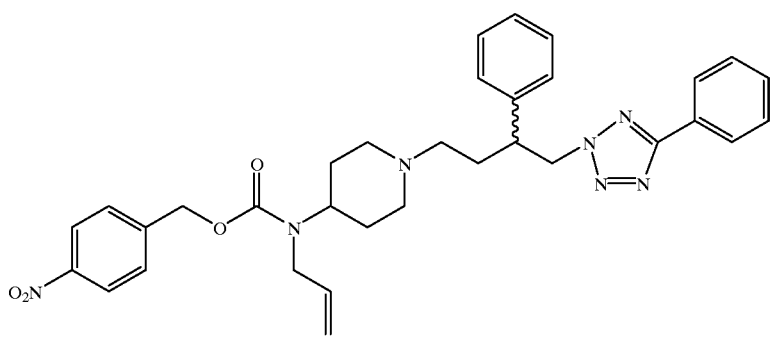
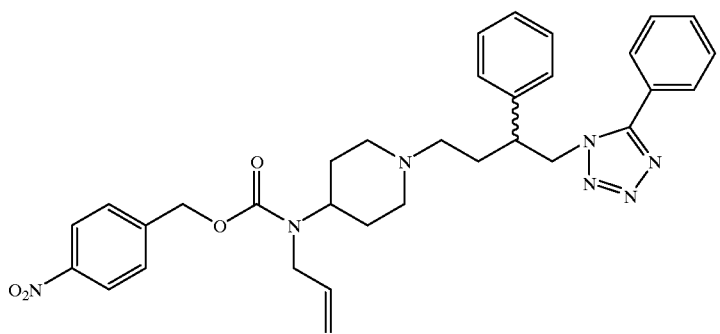
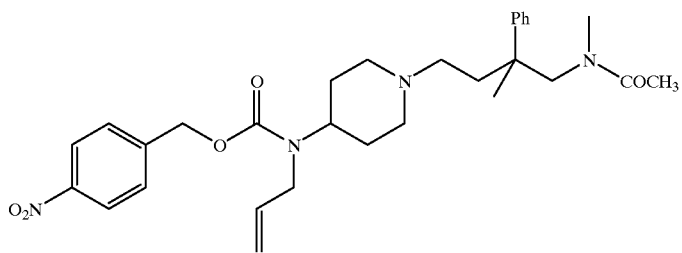

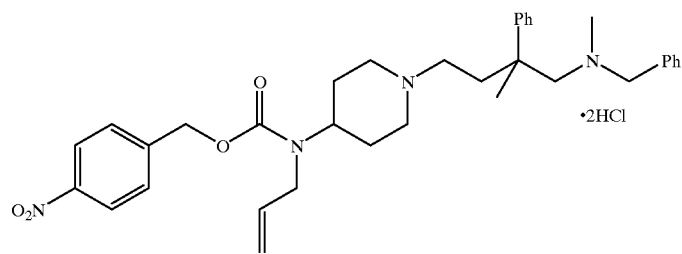
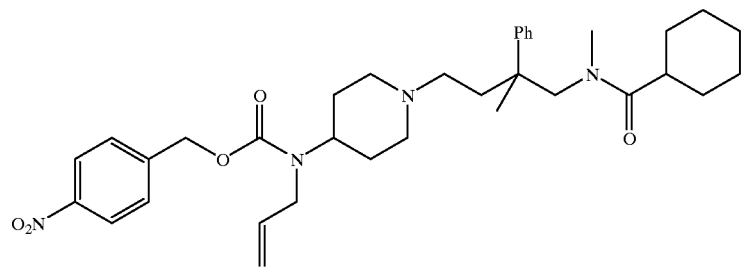
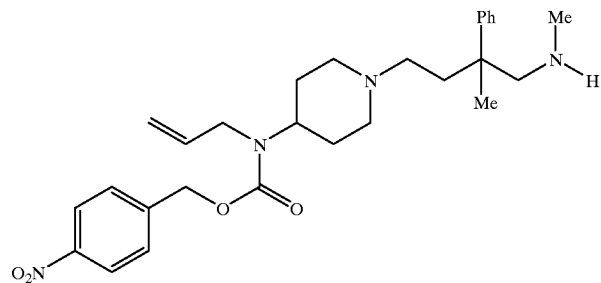
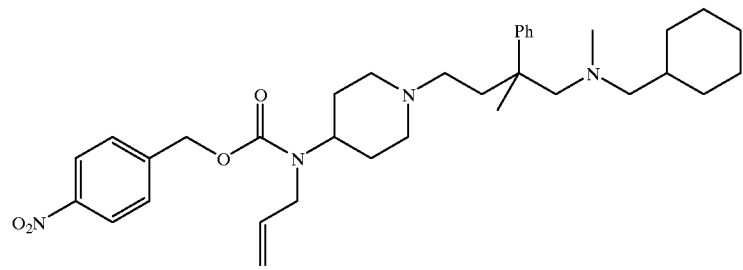
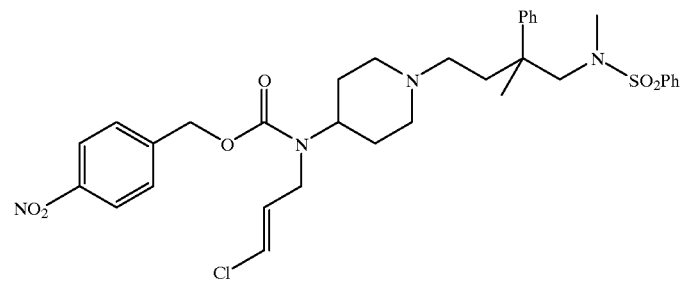
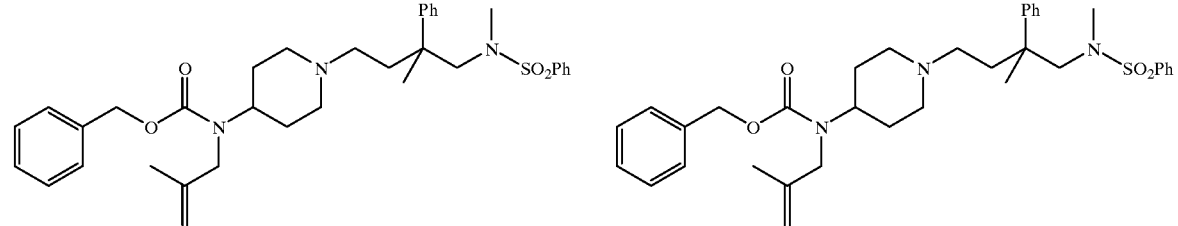

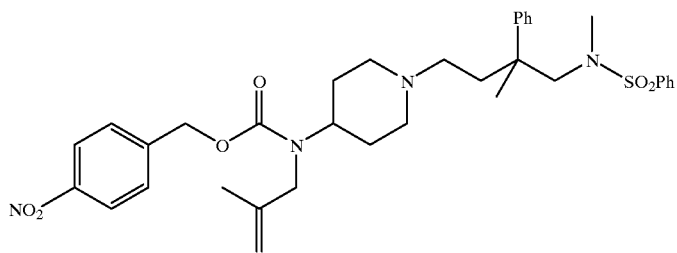
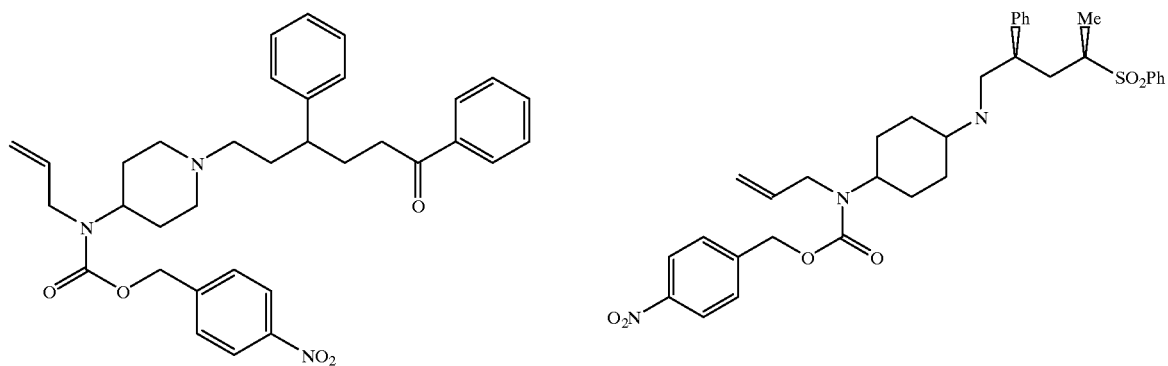
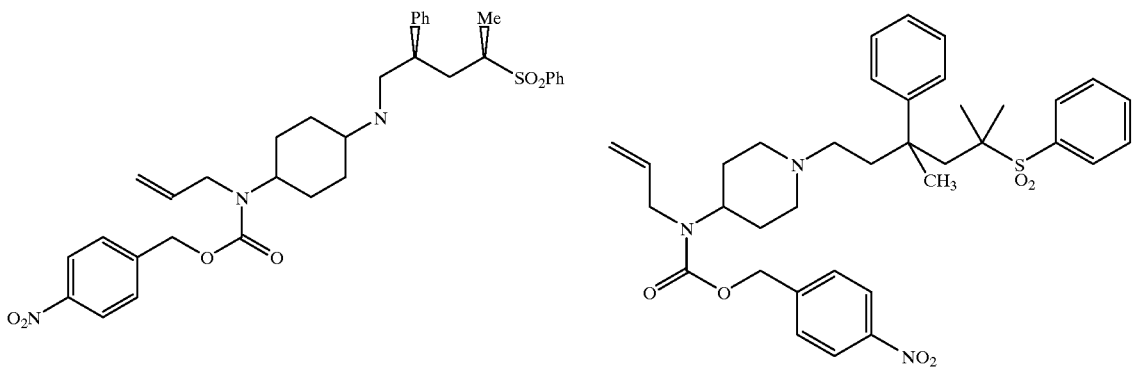
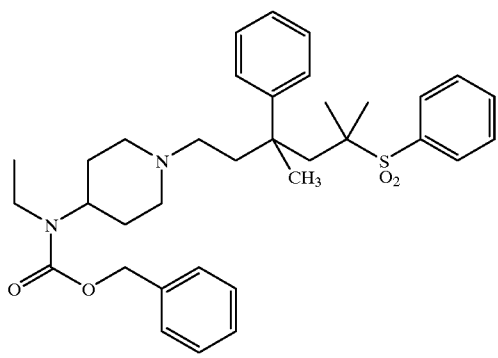
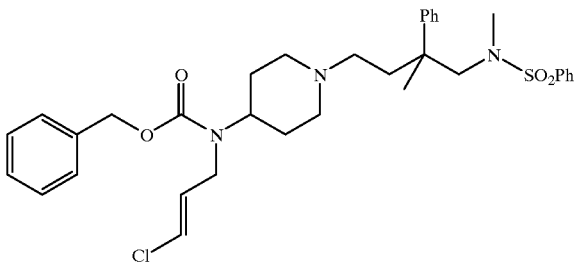
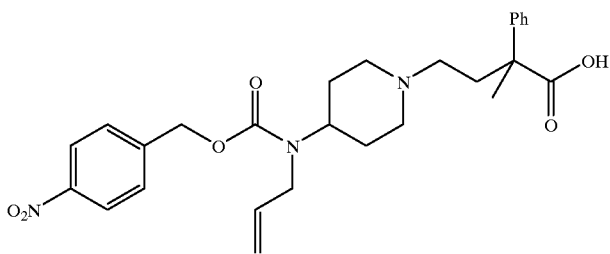

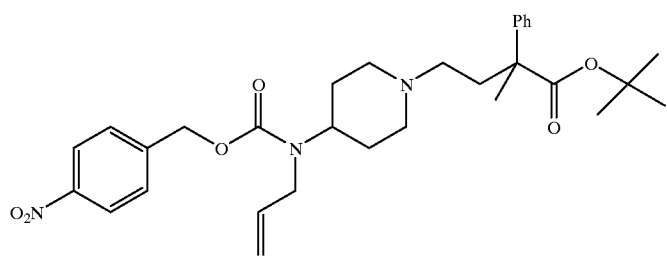
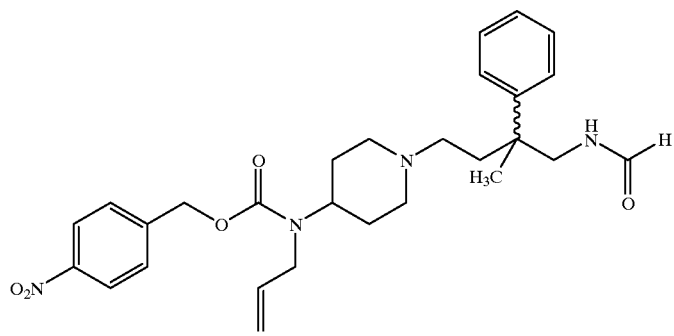
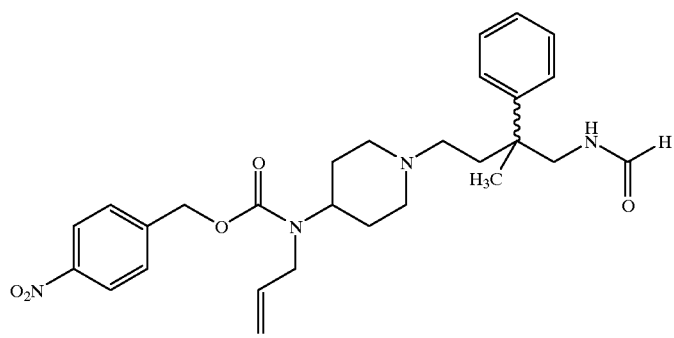
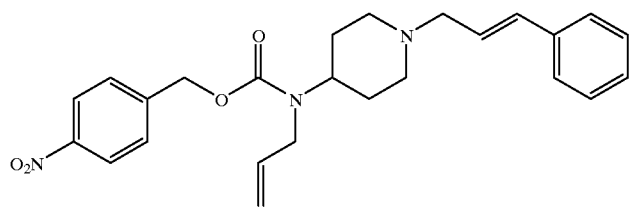
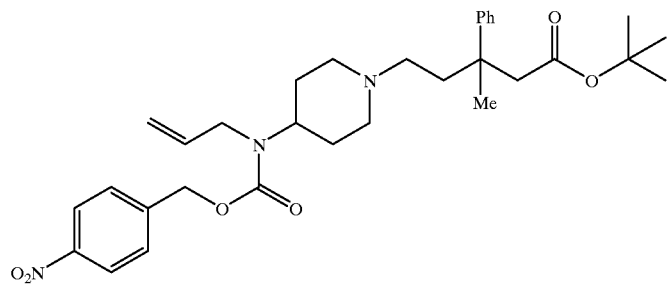

-continued
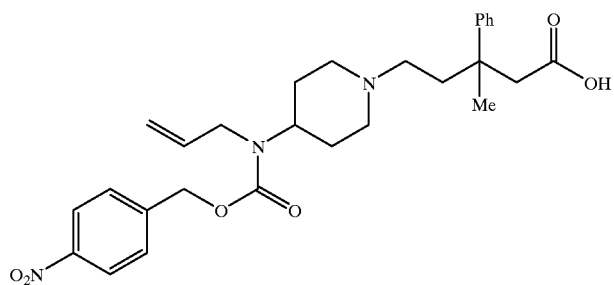
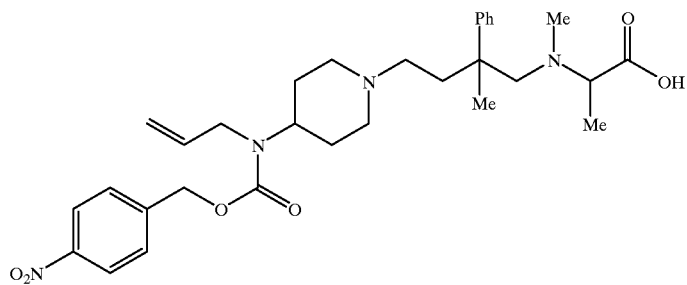
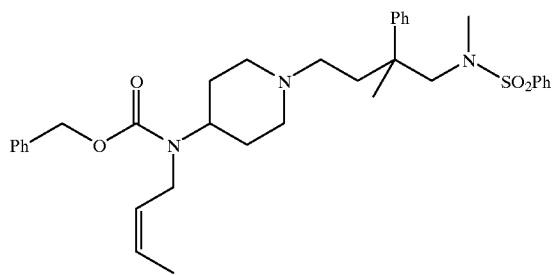
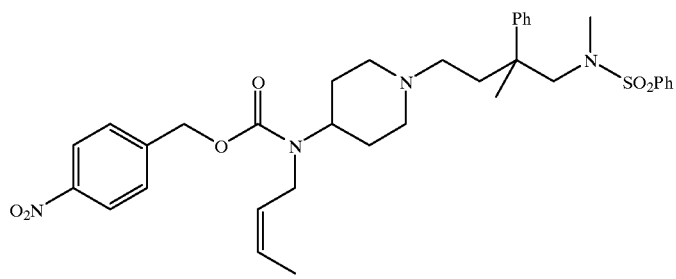
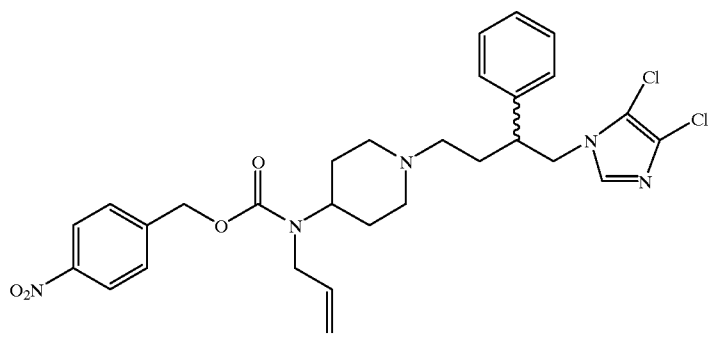

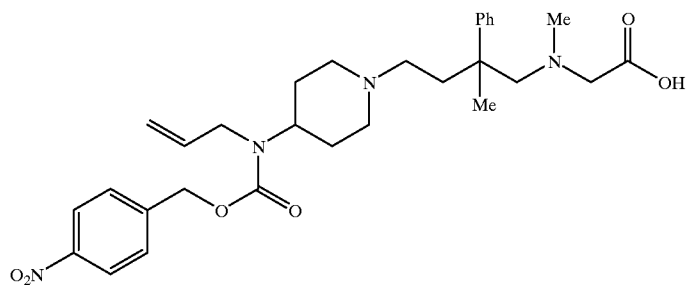
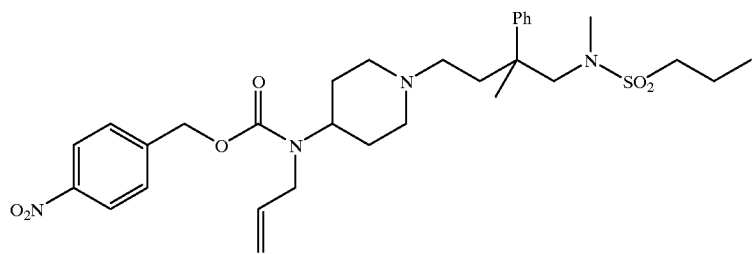
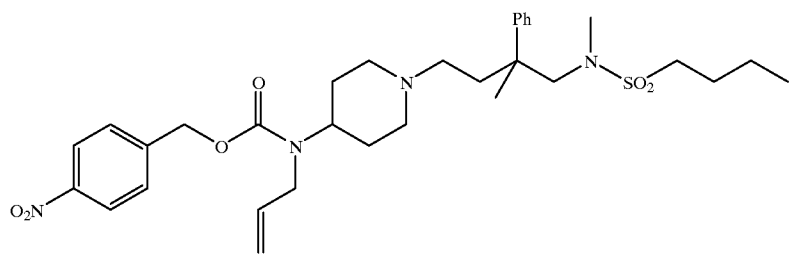
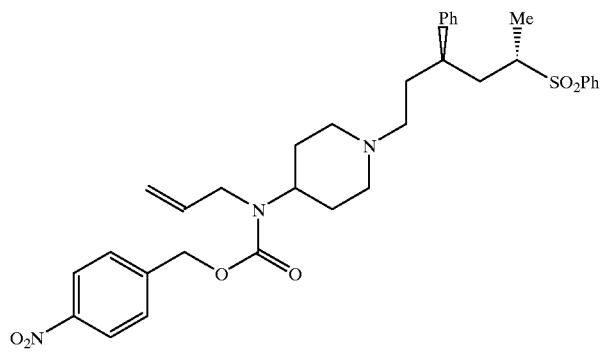
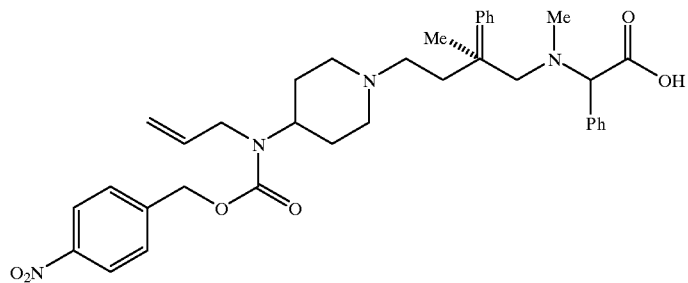

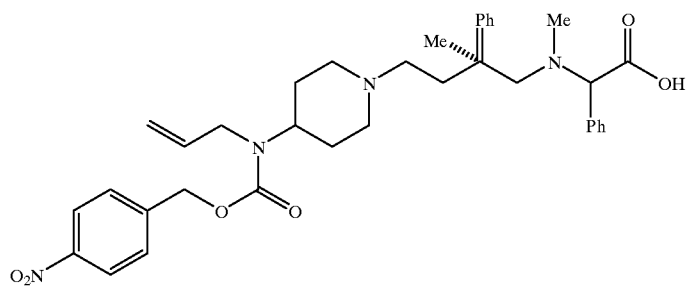
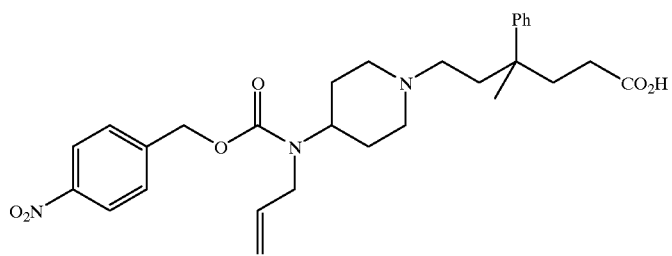
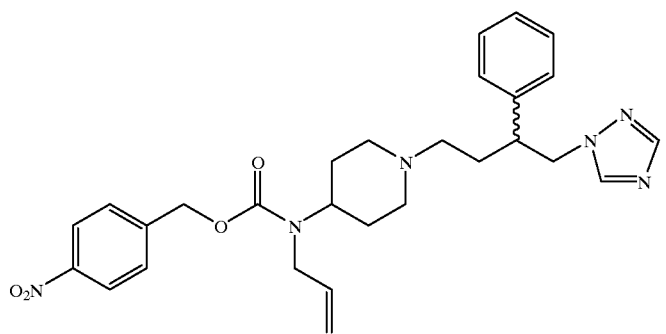
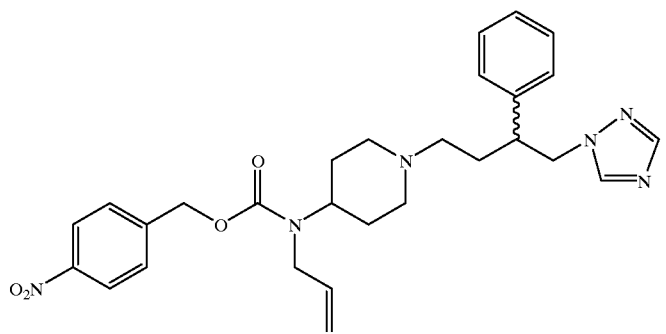
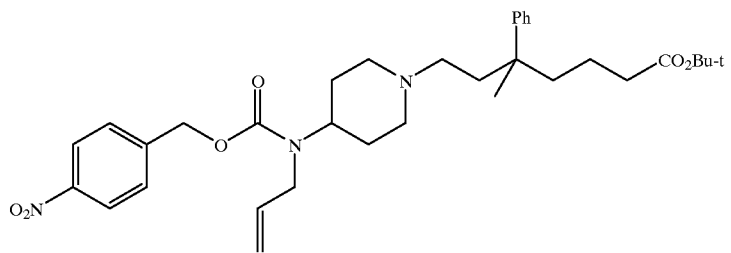

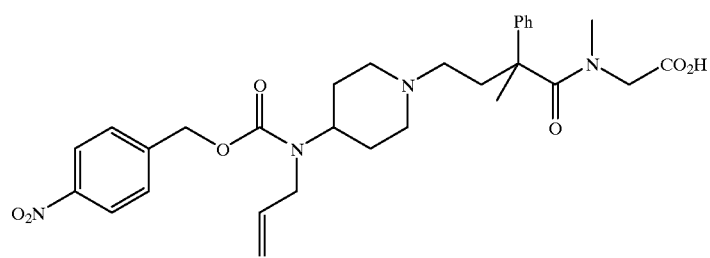
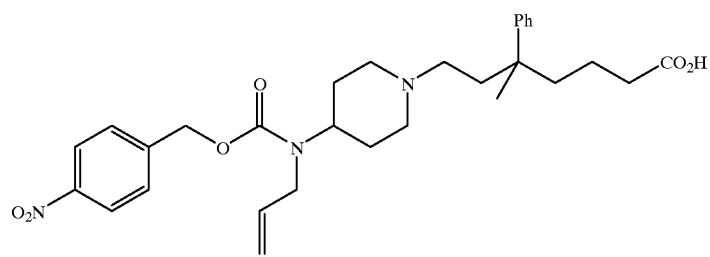
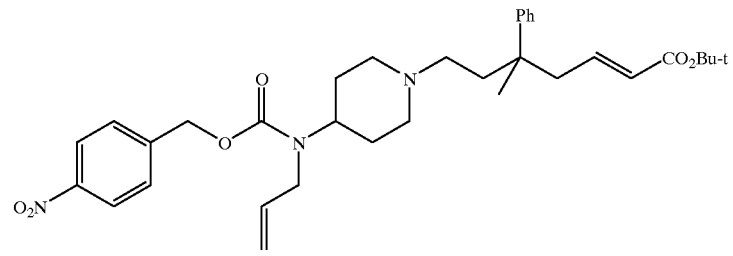
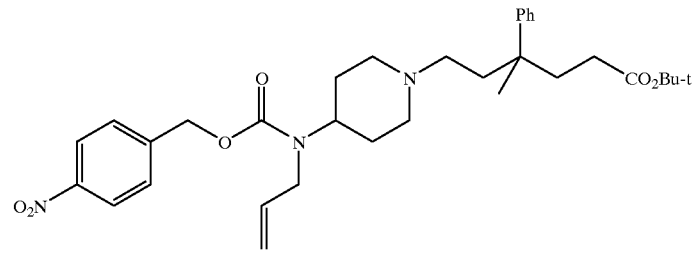
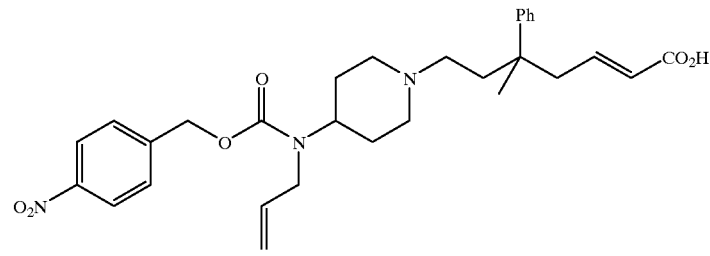
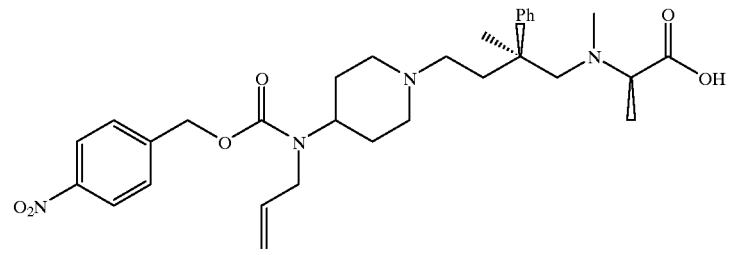

-continued

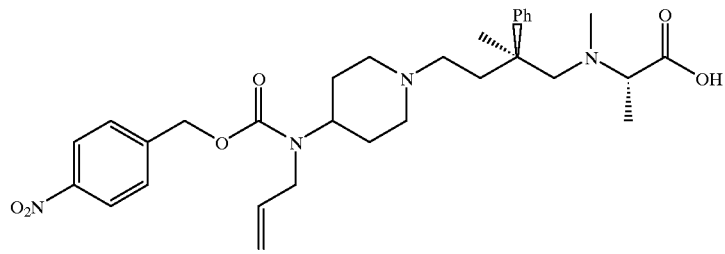

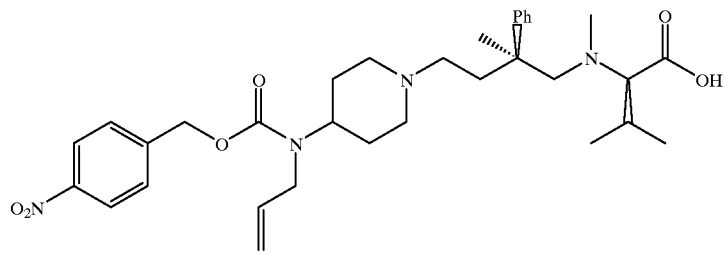

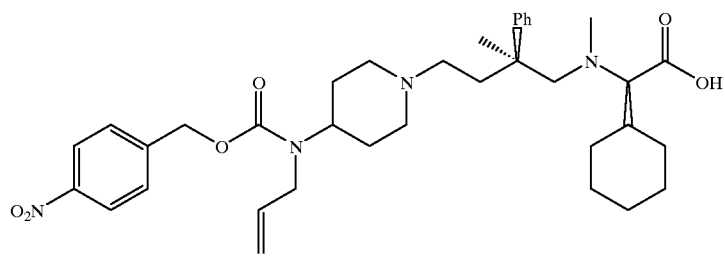

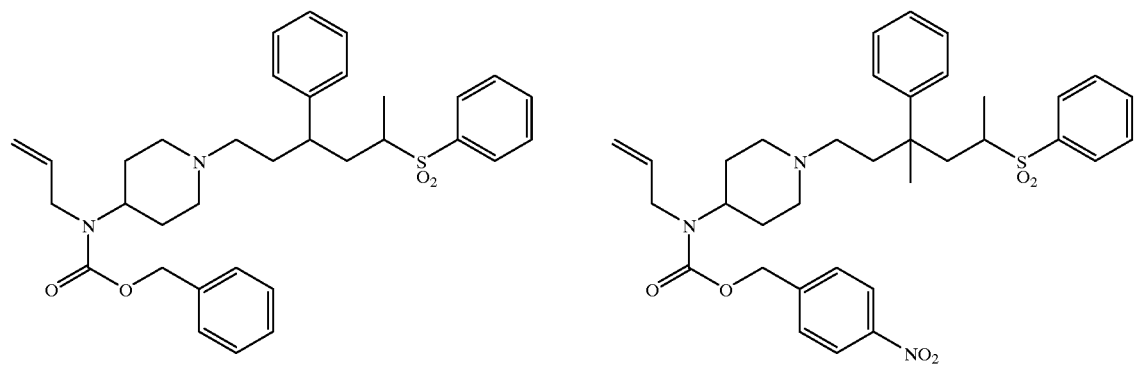

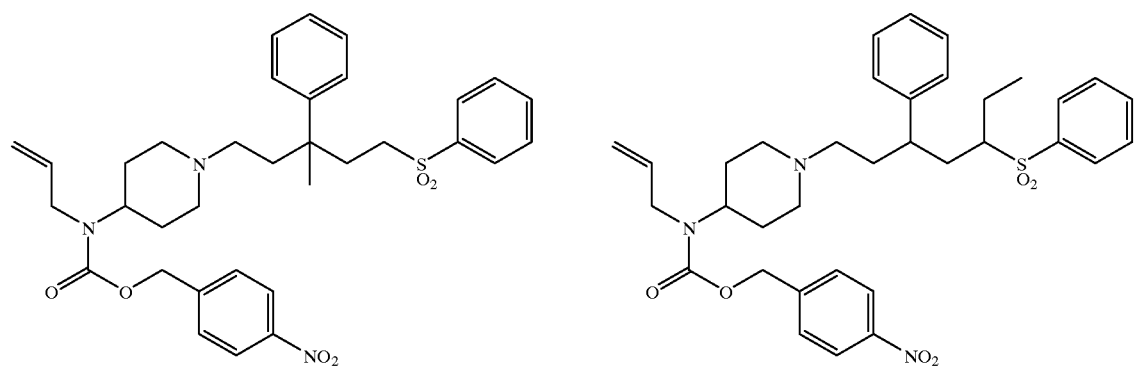

and pharmaceutically acceptable salts thereof.

For use in medicine, the salts of the compounds of the present invention will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the compounds of formula I and salts thereof, for example, hydrates.

The compounds according to the invention may have one or more asymmetric centres, and may accordingly exist both as enantiomers and as diastereoisomers. It is to be understood that all such isomers and mixtures thereof are encompassed within the scope of the present invention.

The subject compounds are useful in a method of modulating chemokine receptor activity in a patient in need of such modulation comprising the administration of an effective amount of the compound. Exemplifying the invention is the use of the compounds disclosed in the Examples and elsewhere herein.

The present invention is directed to the use of the foregoing compounds as modulators of chemokine receptor activity. In particular, these compounds are useful as modulators of the chemokine receptors, including CCR-1, CCR-2, CCR-2A, CCR-2B, CCR-3, CCR-4, CCR-5, CXCR-3, and/or CXCR-4. These compounds are particularly useful as modulators of the chemokine receptors CCR-3 or CCR-5, and especially useful as modulators of the chemokine receptor CCR-5.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.*, 177, 851–856 (1993), and the assay for CCR-2 and/or CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 receptor in the aforementioned assays, generally with an $IC_{50}$ of less than about 10 $\mu$M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, including asthma and allergic diseases, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors, including CCR-1, CCR-2, CCR-2A, CCR-2B, CCR-3, CCR-4, CCR-5, CXCR-3, and CXCR-4. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-1, CCR-2, CCR-2A, CCR-2B, CCR-3, CCR-4, CCR-5, CXCR-3, and CXCR-4. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery. In addition, a compound of the present invention may be used for the prevention of infection by HIV and the prevention of AIDS, such as in post-coital prophylaxis or in the prevention of maternal transmission of the HIV virus to a fetus or a child upon birth.

In a preferred aspect of the present invention, a subject compound may be used in a method of inhibiting the binding of a human immunodeficiency virus to a chemokine receptor, such as CCR-5 and/or CXCR-4, of a target cell, which comprises contacting the target cell with an amount of the compound which is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. In particular, the compounds of the present invention have been found to exhibit primarily antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| 141 W94 | Glaxo Wellcome | HIV infection, AIDS, ARC (protease inhibitor) |
| 1592U89 | Glaxo Wellcome | HIV infection, AIDS, ARC (protease inhibitor) |
| Abacavir (1592U89) | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |

-continued

| Drug Name | Manufacturer | Indication |
|---|---|---|
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| (-) 6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-266 | DuPont-Merck Pharmaceuticals | HIV infection, AIDS, ARC (non-nucleoside reverse transcriptase inhibitor) |
| DMP-450 | AVID (Camden, NJ) | HIV infection, AIDS, ARC (protease inhibitor) |
| Efavirenz (DMP 266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, Tx) | AIDS, ARC |

-continued

| Drug Name | Manufacturer | Indication |
|---|---|---|
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |

-continued

| Drug Name | Manufacturer | Indication |
|---|---|---|
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

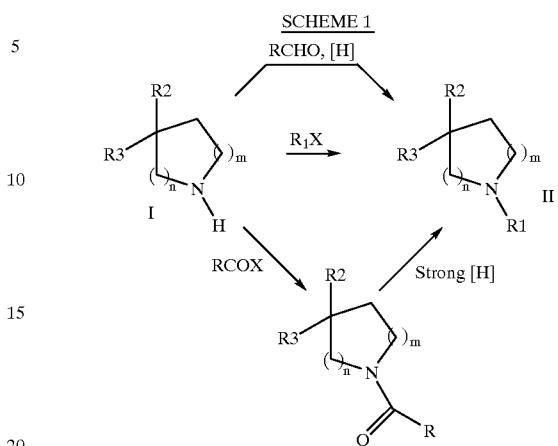

SCHEME 1

The compounds of the present invention are prepared by alkylating heterocycle I under appropriate conditions to provide compound II (Scheme 1). The required starting materials for preparing heterocycle I are available commercially or can be prepared using the methods given below.

Thus, heterocycle I is combined with the appropriate aldehyde and the intermediate imine or iminium species is reduced to the tertiary amine chemically (e.g. using sodium cyanoborohydride, sodium borohydride, or sodium triacetoxyborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention one preparation of a representative aldehyde is described in Hale, J. J.; Finke, P. E.; MacCoss, M. *Bioorganic & Medicinal Chemistry Letters* 1993, 3, 319–322.

In an alternative embodiment of the present invention, heterocycle I can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol converted to either the alkyl halide using methods described in March J. "Advanced Organic Chemistry", 4th ed., John Wiley & Sons, New York, pp. 431–433 (1992), or alkyl sulfonate ester using methods described in March J. "Advanced Organic Chemistry", 4th ed., John Wiley & Sons, New York, p. 498–499 (1992).

In an alternative embodiment of the present invention, I can be acylated to give a tertiary amide; subsequent reduction with a strong reducing agent (e.g. diborane; borane in THF; borane dimethylsulfide, or lithium aluminum hydride) will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate I. The product amide can in and of itself be a chemokine receptor modulator or can be reduced as noted above to give the tertiary amine.

Optionally, compound II may be further modified in subsequent reactions, as illustrated below.

the acetylene derivative III. Palladium-catalysed hydrostannylation preferentially forms the 3-tributylstannyl olefin IV. The minor product from this reaction can also isolated and carried through the sequence described below. Compound

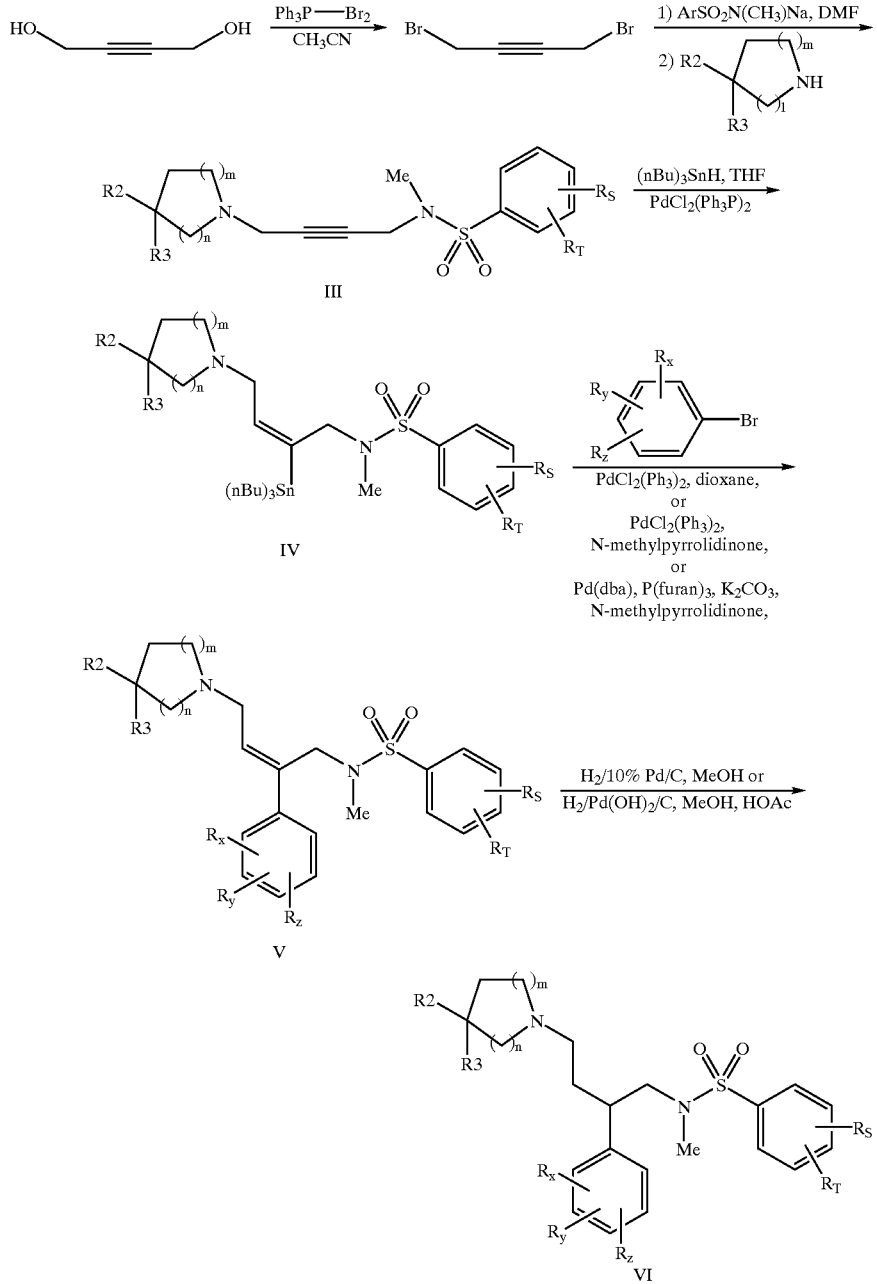

In an alternative embodiment of the present invention, compounds of interest can be prepared by activating the hydroxyl groups of 1,4-dihydroxy-2-butyne, for example by treatment with triphenylphosphine dibromide in acetonitrile, to give 1,4-dibromo-2-butyne (Scheme 2). Displacement of one bromide with the sodium salt of an arylsulfonamide (wherein Rs and Rt are substituents on the phenyl or Ar as defined herein), followed by displacement of the other bromide with a suitable cyclic secondary amine, provides IV can be converted to the corresponding 3-aryl derivative V by treatment with an aryl bromide (wherein Rx, Ry and Rz are substituents on the phenyl or heteroaryl as defined herein) in the presence of a suitable palladium catalyst at or above room temperature. Suitable catalysts include palladium acetate and triphenylphosphine, bis (triphenylphosphine) palladium (II) chloride, or palladium (0) bis(dibenzylidineacetone) in the presence of triphenylphosphine or tri-2-furylphosphine. Suitable solvents include 1,4-dioxane, DMF, and N-methylpyrrolidinone. A base such as potassium carbonate or potassium phosphate may also be employed. Compound V may be employed as a chemokine receptor modulator itself or it can be reduced to saturated derivative VI by standard conditions, for example catalytic hydrogenation with palladium on carbon or with palladium hydroxide in the presence of a mild acid such as acetic acid.

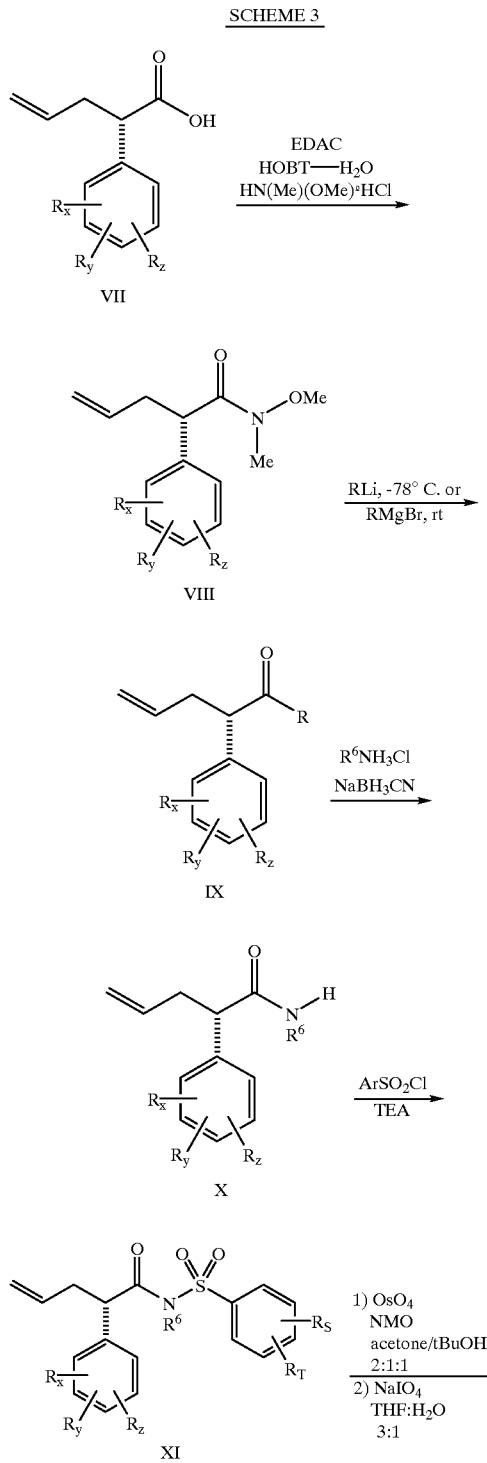

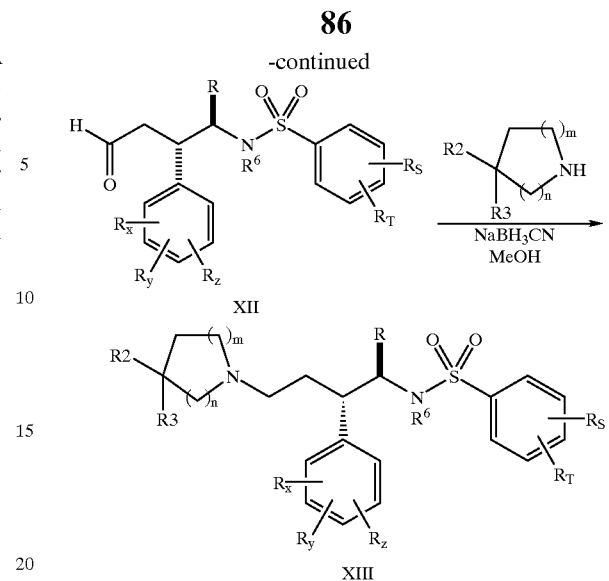

In an alternative embodiment of the present invention, the allyl acid VII (prepared, for example, as described in Hale et al; see above) can be converted into the N-methyl-N-methoxy amide VIII, which is then treated with an alkyl or aryl metal reagent, for example methyllithium or butyllithium, to provide the ketone IX (Scheme 3). The ketone can be converted into an imine which can then be reduced to secondary amine X chemically, (e.g using sodium cyanoborohydride or sodium borohydride), or catalytically (e.g. using hydrogen and palladium on carbon or Raney nickel catalyst). Acylation under standard conditions, for example with an acid chloride, provides the corresponding amide. Alternatively, amine X can be sulfonylated, for example with a alkyl or aryl sulfonyl chloride or an alkyl or aryl sulfonic anhydride, to give (for aryl substituted sulfonylating reagents) sulfonamide XI. The allyl group in XI can be oxidatively cleaved to aldehyde XII with osmium tetroxide followed by sodium periodate or with ozone at low temperature. Reductive amination of aldehyde XII with azacycle I can then be carried out under the conditions described above to give the desired product XIII.

SCHEME 4

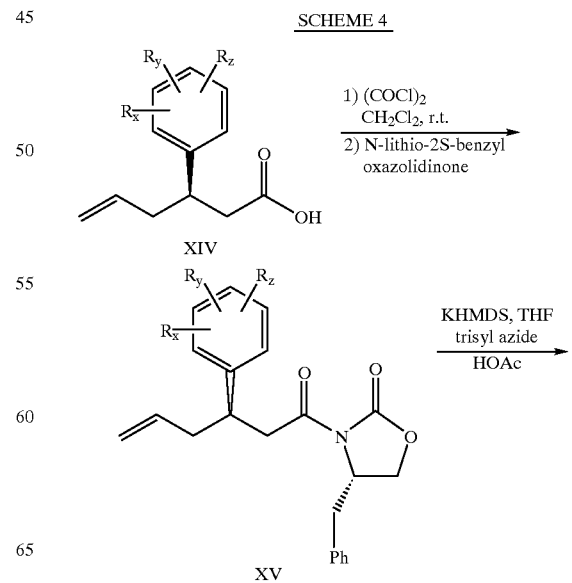

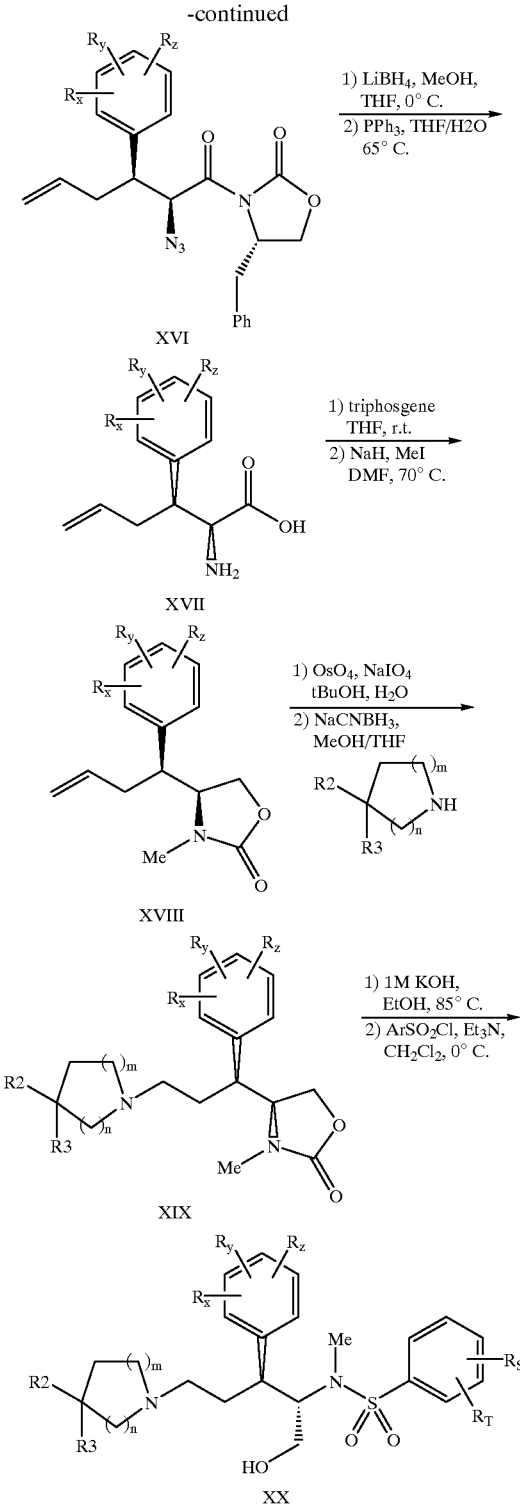

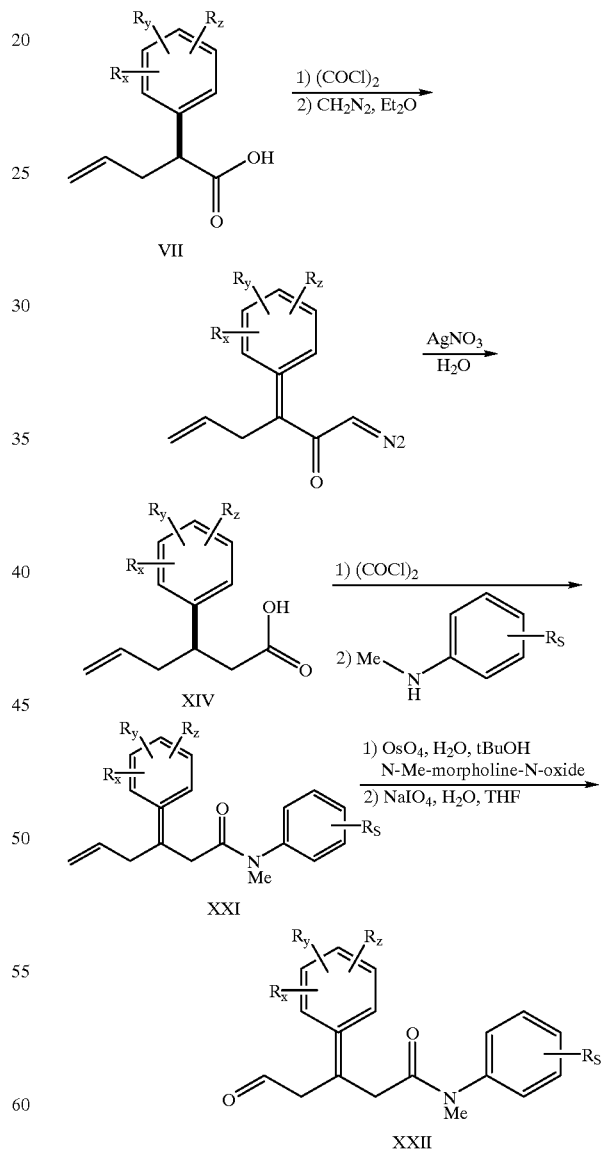

can be carried out by a variety of metal hydride reagents (e.g. LiBH$_4$/MeOH, LiAlH$_4$, etc.). The azide is then reduced by treatment with PPh$_3$/H$_2$O to provide alcohol XVII. Formation of cyclic carbamate XVIII is accomplished by literature methods; i.e. phosgene, triphosgene or carbonyl diimidazole, followed by N-alkylation with sodium hydride and methyl iodide. The target compounds are prepared by oxidative cleavage of the olefin to the aldehyde followed by reductive amination with an amine salt as described for Scheme 1, to provide XIX. Hydrolysis of the cyclic carbamate under basic conditions (for example, potassium hydroxide in ethanol at elevated temperature) followed by selective amide formation at 0° C. by combining with an acylating agent or a sulfonating agent such as an arylsulfonyl chloride gives the corresponding hydroxyamides or hydroxysulfonamides (i.e. XX).

Preparation of hydroxymethyl derivatives of the target compounds is outlined in Scheme 4. The oxazolidinone imide XV is prepared from acid XIV, by formation of the corresponding acid chloride (by treatment with oxalyl chloride or thionyl chloride) and addition of N-lithio 2(S)-benzyl oxazolidinone. The enolate azidation can be 10 accomplished by a variety of methods, such as the procedure of Evans, D. A.; et. al. *J. Am. Chem. Soc.* 1990, 112, 4011–4030. Reduction of the oxazolidinone moiety of XVI Compounds with alternate arrangements of an amide bond are prepared as shown in Scheme 5. Acid VII can be homologated under Arndt-Eistert conditions to give the chain-extended acid XIV, which can be derivatized under standard acylating conditions with, for example, an aniline derivative, to give the amide XXI. Oxidative cleavage of the olefin with osmium tetroxide or ozone then provides aldehyde XXII as an intermediate suitable for coupling as described earlier.

SCHEME 6

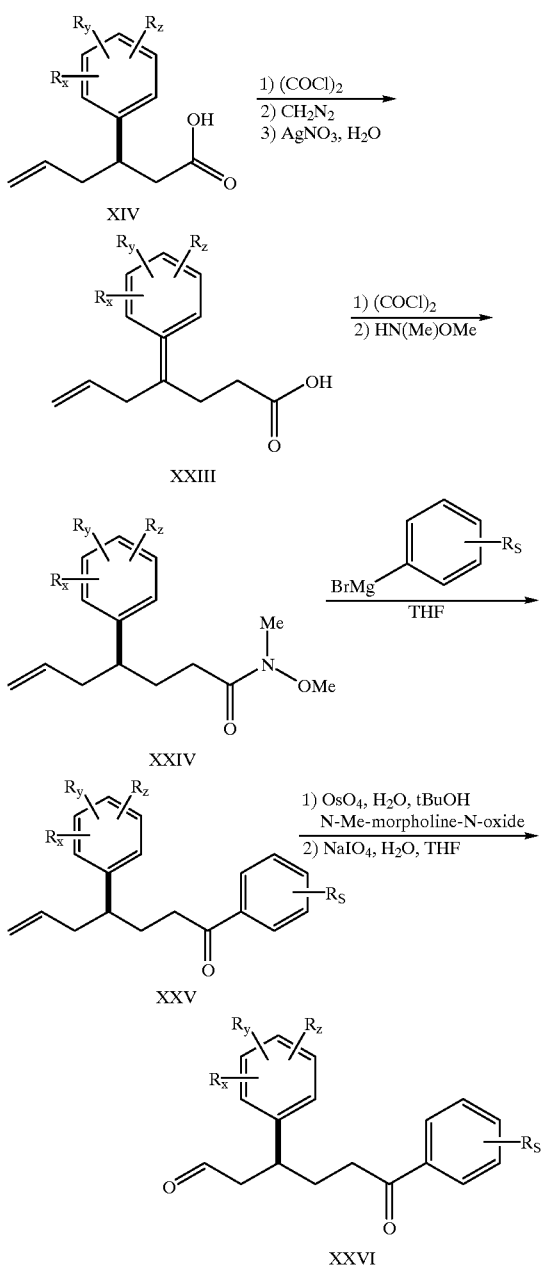

SCHEME 7

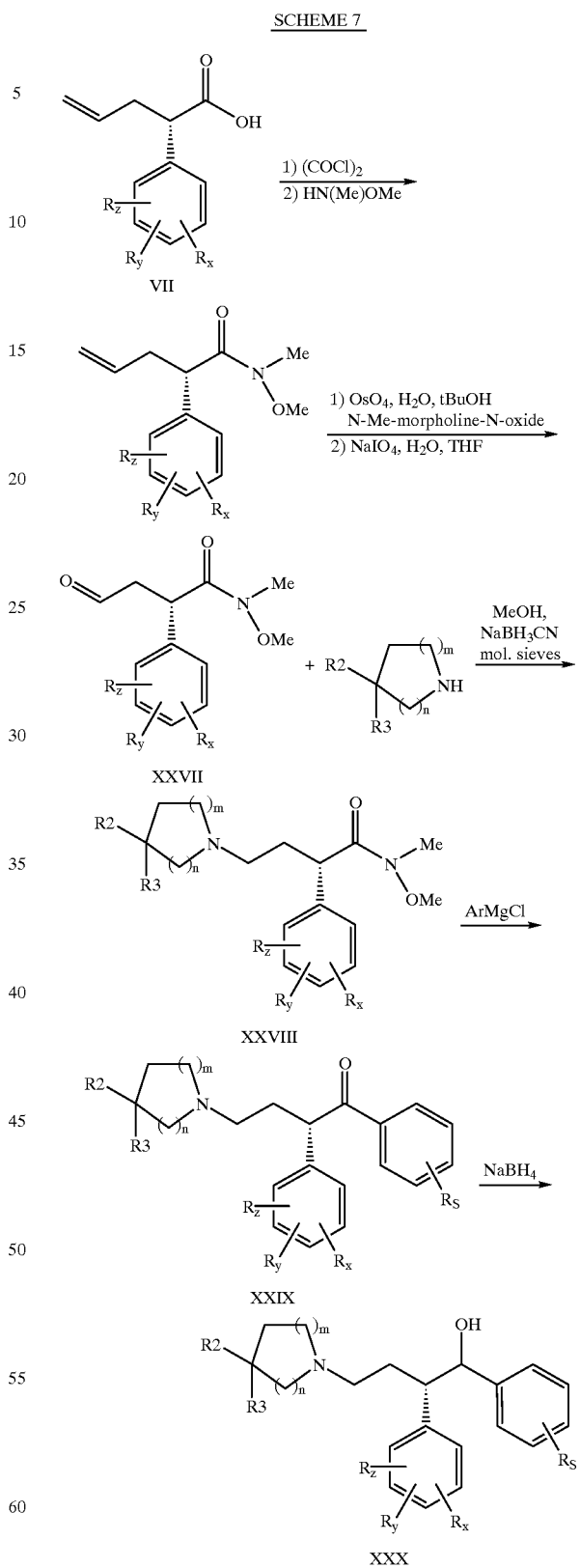

In addition, ketone derivatives are prepared by an extension of the chemistry given above, as shown in Scheme 6. An Arndt-Eistert chain extension of acid XIV provides heptenoic acid XXIII, which after conversion into N-methoxy-N-methyl amide XXIV, can be reacted with an aryl organometallic reagent, such as an aryl magnesium bromide, to provide ketone XXV. Routine oxidative cleavage then gives the desired aldehyde XXVI, which can be coupled with an appropriate amine as described above.

Alcohol containing compounds are prepared according to procedures given in Scheme 7. Formation of the N-methyl-N-methoxy amide of acid VII followed by oxidative cleavage of the olefin provides intermediate aldehyde XXVII. Coupling with an appropriate amine provides amide XXVIII. Addition of an organometallic reagent to compound XXVIII provides illustrated ketone XXIX. Treatment with a hydride reducing agent, such as sodium borohydride, then yields the desired alcohol XXX.

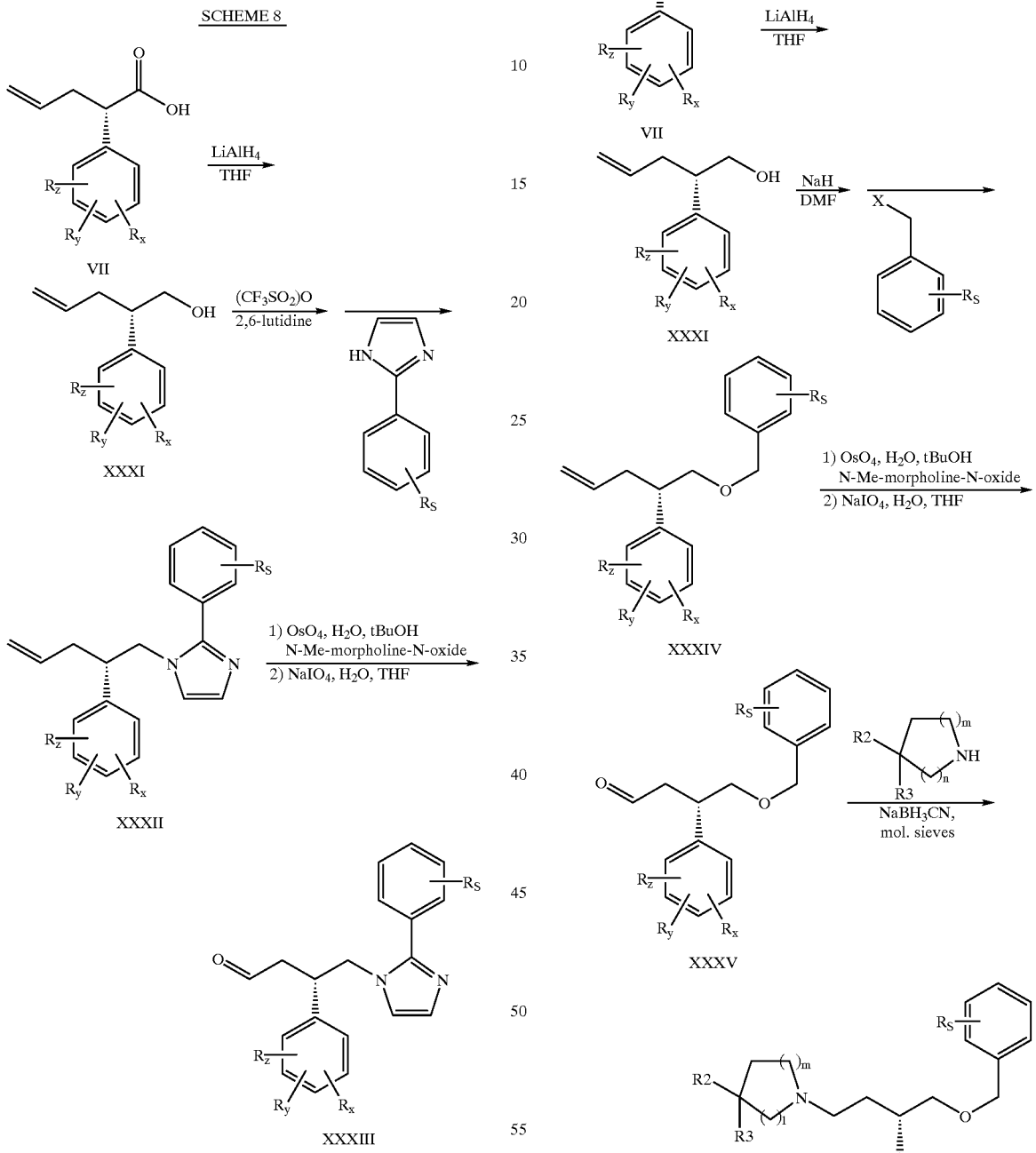

Formation of heterocycle compounds is carried out according to the procedure given in Scheme 8 for substituted imidazoles. Reduction of allyl acid VII with a strong reducing agent such as lithium aluminum hydride provides alcohol XXXI. In situ formation of the trifluoromethanesulfonate ester of the formed alcohol allows for displacement of the triflate with a nucleophile such as 2-phenylimidazole, to give imidazole XXXII. Oxidative cleavage under standard conditions provides the aldehyde XXXIII which can then be coupled under the conditions described above to the appropriate amine.

Compounds with ether substituents are prepared by the route shown in Scheme 9. Thus, allyl acid VII can be reduced to alcohol XXXI with, for example, lithium aluminum hydride. This alcohol can be alkylated by a Williamson ether synthesis, by deprotonation with a strong base such as sodium hydride or sodium hexamethyldisilazide followed by reaction with a benzyl halide such as benzyl bromide. The resulting ether XXXIV can be processed through the oxidative cleavage steps described earlier to provide aldehyde XXXV. This aldehyde can then be coupled with an appropriate amine under reductive amination conditions to give XXXVI. Alternatively, reduction of XXXV to the corresponding alcohol followed by conversion to the bromide allows for alkylation with an amine to provide XXXVI.

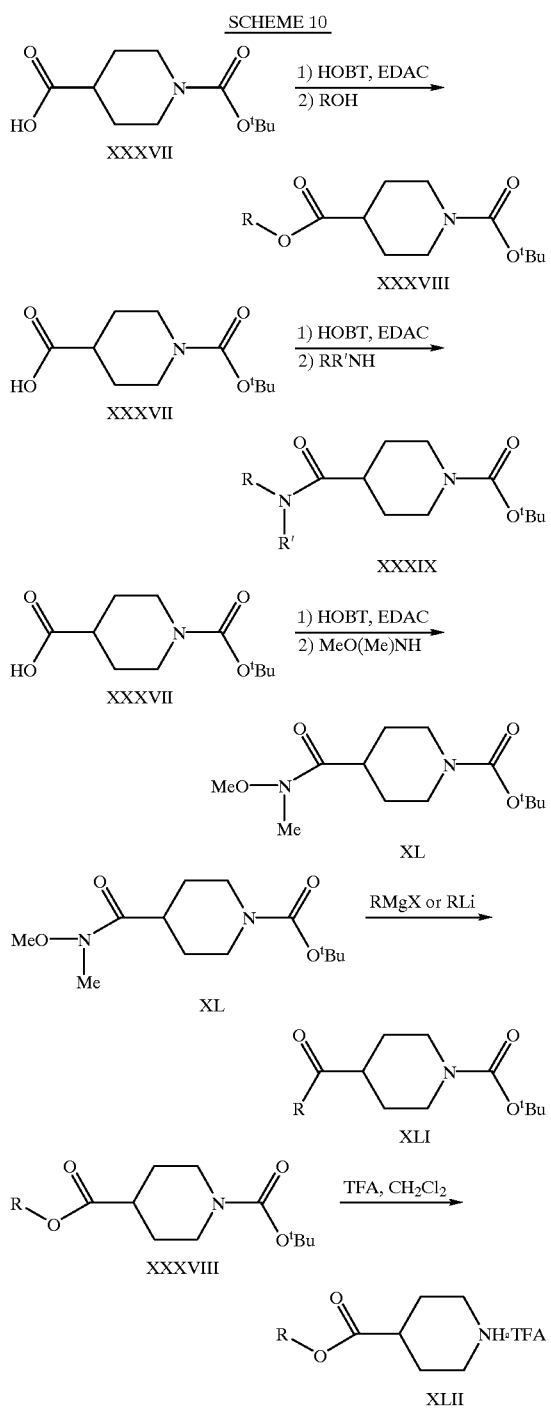

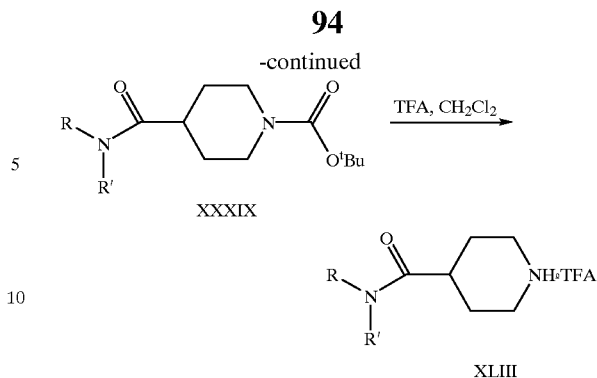

The substituted amines employed in the preceding Schemes can be obtained commercially in many cases or are prepared by a number of procedures. For example, as shown in Scheme 10, compound XXXVII, the N-t-butoxycarbonyl protected form of isonipecotic acid (4-piperidinecarboxylic acid) can be activated under standard conditions, for example with a carbodiimide, and converted into ester XXXVIII or amide XXXIX. Alternatively, acid XXXII can be converted into the N-methyl-N-methoxy amide, XL, which upon reaction with organomagnesium and organolithium reagents forms the ketone XLI. The Boc group of XXXVIII, XXXIX and XLI can be removed under acidic conditions to provide secondary amines XLII, XLIII and XLIV, respectively.

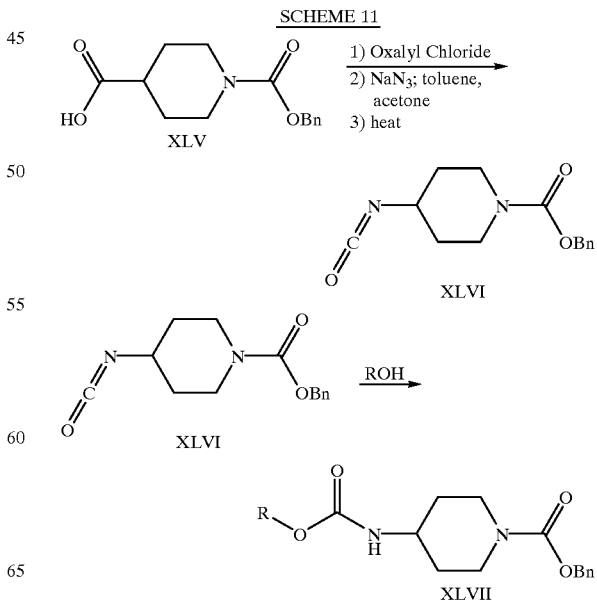

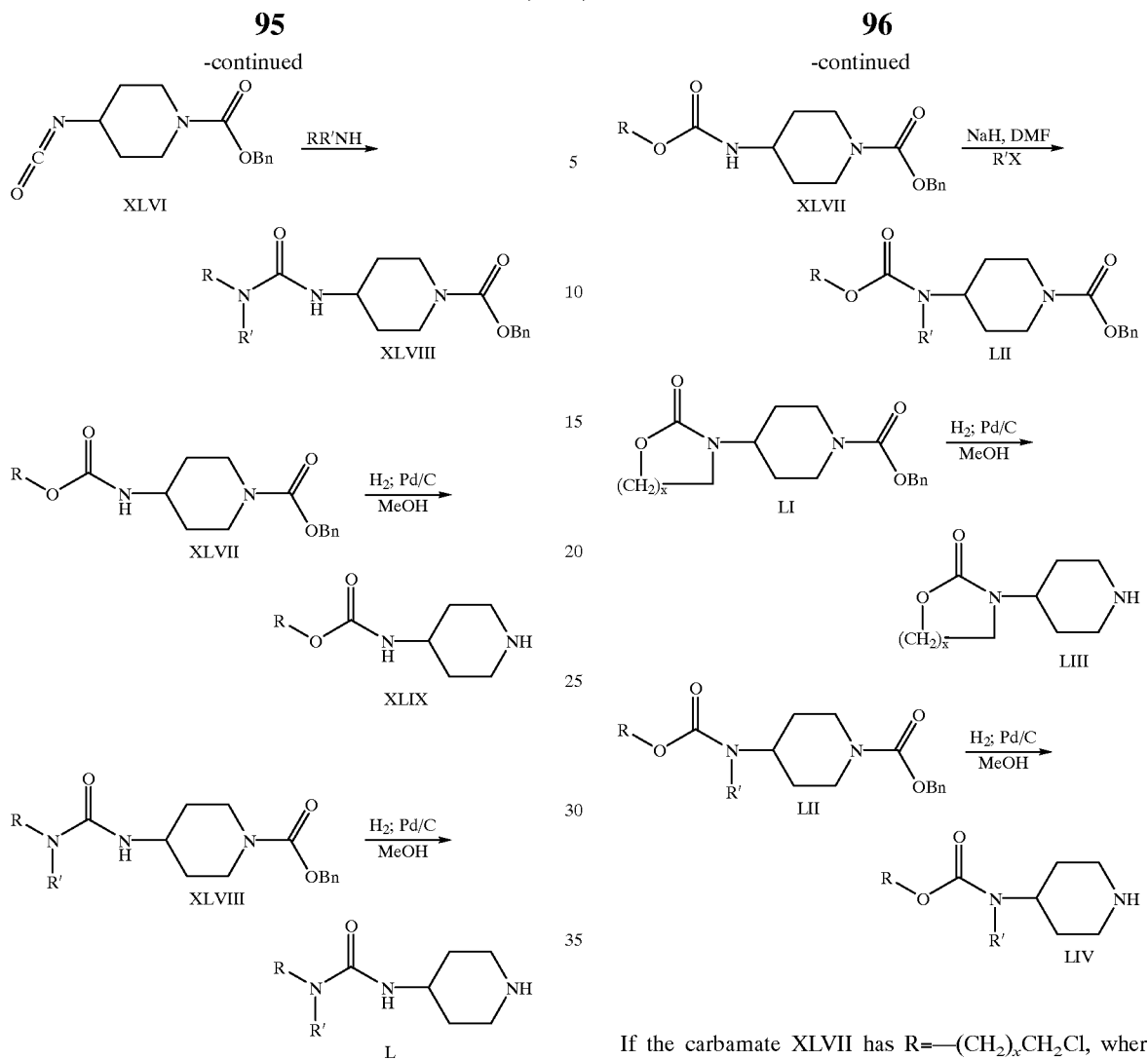

Alternatively, CBZ-protected piperidine XLV can be allowed to react with oxalyl chloride and then sodium azide, to provide the corresponding acyl azide, which can then be thermally rearranged to isocyanate XLVI (Scheme 11). Compound XLVI can be treated with an alcohol ROH or an amine RR'NH to form carbamate XLVII or urea XLVIII, respectively, each of which can be deprotected with hydrogen in the presence of palladium on carbon to secondary amines XLIX or L.

If the carbamate XLVII has R=—(CH$_2$)$_x$CH$_2$Cl, where x=1–3, then treatment with a suitable base, such as sodium hydride, lithium hexamethyldisilazide or potassium t-butoxide, can induce cyclization to compound LI (Scheme 12). For other R groups, carbamate XLVII can be treated with an alkylating agent R'X, where R'=primary or secondary alkyl, allyl, propargyl or benzyl, while X=bromide, iodide, tosylate, mesylate or trifluoromethanesulfonate, in the presence of a suitable base, such as sodium hydride, lithium hexamethyldisilazide or potassium t-butoxide, to give derivative LII. In each case, removal of the CBZ protecting group under standard conditions provides the secondary amines LIII and LIV.

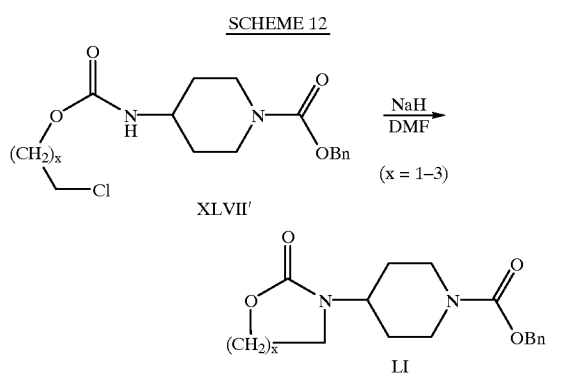

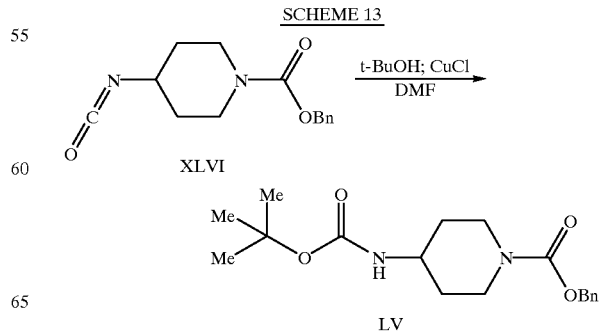

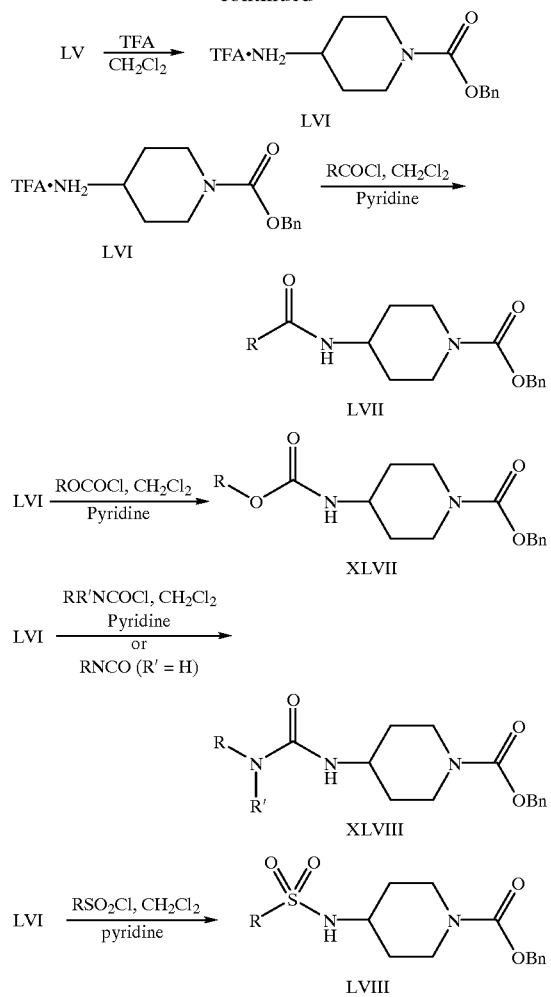

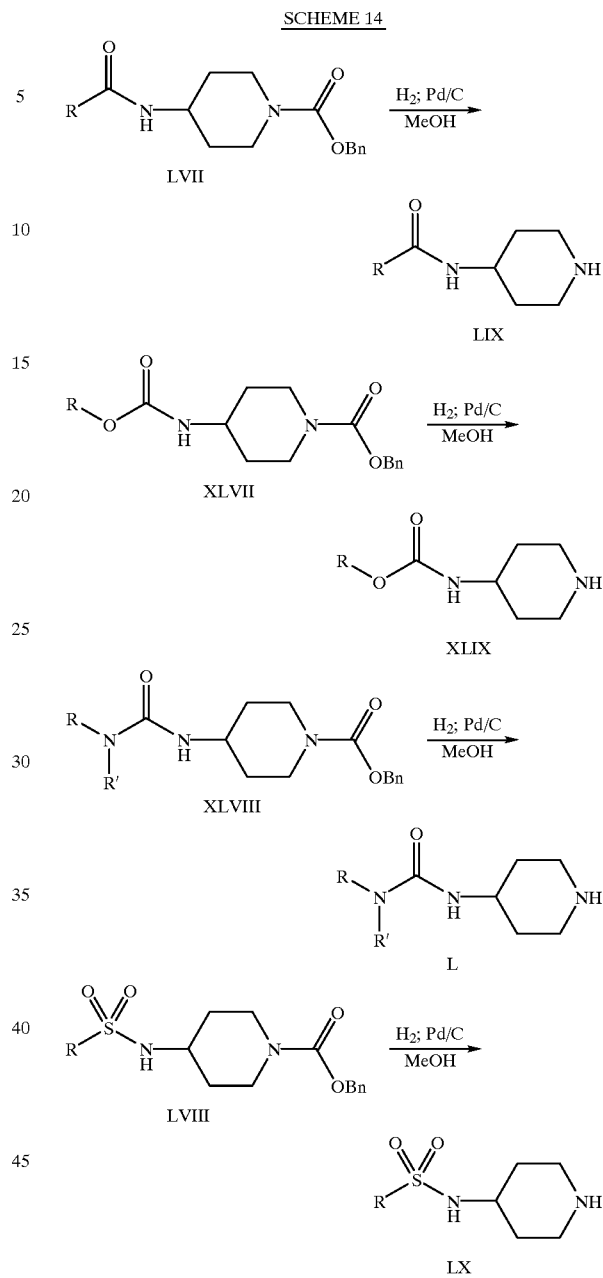

Additional derivatives of a piperidine with nitrogen functionality at C4 can be carried out as shown in Scheme 13. For example, if the ring nitrogen is protected with a CBZ group, as with isocyanate XLVI, treatment with tert-butyl alcohol in the presence of copper(I) chloride, provides Boc derivative LV. This compound can be selectively deprotected to the free amine LVI. This amine can be acylated with an acid chloride, a chloroformate, an isocyanate, or a carbamyl chloride, to provide compounds LVII, XLVII or XLVIII.

Alternatively, amine LVI can be sulfonated with an alkyl or arylsulfonyl chloride, to give sulfonamide LVIII.

In each case, removal of the CBZ group under reductive conditions gives the desired secondary amines LIX, XLIX, L, and LX (Scheme 14).

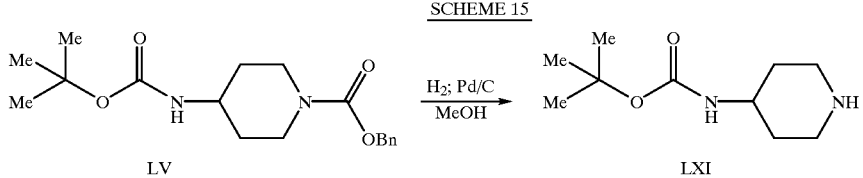

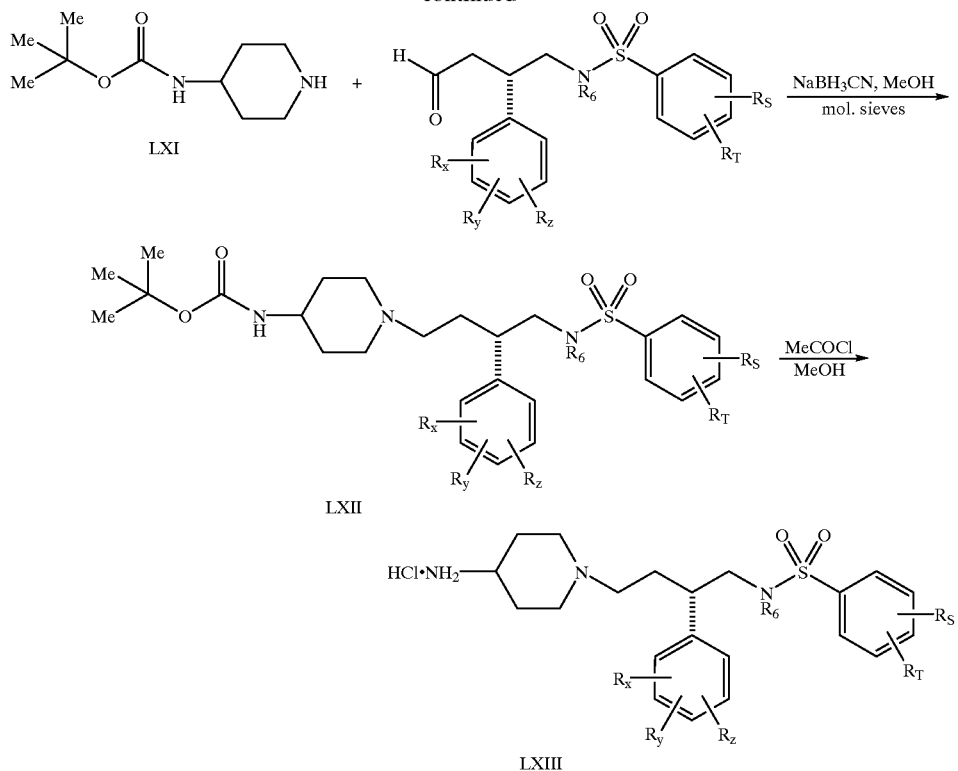

Functionalization of the piperidine can also be carried out after it has been coupled with an N1 substituent. For example, as shown in Scheme 15, reductive deprotection of CBZ derivative LV yields secondary amine LXI. Reductive amination with an appropriate aldehyde fragment (as described above) provides piperidine LXII. Removal of the Boc group under acidic conditions then gives primary amine LXIII. This primary amine can then be functionalized by analogy to the chemistry given in Scheme 13. Compound LXI can also be alkylated as described above in Scheme 12, and then carried through the remaining sequence given in Scheme 15.

SCHEME 16

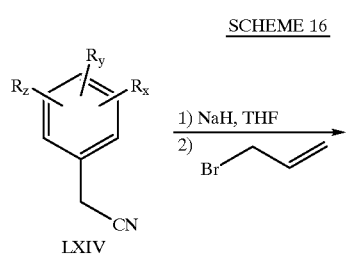

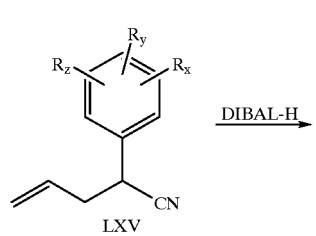

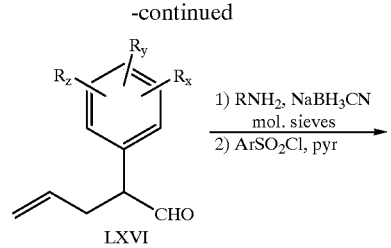

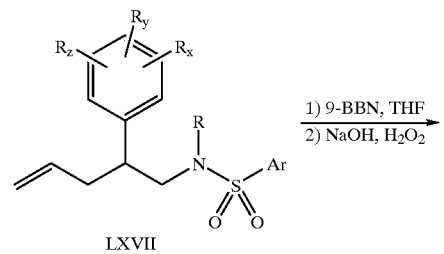

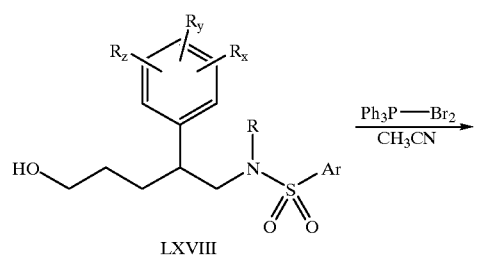

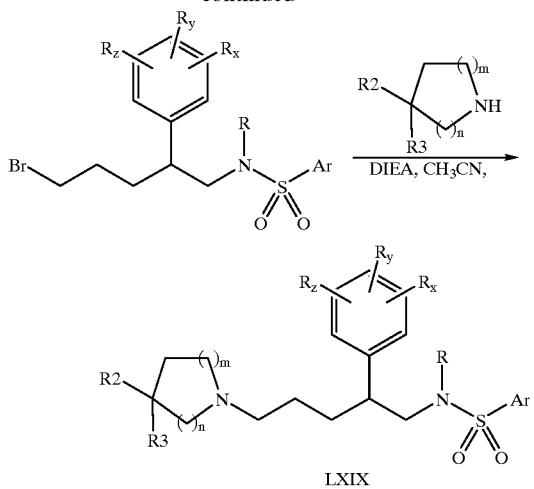

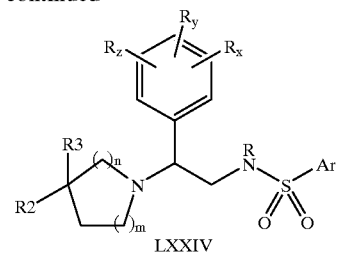

A method of preparing a backbone with an alternate spacing from the one described above is given in Scheme 16. Deprotonation of a suitable phenylacetonitrile derivative LXIV with sodium hydride followed by addition of allyl bromide provides the allyl nitrile LXV. Reduction to the corresponding aldehyde LXVI is carried out with diisobutylaluminum hydride in THF. Reductive amination with a primary amine followed by sulfonylation then provides sulfonamide LXVII. Selective hydroboration of the terminal position of the olefin, for example with 9-BBN, followed by oxidation with basic hydrogen peroxide, then gives primary alcohol LXVIII. Conversion of this alcohol to the corresponding bromide with triphenylphosphine-dibromide complex followed by alkylation with a cyclic secondary amine then gives the desired product LXIX.

Another backbone variation is prepared according to Scheme 17. Epoxidation of a suitably substituted styrene derivative LXX with an oxidizing agent such as mCPBA provides the epoxide LXXI which is converted to the aminoalcohol LXXII by treatment with a primary amine $RNH_2$. Treatment of LXXII with an acylating agent or a sulfonylating agent under mild conditions (as shown for the conversion to compound LXXIII) produces the corresponding neutral alcohol. Activation of the hydroxy group with, for example, methanesulfonyl chloride, followed by treatment with a secondary cyclic amine yields the aminosulfonamide LXXIV.

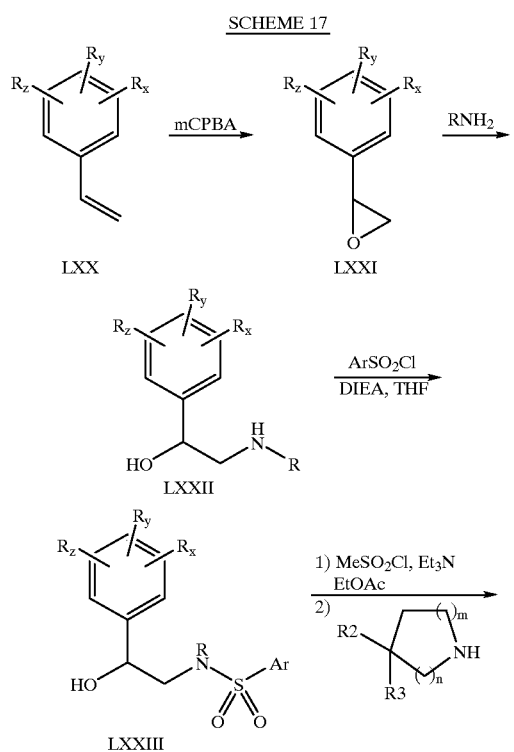

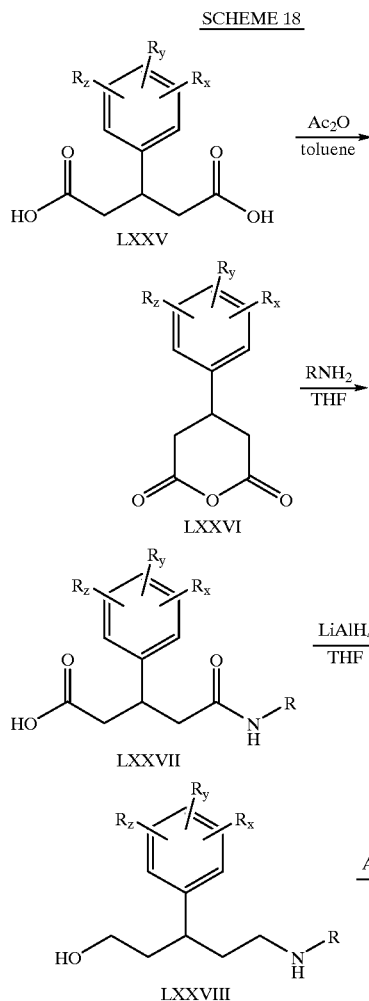

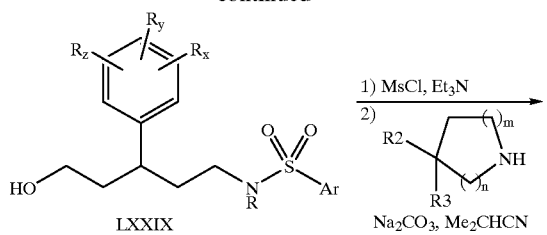

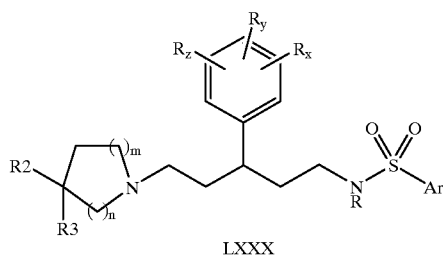

Another backbone variation is prepared according to Scheme 18. Treatment of 3-arylpentane-1,5-dioic acid LXXV with acetic anhydride in toluene provides anhydride LXXVI. Addition of an amine $RNH_2$ yields amidoacid LXXVII, which can be reduced with a strong reducing agent like lithium aluminum hydride to give aminoalcohol LXXVIII. Selective sulfonylation on nitrogen can be accomplished by treatment with a suitable arylsulfonyl chloride, to produce sulfonamide LXXIX. Activation of the hydroxy group with methanesulfonyl chloride in the presence of triethylamine followed by addition of a cyclic secondary amine in isobutyronitrile in the presence of sodium carbonate at elevated temperatures then provides the desired sulfonamidoamine LXXX.

SCHEME 19

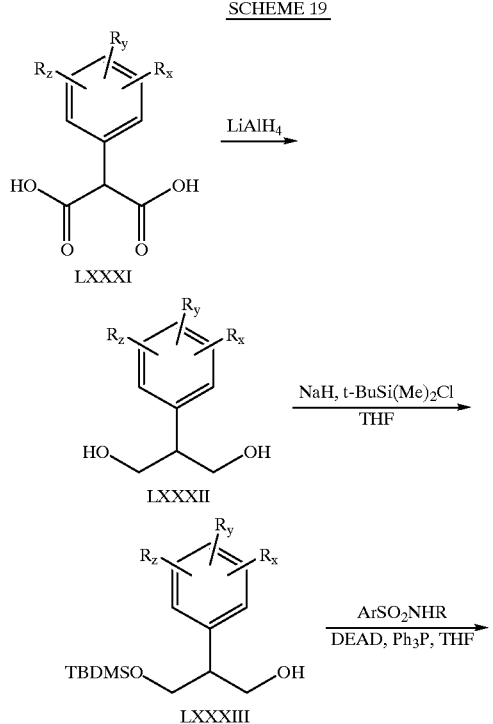

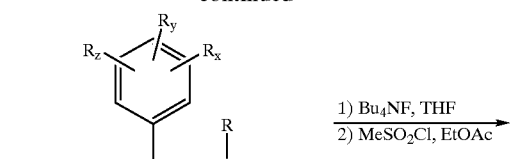

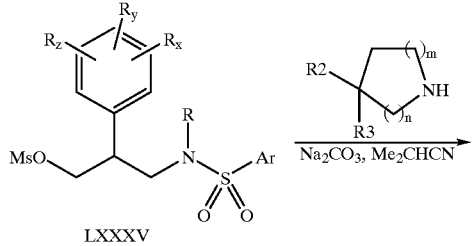

Another backbone variation is prepared according to Scheme 19. Reduction of 2-arylmalonic acid derivative LXXXI with lithium aluminum hydride provides diol LXXXII, which upon treatment with sodium hydride and t-butyldimethylsilyl chloride in THF produces selectively the monosilyl ether LXXXIII. Exposure of this compound to an N-substituted arylsulfonamide in the presence of DEAD and triphenylphosphine in THF provides the sulfonamide LXXXIV. Removal of the silyl group, for example with tetrabutylammonium fluoride in THF, followed by treatment with methanesulfonyl chloride in ethyl acetate, yields the mesylate LXXXV. Treatment of this mesylate with a cyclic secondary amine then provides the desired product LXXXVI.

SCHEME 20

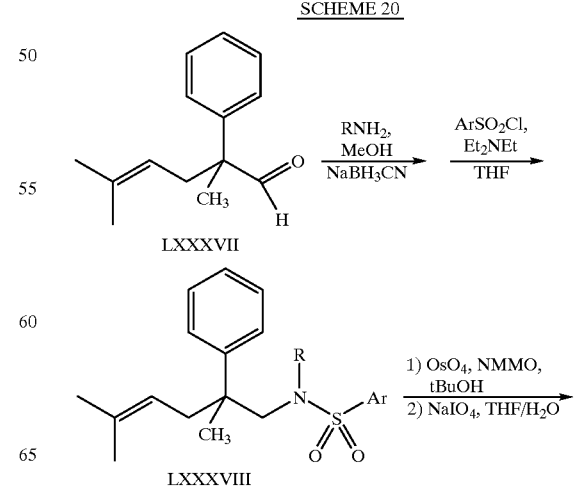

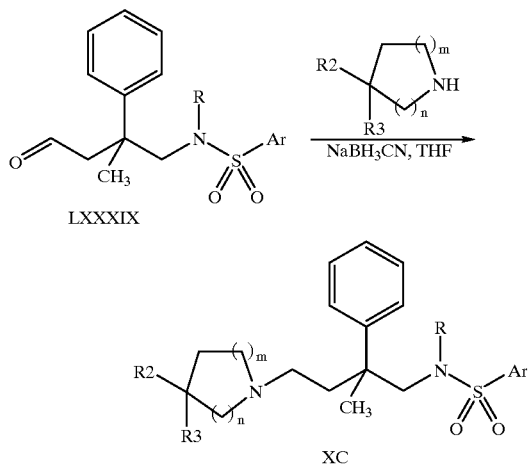

Another backbone variation is prepared according to Scheme 20. Reductive alkylation of the commercially available aldehyde LXXXVII with a suitable primary amine followed by sulfonylation provides sulfonamide LXXXVIII. Treatment of this olefin with osmium tetroxide followed by sodium periodate provides aldehyde LXXXIX. Reductive amination with a cyclic secondary amine then provides the target compound XC.

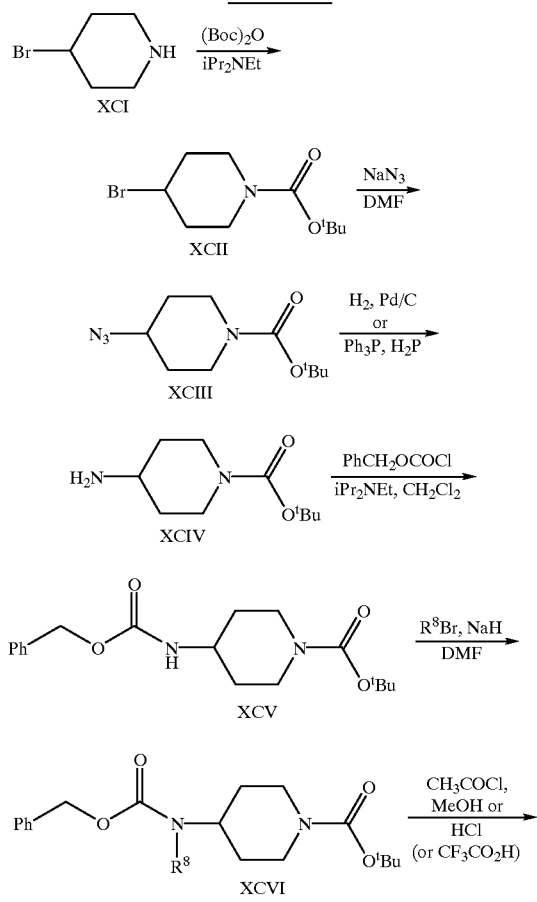

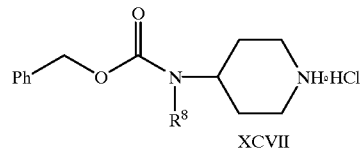

Additional derivatives of a piperidine with nitrogen functionality at C4 can be carried out as shown in Scheme 21. Treatment of commercially available 4 bromopiperidine XCI with a suitable nitrogen protecting agent, such as di-t-butyl pyrocarbonate, under standard conditions, provides protected piperidine XCII. Treatment with sodium azide (or another suitable salt of hydrazoic acid) in DMF at between room temperature and reflux provides the azide XCIII. Reduction of the azide under standard conditions, for example by catalytic hydrogenation with palladium on carbon or with triphenylphosphine and a proton source, provides primary amine XCIV, which can be employed in the same way as compound LVI (in Scheme 13) (subject to choosing functionality which is compatible with the conditions required for the removal of the t-butoxycarbonyl group). Alternatively, XCIV can be carried forward by acylation, for example with carbobenzyloxy chloride, to provide carbamate XCV. Alkylation of XCV under basic conditions with an alkylating agent containing a primary, secondary, allylic, propargylic, or benzylic leaving group, such as a chloride, bromide, iodide, or alkyl- or arylsulfonate ester, provides carbamate XCVI, which can be deprotected under standard acidic conditions to provide the piperidine XCVII.

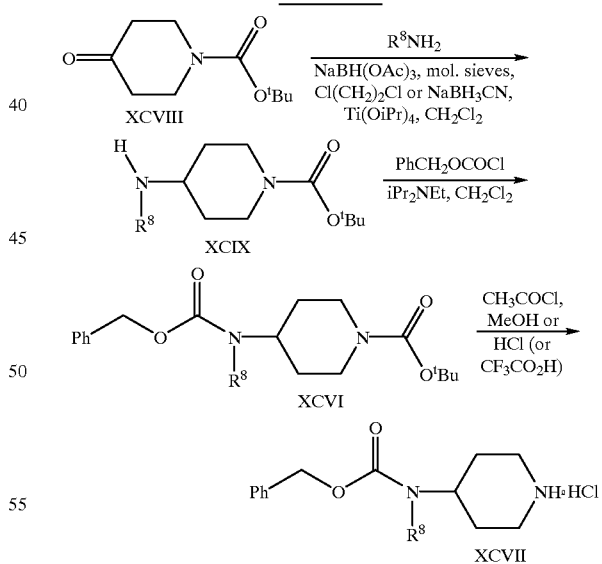

Additional derivatives of a piperidine with nitrogen functionality at C4 can be carried out as shown in Scheme 22. Reductive amination of N-Boc protected 4-piperidone XCVIII under standard conditions provides amine XCIX. Standard acylation can then be carried out, for example with carbobenzyloxy chloride, which provides XCVI. Removal of the Boc group under standard acidic conditions then provides piperidine XCVII.

SCHEME 23

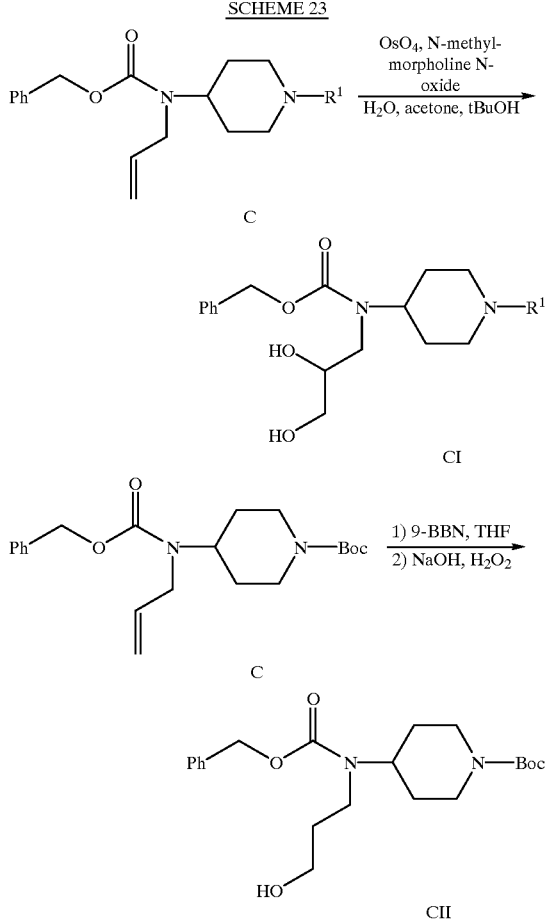

Refunctionalization of subunits on the carbamate group on the piperidine ring can also be carried out. For example, as shown in Scheme 23, the N-allyl carbamate C can be dihydroxylated with osmium tetroxide under standard conditions to provide diol CI. Compound C can also be converted to the primary alcohol CII by treatment with an appropriate hydroborating agent, such as 9-borabicyclononane, followed by oxidation with hydrogen peroxide or trimethylamine N-oxide.

In some cases the order of carrying out the foregoing reaction schemes may be varied to facilitate the reaction or to avoid unwanted reaction products.

The following examples are provided for the purpose of further illustration only and are not intended to be limitations on the disclosed invention.

EXAMPLE 1

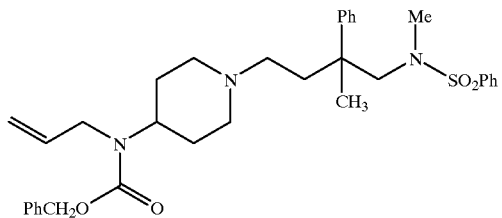

N-(4-(4-(N-(Benzyloxycarbonyl)allylamino) piperidin-1-yl)-2-methyl-2-phenylbutyl)-N-methylbenzenesulfonamide hydrochloride Step A: 4-Azido-1-(tert-butoxycarbonyl)piperidine To a solution of 45.3 g (172 mmol) of 4-bromo-1-(tert-butoxycarbonyl)piperidine in 750 mL of DMF was added 22.3 g (343 mmol) of sodium azide and 2.5 g (17 mmol) of sodium iodide. The reaction was stirred at RT for 24 h and then at 60° C. for 4 h. The mixture was poured into water containing 20 mL of sodium bicarbonate and extracted twice with 1:1 ether/hexane. The organic layers were each washed with a portion of water and brine, dried over sodium sulfate, combined and concentrated. The residue was purified by flash column chromatography, eluting with 5–10% ethyl acetate in hexane, to afford 39 g of title compound having a trace of elimination byproduct. $^1$H NMR (400 MHz, CDCl$_3$): δ 3.78 (m, 2H), 3.55 (m, 1H), 3.07 (m, 2H), 1.85 (m, 2H), 1.52 (m, 2H), 1.43 (s, 9H).

Step B: 4Amino-1-(tert-butoxycarbonyl)piperidine

A solution of 4.05 g (17.9 mmol) of 4-azido-1-(tert-butoxycarbonyl)piperidine from Step A in 50 mL of methanol was hydrogenated with 350 mg of 10% Pd/C under a hydrogen balloon for 16 h when the reaction was complete by TLC (10% ethyl acetate in hexane). The catalyst was filtered off and the volatiles removed in vacuo to give 3.5 g of title compound which was used directly in subsequent reactions.

Step C: 4-(Benzyloxycarbonylamino)-1-(tert-butoxycarbonyl)piperidine

To a solution of 1.2 g (6.0 mmol) 4-amino-1-(tert-butoxycarbonyl)piperidine from Step B in 40 mL of dichloromethane was added 3.15 mL (18 mmol) of N,N-diisopropylethylamine and 1.03 mL (7.2 mmol) of benzyl chloroformate while cooled in an ice bath. After 0.5 h the reaction was quenched with aqueous sodium carbonate and extracted three times with dichloromethane. The organic layers were each washed with a portion of brine, dried over sodium sulfate, combined and concentrated. The residue was purified by flash column chromatography, eluting with 25% ethyl acetate in hexane, to afford 1.94 g of title compound. $^1$H NMR (400 MHz, CDCl$_3$): δ 7.33 (m, 5H), 5.09 (s, 2H), 4.42 (bs, 1H), 4.08 (m, 2H), 3.58 (m, 1H), 2.90 (bt, 2H), 1.90 (bd, 2H, J=12 Hz), 1.42 (s, 9H), 1.26 (m, 2H).

Step D: 4-(N-(Benzyloxycarbonyl)allylamino)-1-(tert-butoxycarbonyl)piperidine

Sodium hydride (47 mg of 60% oil dispersion, 1.2 mmol) was added to a solution of 4-(benzyloxycarbonylamino)-1-(tert-butoxycarbonyl)piperidine (200 mg, 0.598 mmol) and allyl bromide (0.251 mL, 351 mg, 2.9 mmol) in 2.0 mL of DMF, and the reaction was stirred overnight at RT. The reaction mixture was poured into 20 mL of water and extracted with 3×20 mL of ethyl ether. The combined organic layers were washed with 30 mL of brine, dried over sodium sulfate, and evaporated. The crude product was purified by flash column chromatography on silica gel, eluting with 20% ethyl acetate in hexane, to give 246 mg of the title compound as a viscous oil. $^1$H NMR (400 MHz, CD$_3$OD): δ 7.38–7.26 (m, 5H), 5.81 (ddt, 1H, J=16, 10, 5 Hz), 5.18–5.05 (m, 4H), 4.12 (bd, 2H, J=12 Hz), 3.98 (bs, 1H), 3.86 (bd, 2H, J=5 Hz), 2.75 (bs, 2H), 1.74–1.63 (m, 4H). Mass spectrum (ESI): m/z=275 (M−99, 100%).

Step E: 4-(N-(Benzyloxycarbonyl)allylamino)piperidine hydrochloride

Acetyl chloride (0.467 mL, 516 mg, 6.57 mmol) was added to 2.0 mL of methanol at 0° C. and the mixture was stirred for 10 min to give a solution of HCl. 4-(N-(Benzyloxycarbonyl)allylamino)-1-(tert-butoxy-carbonyl)

piperidine (123 mg, 0.33 mmol) was then added and the resulting solution was stirred for 1 h at 0° C. and 1 h at RT. The solution was evaporated to give the title compound as a crystalline solid in quantitative yield. $^1$H NMR (400 MHz, CD$_3$OD): δ 7.39–7.28 (m, 5H), 5.84 (ddt, 1H, J=17, 10, 5 Hz), 5.21–5.10 (m, 4H), 4.10–3.98 (m, 1H), 3.90 (d, 2H, J=5 Hz), 3.43 (bd, 2H, J=13 Hz), 3.04 (bt, 2H, J=13 Hz), 2.18–2.02 (m, 2H), 1.93 (d, 2H, J=13 Hz). Mass spectrum (CI): m/z=275 (M+1, 100%).

Step F: N-Methyl-(2,5-dimethyl-2-phenylhex-4-en-1-yl) amine

Methylamine hydrochloride (500 mg, 7.41 mmol), triethylamine (1.00 mL, 725 mg, 7.17 mmol), and 3 Å molecular sieve pellets (1.05 g) were added to a stirred solution of 2,5-dimethyl-2-phenylhex-4-enal (500 mg, 2.47 mmol) in 5.0 mL of methanol at RT. After 1 h, the mixture was cooled in an ice bath and acetic acid (0.29 mL, 0.30 g, 5.1 mmol) was added followed by sodium cyanoborohydride (310 mg, 4.93 mmol). The mixture was allowed to slowly come to RT and stirred 16 h before being diluted with ethyl acetate (50 mL) and washed with saturated aqueous sodium bicarbonate (30 mL) and saturated aqueous sodium chloride (30 mL). The aqueous layers were extracted with ethyl acetate (30 mL) and the combined organic layers were dried over sodium sulfate and evaporated. The residue was purified by flash column chromatography on silica gel, eluting with 5% methanol in ethyl acetate to give 415 mg the title compound. $^1$H NMR (400 MHz, CD$_3$OD): δ 7.36–7.28 (m, 4H), 7.18 (t, 1H, J=7 Hz), 4.88 (t, 1H, J=7.5 Hz), 2.87 (d, 1H, J=12 Hz), 2.66 (d, 1H, J=12 Hz), 2.39 (dd, 1H, J=14, 7.5 Hz), 2.30 (dd, 1H, J=14, 8 Hz), 2.27 (s, 3H), 1.59 (s, 3H), 1.54 (s, 3H), 1.34 (s, 3H). Mass spectrum (NH$_3$/CI): m/z=218 (M+1).

Step G: N-Methyl-N-(2,5-dimethyl-2-phenylhex-4-en-1-yl) benzenesulfonamide

Benzenesulfonyl chloride (0.280 mL, 388 mg, 2.19 mmol) was added dropwise over 5 min to a solution of N-methyl-(2,5-dimethyl-2-phenylhex-4-en-1-yl)amine (415 mg, 1.91 mmol) and N,N-diisopropylethylamine (0.520 mL, 386 mg, 2.99 mmol) in THF (5.0 mL) at RT. After 16 h, the reaction mixture was diluted with 30 mL of ethyl acetate and washed with 15 mL each of 2 N aqueous HCl, saturated aqueous sodium bicarbonate, and saturated aqueous sodium chloride. The organic layer was dried over sodium sulfate and evaporated. The crude product was purified by flash column chromatography on silica gel, eluting with 4% ethyl acetate in hexane, to give 0.59 g of the title compound as a colorless oil. $^1$H NMR (400 MHz, CDCl$_3$): δ 7.72 (d, 2H, J=7.5 Hz), 7.55 (t, 1H, J=7.5 Hz), 7.48 (t, 2H, J=7.5 Hz), 7.33–7.23 (m, 4H), 7.17 (t, 1H, J=7 Hz), 4.83 (bt, 1H, J=7 Hz), 3.40 (d, 1H, J=13 Hz), 2.94 (d, 1H, J=13 Hz), 2.50 (dd, 1H, J=15, 6 Hz), 2.33 (dd, 1H, J=15, 8 Hz), 2.09 (s, 3H), 1.59 (s, 6H), 1.42 (s, 3H). Mass spectrum (NH$_3$/CI): m/z= 358 (M+1).

Step H: N-Methyl-N-(2-methyl-2-phenyl-4-oxobutyl) benzenesulfonamide tert-Butanol (1.5 mL) and water (0.75 mL) were added to a solution of N-methyl-N-(2,5-dimethyl-2-phenylhex-4-en-1-yl)benzenesulfonamide (138 g, 0.386 mmol) in acetone (3.0 mL). A tert-butanol solution containing 2.5% osmium tetroxide (0.068 mL, 55 mg, 0.0054 mmol) was added, followed by 4-methylmorpholine N-oxide (200 mg, 1.70 mmol). The reaction was stirred at RT for 18 h and was then quenched with 1.5 mL of saturated aqueous sodium bisulfite and concentrated in vacuo. The residue was diluted with 10 mL of water and extracted with 3×15 mL of dichloromethane. The combined organic layers were washed with 10 mL of brine, dried over sodium sulfate, and evaportated to give 166 mg of the crude diol intermediate as a white foam.

A portion of the crude intermediate diol (77 mg, 0.197 mmol) was dissolved in 1.0 mL of THF. Water (0.30 mL) was added followed by sodium periodate (47 mg, 0.22 mmol), and the resulting mixture was stirred overnight at RT. The mixture was partitioned between 10 mL of ethyl acetate and a solution of 10 mL of water and 5 mL of brine. The aqueous layer was extracted with 2×10 mL of ethyl acetate, and the combined organic layers were washed with 20 mL of brine, dried over sodium sulfate, and evaporated to give the title compound as 58 mg of colorless film. $^1$H NMR (400 MHz, CDCl$_3$): δ 9.62 (t, 1H, J=2.5 Hz), 7.74 (d, 2H, J=7.5 Hz), 7.59 (t, 1H, J=7.5 Hz), 7.52 (t, 2H, J=7.5 Hz), 7.40–7.32 (m, 4H), 7.28–7.23 (m, 1H), 3.23 (d, 1H, J=13 Hz), 3.19 (dd, 1H, J=16, 2.5 Hz), 3.15 (d, 1H, J=13 Hz), 2.78 (dd, 1H, J=16, 2.5 Hz), 2.21 (s, 3H), 1.64 (s, 3H). Mass spectrum (ESI): m/z=332 (M+1).

Step I: N-(4-(4-(N-(Benzyloxycarbonyl)allylamino) piperidin-1-yl)-2-methyl-2-phenylbutyl)-N-methylbenzenesulfonamide hydrochloride N-Methyl-N-(2-methyl-2-phenyl-4-oxobutyl) benzenesulfonamide (50 mg, 0.15 mmol), 4-(N-(benzyloxycarbonyl)allylamino)-piperidine hydrochloride (52 mg, 0.17 mmol), and N,N-diisopropylethyl-amine (0.042 mL, 31 mg, 0.24 mmol) were combined in 2.0 mL of 1,2-dichloroethane with 3 Å molecular sieve pellets (0.5 g). After 20 minutes, sodium triacetoxyborohydride (64 mg, 0.30 mmol) was added and the mixture was stirred at RT overnight. The reaction mixture was partitioned between 15 mL of ethyl acetate and 10 mL of saturated aqueous sodium bicarbonate, and the aqueous layer was extracted with 15 mL of ethyl acetate. The combined organic layers were washed with 15 mL of brine, dried over sodium sulfate, and evaporated. The residue was purified by flash column chromatography, eluting with 30–50% ethyl acetate in hexane, to give 72 mg of the free base corresponding to the title compound. The enantiomers of the free base could be separated by preparative HPLC on a Chiracel OD column, eluting with 20% isopropanol in hexane. $^1$NMR (400 MHz, CD$_3$OD): δ 7.74 (d, 2H, J=8 Hz), 7.63 (t, 1H, J=8 Hz), 7.56 (t, 2H, J=8 Hz), 7.41–7.27 (m, 9H), 7.21 (t, 1H, J=7 Hz), 5.80 (ddt, 1H, J=17, 10, 5 Hz), 5.16–5.04 (m, 4H), 3.96–3.80 (m, 1H), 3.84 (d, 2H, J=5 Hz), 3.39 (d, 1H, J=14 Hz), 3.04–2.88 (m, 2H), 3.00 (d, 1H, J=14 Hz), 2.36–2.24 (m, 1H), 2.20 (dt, 1H, J=13, 3 Hz), 2.10 (s, 3H), 2.04–1.88 (m, 3H), 1.86–1.72 (m, 3H), 1.70–1.60 (m, 2H), 1.46 (s, 3H). Mass spectrum (ESI): m/z=590 (M+1, 100%).

The free base was dissolved in methanol and treated with a small excess of aqueous HCl. Removal of the solvent at reduced pressure gave the title compound. $^1$NMR (400 MHz, CD$_3$OD): δ 7.78 (d, 2H, J=7 Hz), 7.66 (t, 1H, J=7 Hz), 7.59 (d, 2H, J=7 Hz), 7.47–7.24 (m, 10H), 5.83 (ddt, 1H, J=17, 10, 5 Hz), 5,21–5.05 (m, 4H), 4.10–3.97 (m, 1H), 3.90 (d, 2H, J=5 Hz), 3.60 (bt, 2H, J=11 Hz), 3.20–2.93 (m, 4H), 2.75 (td, 1H, J=13, 4 Hz), 2.50 (td, 1H, J=13, 4 Hz), 2.30–2.20 (m, 3H), 2.16 (s, 3H), 2.01–1.91 (m, 2H), 1.48 (s, 3H).

EXAMPLE 2

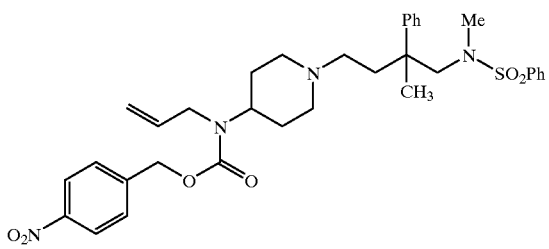

(R)- or (S)-N-Methyl-N-(4-(2-methyl-4-(N-(4-nitrobenzyloxycarbonyl)-allylamino)piperidin-1-yl)-2-phenylbutyl)-benzenesulfonamide hydrochloride Step A: 1-(tert-Butoxycarbonyl)-4-(N-(4-nitrobenzyloxycarbonyl)-allylamino)piperidine Allylamine (0.45 mL, 0.34 g, 6.0 mmol), acetic acid (0.300 mL, 315 mg, 5.24 mmol), and 3 A molecular sieves (2.00 g) were added to a solution of 1-(tert-butyoxycarbonyl)-4-piperidone (1.00 g, 5.01 mmol) in 14 mL of 1,2-dichloroethane. After stirring 0.5 h at RT, sodium triacetoxyborohydride (1.62 g, 7.6 mmol) was added in two portions 5 min apart. After an additional 3 h, the mixture was partitioned between 30 mL of ethyl acetate and 20 mL of saturated aqueous sodium bicarbonate. The aqueous layer was extracted with 30 mL of ethyl acetate and the organic layers were washed in succession with 20 mL of brine, combined, dried over sodium sulfate, and evaporated to give 1.20 g of crude 4-(allylamino)-1-(tert-butoxycarbonyl) piperidine as a yellow syrup.

A portion of the crude 4-(allylamino)-1-(tert-butoxycarbonyl)piperidine (400 mg, 1.66 mmol) was dissolved in 10 mL of dichloromethane and treated with N,N-diisopropylethylamine (0.700 mL, 519 mg, 4.0 mmol) and 4-nitrobenzyl chloroformate (392 mg, 1.82 mmol). After stirring 3 h at RT, the mixture was diluted with 30 mL of ethyl acetate and washed with 15 mL each of 2 N aqueous HCl, saturated aqueous sodium bicarbonate, and brine. The organic layer was dried over sodium sulfate, and evaporated. The residue was purified by flash column chromatography on silica gel, eluting with 30% ethyl acetate in hexane, to give 572 mg of the title compound as a colorless syrup. $^1$H NMR (400 MHz, CDCl$_3$): δ 8.22 (d, 2H, J=8 Hz), 7.50 (d, 2H, J=8 Hz), 5.80 (ddt, 1H, J=17, 10, 5 Hz), 5.23 (s, 2H), 5.18–5.09 (m, 2H), 4.27–4.08 (m, 3H), 3.89–3.79 (m, 2H), 2.79–2.66 (m, 2H), 1.74–1.52 (m, 4H), 1.46 (s, 9H). Mass spectrum (ESI): m/z=420 (M+1, 27%), 437 (M+1+NH$_3$, 100%).

Step B: 4-(N-(4-Nitrobenzyloxycarbonyl)allylamino) piperidine hydrochloride

The title compound was prepared according to the procedure of Example 1 (Step E), replacing 4-(N-(benzyloxycarbonyl)allyl-amino)-1-(tert-butoxycarbonyl) piperidine with 1-(tert-butoxycarbonyl)-4-(N-(4-nitrobenzyloxycarbonyl)allylamino)piperidine. $^1$H NMR (400 MHz, CD$_3$OD): δ 8.24 (d, 2H, J=8 Hz), 7.60 (d, 2H, J=8 Hz), 5.87 (ddt, 1H, J=17, 10, 5 Hz), 5.27 (s, 2H), 5.23–5.13 (m, 2H), 4.14–3.94 (m, 1H), 3.94 (d, 2H, J=5 Hz), 3.45 (d, 2H, J=13 Hz), 3.06 (t, 2H, J=13 Hz), 2.20–2.03 (m, 2H), 2.02–1.90 (m, 2H). Mass spectrum (ESI): m/z=320 (M+1, 93%).

Step C: (R)- or (S)-N-Methyl-N-(4-(2-methyl-4-(N-(4-nitrobenzyloxycarbonyl)allylamino)piperidin-1-yl)-2-phenybutyl)-benzenesulfonamide hydrochloride Racemic N-methyl-(2,5-dimethyl-2-phenylhex-4-en-1-yl)amine, from Example 1 (Step F), was dissolved in ethyl ether (13 mL/g) and (R)-mandelic acid (0.6 equiv.) was added. The solution was seeded and stored overnight at 0° C. After filtration, the mother liquor was evaporated and the residue was partitioned between ethyl ether and 2.5 N aqueous sodium hydroxide. The organic layer was washed with brine, dried over sodium sulfate, and evaporated. The recovered amine was dissolved in ethyl ether (8 mL/g) and (S)-mandelic acid (0.7 equiv.) was added. The solution was seeded and stored overnight at 0° C. The crystals were separated by filtration and washed with 0° C. ethyl ether. The dried crystals were recrystallized twice by dissolving in warm THF (1.4–2.2 mL/g) and adding ethyl ether (4.4–5.5 mL/g) before seeding the solution and cooling to −20 to 0° C. The resulting white crystalline solid ([α]$_D$+56.6 (c=1.01, 95% ethanol)) was partitioned between ethyl ether and 2.5 N aqueous sodium hydroxide. The organic layer was washed with brine, dried over sodium sulfate, and evaporated to give N-methyl-(2,5-dimethyl-2-phenylhex-4-en-1-yl)amine enriched in one enantiomer.

The free base corresponding to the title compound was prepared according to the procedure of Example 1 (Steps G-I), using N-methyl-(2,5-dimethyl-2-phenylhex-4-en-1-yl) amine (resolved as described in the preceding paragraph) and substituting 4-(N-(4-nitrobenzyloxy-carbonyl) allylamino)piperidine hydrochloride (from Step B) for 4-(N-(benzyloxycarbonyl)allylamino)piperidine hydrochloride. Final purification was accomplished by preparative HPLC on a Chiracel OD column, eluting with 40% isopropanol in hexane. $^1$H NMR (400 MHz, CD$_3$OD): δ 8.03 (d, 2H, J=8 Hz), 7.75 (d, 2H, J=7 Hz), 7.64 (t, 1H, J=7 Hz), 7.60–7.54 (m, 4H), 7.39 (d, 2H, J=7 Hz), 7.32 (t, 2H, J=7 Hz), 7.21 (t, 1H, J=7 Hz), 5.89–5.78 (m, 1H), 5.24 (bs, 2H), 5.18–5.07 (m, 2H), 3.94–3.82 (m, 1H), 3.88 (bd, J=5 Hz), 3.39 (d, 1H, J=14 Hz), 3.04–2.96 (m, 2H), 2.93 (bd, 1H, J=11 Hz), 2.32 (td, 1H, J=12, 4 Hz), 2.20 (td, 1H, J=12, 4 Hz), 2.10 (s, 3H), 2.04–1.61 (m, 8H), 1.46 (s, 3H). Mass spectrum (ESI): m/z=635 (M+1).

The free base was dissolved in methanol and treated with a small excess of aqueous HCl. Removal of the solvent at reduced pressure gave the title compound. $^1$H NMR (400 MHz, CD$_3$OD): δ 8.23 (d, 2H, J=8 Hz), 7.78 (d, 2H, J=7 Hz), 7.66 (t, 1H, J=7 Hz), 7.63–7.55 (m, 4H), 7.44 (d, 2H, J=7 Hz), 7.38 (t, 2H, J=7 Hz), 7.27 (t, 1H, J=7 Hz), 5.93–5.80 (m, 1H), 5.30–5.10 (m, 4H), 4.09–3.95 (m, 1H), 3.94 (bd, 2H, J=5 Hz), 3.67–3.56 (m, 2H), 3.32 (d, 1H, J=14 Hz), 3.20–2.94 (m, 3H), 3.14 (d, 1H, J=14 Hz), 2.76 (td, 1H, J=12, 4 Hz), 2.50 (td, 1H, J=12, 4 Hz), 2.31–2.09 (m, 3H), 2.16 (s, 3H), 2.04–1.92 (m, 2H), 1.49 (s, 3H).

EXAMPLE 3

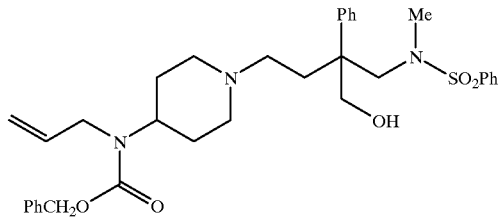

N-(4-(4-(N-(Benzyloxycarbonyl)allylamino) piperidin-1-yl)-2-(hydroxymethyl)-2-phenylbutyl)-N-methylbenzenesulfonamide hydrochloride Step A: 2-Phenyl-2-(2-(trimethylsilyl)ethoxymethyl)pent-4-enenitrile A solution of 2-phenylpent-4-enenitrile (199 mg, 1.27 mmol) in 3.0 mL of THF was cooled in an ice bath and a solution of 1.5 M lithium diisopropylamide mono (tetrahydrofuran) complex in cyclohexane (0.87 mL, 1.3 mmol) was added. After 15 min, the ice bath was removed and stirring was continued for 1 h at RT. The solution was cooled to −78° C., and 2-(trimethylsilyl)ethoxymethyl chloride (0.25 mL, 240 mg, 1.4 mmol) was added. After stirring 2 h with warming to 0° C., saturated aqueous ammonium chloride (10 mL) was added and the mixture was extracted with 25 mL of ethyl acetate. The organic layer was washed with 10 mL each of saturated aqueous sodium bicarbonate and brine, dried over sodium sulfate, and evaporated to give 362 mg of pale yellow oil. The crude title compound was used directly in subsequent reactions. $^1$H NMR (400 MHz, CDCl$_3$): δ 7.44 (d, 2H, J=7 Hz), 7.36 (t, 2H, J=7 Hz), 7.30 (t, 1H, J=7 Hz), 5.65 (ddt, 1H, J=17, 10, 7 Hz), 5.17–5.08 (m, 2H), 3.54 (t, 2H, J=8 Hz), 2.86 (dd, 1H, J=14, 7 Hz), 2.67 (dd, 1H, J=14, 7 Hz), 0.94–0.86 (m, 2H), −0.04 (s, 9H).

Step B: 2-Phenyl-2-(2-(trimethylsilyl)ethoxymethyl)pent-4-enal

A solution of 2-phenyl-2-(2-(trimethylsilyl) ethoxymethyl)-pent-4-enenitrile (354 mg, 1.23 mmol) in ethyl ether (1.0 mL) was cooled in an ice bath and a 1.5 M solution of diisobutylaluminum hydride in toluene (1.25 mL, 1.88 mmol) was added. After 2.5 h, ethyl acetate (0.30 mL, 270 mg, 3.1 mmol) was added and the mixture was transferred to a stirred mixture of 30 mL of ethyl ether and 10 mL of 2 N aqueous HCl at 0° C. After 10 min, the layers were separated and the aqueous layer was stirred for 0.5 h with another 30 mL of ethyl ether. The two organic layers were washed in succession with 10 mL each of 2 N aqueous HCl, saturated aqueous sodium bicarbonate, and brine. The combined organic layers were dried over sodium sulfate and evaporated. The residue was dissolved in 5.0 mL of THF and 0.7 mL of water was added followed by 1.0 g of silica gel. After stirring for 40 min at RT, the mixture was filtered and the silica gel was washed with additional THF. The filtrate was evaporated and the residue was purified by flash column chromatography on silica gel, eluting with 2% ethyl ether in hexane, to give 140 mg of the title compound as a colorless oil. $^1$H NMR (400 MHz, CDCl$_3$): δ 9.56 (s, 1H), 7.35 (t, 2H, J=7 Hz), 7.26 (t, 1H, J=7 Hz), 7.16 (d, 2H, J=7 Hz), 5.47 (ddt, 1H, J=17, 10, 7 Hz), 5.06–4.96 (m, 2H), 3.98 (d, 1H, J=9 Hz), 3.80 (d, 1H, J=9 Hz), 3.58–3.47 (m, 2H), 2.73 (d, 2H, J=7 Hz), 0.88 (t, 2H, J=8 Hz), −0.03 (s, 9 H). Mass spectrum (CI): m/z=263 (M−27, 100%).

Step C: N-Methyl-(2-phenyl-2-(2-(trimethylsilyl) ethoxymethyl)pent-4-en-1-yl)amine The title compound was prepared according to the procedure of Example 1 (Step F), replacing 2,5-dimethyl-2-phenylhex-4-enal with 2-phenyl-2-(2-(trimethylsilyl) ethoxymethyl)pent-4-enal. $^1$H NMR (400 MHz, CD$_3$OD): δ 7.46–7.18 (m, 5H), 5.48 (ddt, 1H, J=17, 10, 7 Hz), 5.00 (dm, 1H, J=17 Hz), 4.94 (dm, 1H, J=10 Hz), 3.76 (d, 1H, J=9 Hz), 3.66 (d; 1H, J=9 Hz), 3.64–3.52 (m, 2H), 2.93 (s, 2H), 2.51 (d, 2H, J=7 Hz), 2.31 (s, 3H), 0.93 (t, 2H, J=7 Hz), 0.00 (s, 9H).

Step D: N-Methyl-N-(2-phenyl-2-(2-(trimethylsilyl) ethoxymethyl)-pent-4-en-1-yl)benzenesulfonamide The title compound was prepared according to the procedure of Example 1 (Step G), replacing N-methyl-(2,5-dimethyl-2-phenylhex-4-en-1-yl)amine with N-methyl-(2-phenyl-2-(2-(trimethylsilyl)ethoxymethyl)pent-4-en-1-yl) amine. $^1$H NMR (400 MHz, CDCl$_3$): δ 7.73 (d, 2H, J=7 Hz), 7.56 (t, 1H, J=7 Hz), 7.49 (t, 2H, J=7 Hz), 7.36 (d, 2H, J=7 Hz), 7.30 (t, 2H,m J=7 Hz), 7.20 (t, 1H, J=7 Hz), 5.64–5.53 (m, 1H), 5.08 (dm, 2H, J=17 Hz), 4.98 (dm, 1H, J=10 Hz), 3.78 (d, 1H, J=10 Hz), 3.66 (d, 1H, J=10 Hz), 3.65–3.52 (m, 2H), 3.53 (d, 1H, J=14 Hz), 3.04 (d, 1H, J=14 Hz), 2.75 (dd, 1H, J=14, 6 Hz), 2.60 (dd, 1H, J=14, 8 Hz), 2.25 (s, 3H), 0.95 (t, 2H, J=8 Hz), 0.00 (s, 9H). Mass spectrum (ESI): m/z=445 (M+1, 28%).

Step E: N-Methyl-N-(4-oxo-2-phenyl-2-(2-(trimethylsilyl)ethoxy-methyl)butyl)benzenesulfonamide tert-Butanol (8.0 mL) and water (4.0 mL) were added to a solution of N-methyl-N-(2-phenyl-2-(2-(trimethylsilyl) ethoxymethyl)pent-4-en-1-yl)benzenesulfonamide (1.65 g, 3.70 mmol) in acetone (16 mL). 4-Methylmorpholine N-oxide (868 mg, 7.41 mmol) was added, followed by a tert-butanol solution containing 2.5% osmium tetroxide (0.70 mL, 0.57 g, 0.056 mmol). After stirring overnight at RT, the reaction was quenched by the addition of 5.7 mL of saturated aqueous sodium bisulfite and stirred for 10 min. The mixture was partitioned between 100 mL of ethyl acetate and 50 mL of water. The organic layer was washed with 50 mL each of 2 N aqueous HCl, saturated aqueous sodium bicarbonate, and brine. The aqueous layers were extracted in succession with 50 mL of ethyl acetate, and the combined organic layers were dried over sodium sulfate and evaporated. The residue was purified by flash column chromatography on silica gel, eluting with 40% ethyl acetate in hexane, to give 1.49 g of the intermediate diol.

A portion of the intermediate diol (64 mg, 0.13 mmol) was dissolved in 1.0 mL of THF. A solution of sodium periodate (36 mg, 0.17 mmol) in water (0.24 mL) was added and the resulting mixture was stirred for 1.5 h at RT. The mixture was partitioned between 20 mL of ethyl acetate and 10 mL of water. The organic layer was washed with 10 mL of brine, and the aqueous layers were then extracted in succession with 20 mL of ethyl acetate. The combined organic layers were dried over sodium sulfate and evaporated to give the title compound as 58 mg of colorless syrup. $^1$H NMR (400 MHz, CDCl$_3$): δ 9.58 (t, 1H, J=2 Hz), 7.72 (d, 2H, J=7 Hz), 7.57 (t, 1H, J=7 Hz), 7.50 (t, 2H, J=7 Hz), 7.37–7.30 (m, 2H), 7.27–7.12 (m, 1H), 3.95 (d, 1H, J=10 Hz), 3.79 (d, 1H, J=10 Hz), 3.59–3.48 (m, 2H), 3.31 (dd, 1H, J=17, 2 Hz), 2.88 (dd, 1H, J=17, 2 Hz), 2.18 (s, 3H), 0.93–0.85 (m, 2H), −0.03 (s, 9H). Mass spectrum (NH$_3$/CI): m/z=420 (M−27, 20%).

Step F: N-(4-(4-(N-(Benzyloxycarbonyl)allylamino) piperidin-1-yl)-2-(2-(trimethylsilyl)ethoxymethyl)-2-phenylbutyl)-N-methylbenzenesulfonamide The title compound was prepared according to the procedure of Example 1 (Step I), replacing N-methyl-N-(2-methyl-2-phenyl-4-oxobutyl)benzenesulfonamide with N-methyl-N-(4-oxo-2-phenyl-2-(2-(trimethylsilyl) ethoxymethyl)butyl)benzenesulfonamide. $^1$H NMR (400 MHz, CD$_3$OD): δ 7.74 (d, 2H, J=8 Hz), 7.64 (t, 1H, J=8 Hz), 7.57 (t, 2H, J=8 Hz), 7.40–7.26 (m, 9H), 7.22 (t, 1H, J=7 Hz), 5.81 (ddt, 1H, J=17, 10, 5 Hz), 5.18–5.04 (m, 4H), 3.96–3.81 (m, 4H), 3.73–3.55 (m, 3H), 3.48 (d, 1H, J=14 Hz), 3.05 (d, 1H, J=14 Hz), 3.02 (bd, 1H, J=10 Hz), 2.93 (bd, 1H, J=10 Hz), 2.37–2.27 (m, 1H), 2.20–1.92 (m, 5H), 2.12 (s, 3H), 1.88–1.74 (m, 2H), 1.70–1.60 (m, 2H), 0.96 (t, 2H, J=8 Hz), 0.02 (s, 9H). Mass spectrum (ESI): m/z=706 (M+1, 100%).

Step G: N-(4-(4-(N-(Benzyloxycarbonyl)allylamino) piperidin-1-yl)-2-(hydroxymethyl)-2-phenylbutyl)-N-methylbenzene-sulfonamide hydrochloride Trifluoroacetic acid (1.5 mL) was added to a solution of N-(4-(4-(N-(benzyloxycarbonyl)allylamino)piperidin-1-yl)-2-(2-(trimethylsilyl)-ethoxymethyl)-2-phenylbutyl)-N-methylbenzenesulfonamide (34 mg, 0.048 mmol) in dichloromethane (1.5 mL). After stirring the solution 1 h at RT, the solvents were evaporated. The residue was dissolved in 20 mL of ethyl acetate and washed with 10 mL of saturated aqueous sodium bicarbonate followed by 10 mL of brine. The organic layer was dried over sodium sulfate and evaporated. The residue was purified by flash column chromatography on silica gel, eluting with 2% methanol in dichloromethane, to give the free base corresponding to the title compound in quantitative yield. The enantiomers of the free base could be separated by preparative HPLC on a Chiracel OD column, eluting with 40% isopropanol in hexane. $^1$H NMR (400 MHz, CD$_3$OD): δ 7.77 (d, 2H, J=7 Hz), 7.65 (t, 1H, J=7 Hz), 7.58 (t, 2H, J=7 Hz), 7.41–7.27 (m, 9H), 7.23 (t, 1H, J=7 Hz), 5.81 (ddt, 1H, J=17, 10, 5 Hz), 5.19–5.04 (m, 4H), 4.02 (d, 1H, J=11 Hz), 3.97–3.82 (m, 4H), 3.36 (d, 1H, J=14 Hz), 3.16–3.08 (m, 2H), 2.85 (db, 1H, J=11 Hz), 2.43–2.33 (m, 1H), 2.31–2.23 (m, 1H), 2.16–1.95 (m, 4H), 2.03 (s, 3H), 1.86–1.60 (m, 4H). Mass spectrum (ESI): m/z=606 (M+1, 100%).

The free base was dissolved in methanol and treated with a small excess of aqueous HCl. Removal of the solvent at reduced pressure gave the title compound. $^1$H NMR (400 MHz, CD$_3$OD): δ 7.80 (d, 2H, J=8 Hz), 7.68 (t, 1H, J=8 Hz), 7.61 (t, 2H, J=8 Hz), 7.45–7.26 (m, 10 H), 5.84 (ddt, 1H, J=17, 10, 5 Hz), 5.22–5.07 (m, 4H), 4.12–3.96 (m, 1H), 4.06 (d, 1H, J=12 Hz), 3.90 (d, 2H, J=5 Hz), 3.87 (d, 1H, J=12 Hz), 3.68–3.56 3.56 (m, 2H), 3.15 (td, 1H, J=12, 5 Hz), 3.10–2.95 (m, 3H), 2.44–2.07 (m, 4H), 2.15 (s, 3H), 1.97 (bd, 2H, J=13 Hz).

EXAMPLE 4

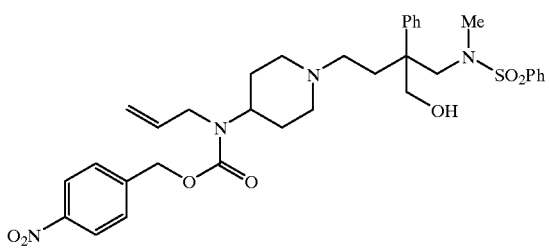

N-(2-(Hydroxymethyl)-4-(4-(N-(4-nitrobenzyloxycarbonyl)allylamino)-piperidin-1-yl)-2-phenylbutyl)-N-methylbenzenesulfonamide hydrochloride The free base corresponding to the title compound was prepared according to the procedure of Example 3 (Step F), substituting 4-(N-(4-nitrobenzyloxycarbonyl)allylamino) piperidine hydrochloride (from Example 2, Step B) for 4-(N-(benzyloxycarbonyl)allylamino)-piperidine hydrochloride. $^1$H NMR (400 MHz, CD$_3$OD): δ 8.23 (d, 2H, J=8 Hz), 7.77 (d, 2H, J=7 Hz), 7.65 (t, 1H, J=7 Hz), 7.62–7.55 (m, 4H), 7.40–7.31 (m, 4H), 7.23 (t, 1H, J=7 Hz), 5.90–5.78 (m, 1H), 5.24 (bs, 2H), 5.20–5.08 (m, 2H), 4.02 (d, 1H, J=12 Hz), 3.98–3.86 (m, 4H), 3.36 (d, 1H, J=14 Hz), 3.16–3.08 (m, 2H), 2.86 (bs, 1H, J=12 Hz), 2.42–2.33 (m, 1H), 2.31–2.23 (m, 1H), 2.16–1.96 (m, 4H), 2.03 (s, 3H), 1.89–1.62 (m, 4H). Mass spectrum (ESI): m/z=651 (M+1, 100%).

The free base was dissolved in methanol and treated with a small excess of aqueous HCl. Removal of the solvent at reduced pressure gave the title compound. $^1$H NMR (400 MHz, CD$_3$OD): δ 8.23 (d, 2H, J=8 Hz), 7.80 (d, 2H, J=7 Hz), 7.68 (t, 1H, J=7 Hz), 7.64–7.56 (m, 4H), 7.43–7.36 (m, 4H), 7.33–7.26 (m, 1H), 5.93–5.81 (m, 1H), 5.31–5.13 (m, 4H), 4.10–3.92 (m, 1H), 4.07 (d, 1H, J=12 Hz), 3.94 (bd, 1H, J=5 Hz), 3.87 (d, 1H, J=12 Hz), 3.69–3.58 (m, 2H), 3.16 (td, 1H, J=12, 5 Hz), 3.12–2.95 (m, 3H), 2.46–2.10 (m, 4H), 2.14 (s, 3H), 2.04–1.94 (m, 2H).

EXAMPLE 5

N-(4-(4-(N-(Benzyloxycarbonyl)allylamino) piperidin-1-yl)-2-(R,S)-phenylbutyl)-N-methylbenzenesulfonamide hydrochloride To a solution of N-(4-(4-(N-(benzyloxycarbonyl)amino)-piperidin-1-yl)-2-(R,S)-phenylbutyl)-N-methylbenzenesulfonamide (85 mg, 0.16 mmol) (prepared as described in Example 1, Step I and Examples 6–16 using 4-(N-benzyloxycarbonylamino)piperidine) in DMF (2 mL) at RT was added allyl bromide (0.042 mL, 0.49 mmol) and sodium hydride (32 mg, 0.81 mmol). After stirring for 16 hours, the reaction was quenched into a sat'd solution of sodium carbonate. The mixture was extracted with 3 portions of ether and the organic layers were successively washed with a portion of brine, dried over sodium sulfate, combined and concentrated in vacuo. The residue was purified by prep TLC (75% ethyl acetate in hexanes) to afford the free amine of title compound (67 mg). $^1$H NMR (400 MHz, CDCl$_3$): δ 1.5–2.4 (4 br. m, 12 H), 2.58 (s, 3 H), 2.8–3.1 (m, 3H), 3.38 (q, J=5 Hz, 1 H), 3.80 (m, 2 H), 4.56 (m, 1 H), 5.0–5.2 (m, 3 H), 5.78 (m, 1 H), 7.1–7.4 (m, 10 H), 7.4–7.5 (m, 2 H), 7.5–7.6 (m, 1 H), 7.79 (dd, J=1.5 and 5 Hz, 2 H).

The hydrochloride salt was prepared by dissolving the above product in ether, addition of an excess of hydrogen chloride in ether and evaporation to a white solid. Mass spectrum (MeOH/CI): m/z 576 (M+1, 100%).

EXAMPLES 6–16

Using essentially the same procedure as described in Example 1, Step I, but substituting the appropriate 4-aminopiperidine derivative (prepared as in Example 1, Steps D–E or Example 2, A–B) and racemic N-methyl-N-(2-phenyl-4-oxobutyl)benzenesulfonamide (prepared as described by J. Hale et al., *Bioorganic and Medicinal Chemistry Letters*, 1993, 3, 319–322 and Example 1, Step G), the following racemic compounds were prepared. (The chiral HPLC separation of the enantiomers was not done.)

EXAMPLE 6

N-(4-(4-(N-(Benzyloxycarbonyl)(pent-4-en-1-yl) amino)piperidin-1-yl)-2-(R,S)-phenylbutyl)-N-methylbenzenesulfonamide hydrochloride Mass spectrum (NH$_3$/CI): m/z 604 (M+1, 100%).

EXAMPLE 7

N-(4-(4-(N-(Benzyloxycarbonyl)(cyclobutylmethyl) amino)piperidin-1-yl)-2-(R,S)-phenylbutyl)-N-methylbenzenesulfonamide hydrochloride Mass spectrum (NH$_3$/CI): m/z 604 (M+1, 100%).

EXAMPLE 8

N-(4-(4-(N-(Benzyloxycarbonyl)(cyclohexylmethyl) amino)piperidin-1-yl)-2-(R,S)-phenylbutyl)-N-methylbenzenesulfonamide hydrochloride Mass spectrum (NH$_3$/CI): m/z 632 (M+1, 100%).

EXAMPLE 9

N-(4-(4-(N-(Benzyloxycarbonyl) (cyclopropylmethyl)amino)piperidin-1-yl)-2-(R,S)-phenylbutyl)-N-methylbenzenesulfonamide hydrochloride Mass spectrum (NH/CI): m/z 590 (M+1, 100%).

EXAMPLE 10

N-(4-(4-(N-(Benzyloxycarbonyl)(2-methoxyethyl) amino)piperidin-1-yl)-2-(R,S)-phenylbutyl)-N-methylbenzenesulfonamide hydrochloride Mass spectrum (ESI): m/z 594 (M+1, 100%).

EXAMPLE 11

N-4-(4-(N-Benzyloxycarbonyl)(2-fluoroethyl)
amino)piperidin-1-yl)-2-(R,S)-phenylbutyl)-N-
methylbenzenesulfonamide hydrochloride Mass spectrum (ESI): m/z 582 (M+1, 100%).

EXAMPLE 12

N-(4-(4-(N-(Benzyloxycarbonyl)(2-methoxymethyl)
amino)piperidin-1-yl)-2-(R,S)-phenylbutyl)-N-
methylbenzenesulfonamide hydrochloride Mass spectrum (ESI): m/z 536 (M+1, 100%).

EXAMPLE 13

N-(4-(4-(N-(Benzyloxycarbonyl)
(aminocarbonylmethyl)amino)piperidin-1-yl)-2-(R,
S)-phenylbutyl)-N-methylbenzenesulfonamide
hydrochloride Mass spectrum (ESI): m/z 593 (M+1, 100%).

EXAMPLE 14

N-(4-(4-(N-(Benzyloxycarbonyl)
(methoxycarbonylmethyl)amino)-piperidin-1-yl)-2-
(R,S)-phenylbutyl)-N-methylbenzenesulfonamide
hydrochloride Mass spectrum (ESI): m/z 608 (M+1, 100%).

EXAMPLE 15

N-(4-(4-(N-(Benzyloxycarbonyl)(propargyl)amino)
piperidin-1-yl)-2-(R,S)-phenylbutyl)-N-
methylbenzenesulfonamide hydrochloride Mass spectrum (ESI): m/z 574 (M+1, 100%).

EXAMPLE 16

N-(4-(4-(N-(4-Nitrobenzyloxycarbonyl)(allyl)amino)
piperidin-1-yl)-2-(R,S)-phenylbutyl)-N-
methylbenzenesulfonamide hydrochloride Mass spectrum (ESI): m/z 621 (M+1, 100%).

EXAMPLES 17–23

Using essentially the same procedure as described in Example 1, Step I, but substituting the appropriate 4-aminopiperidine derivative (prepared as in Example 1, Steps D–E or Example 2, A–B) and chiral N-methyl-N-(S)-2-phenyl-4-oxobutyl)benzenesulfonamide (prepared as described by J. Hale et al., *Bioorganic and Medicinal Chemistry Letters*, 1993, 3, 319–322 and Example 1, Step G), the following chiral compounds were prepared without need for chiral HPLC separation of enantiomers.

EXAMPLE 17

N-(4-(4-(N-(Benzyloxycarbonyl)(allyl)amino)
piperidin-1-yl)-2-(S)-phenylbutyl)-N-
methylbenzenesulfonamide hydrochloride Mass spectrum (ESI): m/z 576 (M+1, 100%).

EXAMPLE 18

N-(4-(4-(N-(Benzyloxycarbonyl)(propargyl)amino)
piperidin-1-yl)-2-(S)-phenylbutyl)-N-
methylbenzenesulfonamide hydrochloride Mass spectrum (ESI): m/z 574 (M+1, 100%).

EXAMPLE 19

N-(4-(4-(N-(Benzyloxycarbonyl)
(cyclopropylmethyl)amino)piperidin-1-yl)-2-(S)-
phenylbutyl)-N-methylbenzenesulfonamide
hydrochloride Mass spectrum (ESI): m/z 590 (M+1, 100%).

EXAMPLE 20

N-(4-(4-(N-(4-Nitrobenzyloxycarbonyl)(propargyl)
amino)piperidin-1-yl)-2-(S)-phenylbutyl)-N-
methylbenzenesulfonamide hydrochloride Mass spectrum (ESI): m/z 619 (M+1, 100%).

EXAMPLE 21

N-(4-(4-(N-(4-Nitrobenzyloxycarbonyl)
(cyanomethyl)amino)piperidin-1-yl)-2-(S)-
phenylbutyl)-N-methylbenzenesulfonamide
hydrochloride Mass spectrum (ESI): m/z 620 (M+1, 100%).

EXAMPLE 22

N-(4-(4-(N-(Benzyloxycarbonyl)(2-hydroxyethyl)
amino)piperidin-1-yl)-2-(S)-phenylbutyl)-N-
methylbenzenesulfonamide hydrochloride Mass spectrum (ESI): m/z 580 (M+1, 100%).

EXAMPLE 23

N-(4-(4-(N-(4-Nitrobenzyloxycarbonyl)(2-
hydroxyethyl)amino)piperidin-1-yl)-2-(S)-
phenylbutyl)-N-methylbenzenesulfonamide
hydrochloride Mass spectrum (ESI): m/z 625 (M+1, 100%).

EXAMPLES 24–32

Using essentially the same procedure as described in Example 1, Step I, but substituting the appropriate 4-aminopiperidine derivative (prepared as in Example 1, Steps D–E or Example 2, A–B) and chiral N-methyl-N-(S)-2-(3-chlorophenyl)-4-oxobutyl)benzenesulfonamide (prepared as described by J. Hale et al., *Bioorganic and Medicinal Chemistry Letters*, 1993, 3, 319–322 and Example 1, Step G), the following chiral compounds were prepared without need for chiral HPLC separation of enantiomers.

EXAMPLE 24

N-(4-(4-(N-(Benzyloxycarbonyl)
(cyclopropylmethyl)amino)piperidin-1-yl)-2-(S)-(3-
chlorophenyl)butyl)-N-methylbenzenesulfonamide
hydrochloride Mass spectrum (ESI): m/z 624 (M+1, 100%).

EXAMPLE 25

N-(4-(4-(N-(Benzyloxycarbonyl)
(methoxycarbonylmethyl)amino)-piperidin-1-yl)-2-
(S)-(3-chlorophenyl)butyl)-N-
methylbenzenesulfonamide hydrochloride Mass spectrum (ESI): m/z 642 (M+1, 100%).

EXAMPLE 26

N-(4-(4-(N-(Benzyloxycarbonyl)(propargyl)amino)
piperidin-1-yl)-2-(S)-(3-chlorophenyl)butyl)-N-
methylbenzenesulfonamide hydrochloride Mass spectrum (ESI): m/z 608 (M+1, 100%).

EXAMPLE 27

N-(4-4-(N-(Benzyloxycarbonyl)
(aminocarbonylmethyl)amino)piperidin-1-yl)-2-(S)-
(3-chlorophenyl)butyl)-N-
methylbenzenesulfonamide hydrochloride Mass spectrum (ESI): m/z 627 (M+1, 100%).

EXAMPLE 28

N-(4-(4-(N-(4-Nitrobenzyloxycarbonyl)(allyl)amino)
piperidin-1-yl)-2-(S)-(3-chlorophenyl)butyl)-N-
methylbenzenesulfonamide hydrochloride Mass spectrum (ESI): m/z 655 (M+1, 100%).

EXAMPLE 29

N-(4-(4-(N-(4-Nitrobenzyloxycarbonyl)(propargyl)
amino)piperidin-1-yl)-2-(S)-(3-chlorophenyl)butyl)-
N-methylbenzenesulfonamide hydrochloride Mass spectrum (ESI): m/z 653 (M+1, 100%).

EXAMPLE 30

N-(4-(4-(N-(4-Nitrobenzyloxycarbonyl)
(cyanomethyl)amino)piperidin-1-yl)-2-(S)-(3-
chlorophenyl)butyl)-N-methylbenzenesulfonamide
hydrochloride Mass spectrum (ESI): m/z 654 (M+1, 100%).

EXAMPLE 31

N-(4-(4-(N-(Benzyloxycarbonyl)(2-hydroxyethyl)
amino)piperidin-1-yl)-2-(S)-(3-chlorophenyl)butyl)-
N-methylbenzenesulfonamide hydrochloride Mass spectrum (ESI): m/z 614 (M+1, 100%).

EXAMPLE 32

N-(4-(4-(N-(4-Nitrobenzyloxycarbonyl)(2-
hydroxyethyl)amino)piperidin-1-yl)-2-(S)-(3-
chlorophenyl)butyl)-N-methylbenzenesulfonamide
hydrochloride Mass spectrum (ESI): m/z 659 (M+1, 100%).

EXAMPLES 33–44

Using essentially the same procedure as described in Example 1, Step I, but substituting the appropriate 4-aminopiperidine derivative (prepared as in Example 1, Steps D–E or Example 2, A–B) and racemic N-methyl-N-(R,S)-2-(2- or 3-thienyl)-4-oxobutyl)benzene-sulfonamide (prepared as described by J. Hale et al., *Bioorganic and Medicinal Chemistry Letters*, 1993, 3, 319–322 and Example 1, Step G), the following racemic compounds were prepared (without need for chiral HPLC separation of enantiomers).

EXAMPLE 33

N-(4-(4-(N-(Benzyloxycarbonyl)
(cyclopropylmethyl)amino)piperidin-1-yl)-2-(R,S)-
(3-thienyl)butyl)-N-methylbenzenesulfonamide
hydrochloride Mass spectrum (ESI): m/z 596 (M+1, 100%).

EXAMPLE 34

N-(4-(4-(N-(Benzyloxycarbonyl)
(methoxycarbonylmethyl)amino)-piperidin-1-yl)-2-
(R,S)-(3-thienyl)butyl)-N-
methylbenzenesulfonamide hydrochloride Mass spectrum (ESI): m/z 614 (M+1, 100%).

EXAMPLE 35

N-(4-(4-(N-(Benzyloxycarbonyl)
(methoxycarbonylmethyl)amino)-piperidin-1-yl)-2-
(R,S)-(2-thienyl)butyl)-N-
methylbenzenesulfonamide hydrochloride Mass spectrum (ESI): m/z 614 (M+1, 100%).

EXAMPLE 36

N-(4-(4-(N-(Benzyloxycarbonyl)(propargyl)amino)
piperidin-1-yl)-2-(R,S)-(3-thienyl)butyl)-N-
methylbenzenesulfonamide hydrochloride Mass spectrum (ESI): m/z 580 (M+1, 100%).

EXAMPLE 37

N-(4-(4-(N-(Benzyloxycarbonyl)(propargyl)amino)
piperidin-1-yl)-2-(R,S)-(2-thienyl)butyl)-N-
methylbenzenesulfonamide hydrochloride Mass spectrum (ESI): m/z 580 (M+1, 100%).

EXAMPLE 38

N-(4-(4-(N-(Benzyloxycarbonyl)
(aminocarbonylmethyl)amino)piperidin-1-yl)-2-(R,
S)-(3-thienyl)butyl)-N-methylbenzenesulfonamide
hydrochloride Mass spectrum (ESI): m/z 599 (M+1, 100%).

EXAMPLE 39

N-(4-(4-(N-(Benzyloxycarbonyl)
(aminocarbonylmethyl)amino)piperidin-1-yl)-2-(R,
S)-(2-thienyl)butyl)-N-methylbenzenesulfonamide
hydrochloride Mass spectrum (ESI): m/z 599 (M+1, 100%).

EXAMPLE 40

N-(4-(4-(N-(4-Nitrobenzyloxycarbonyl)(allyl)amino)
piperidin-1-yl)-2-(R,S)-(3-thienyl)butyl)-N-
methylbenzenesulfonamide hydrochloride Mass spectrum (ESI): m/z 627 (M+1, 100%).

EXAMPLE 41

N-(4-(4-(N-(4-Nitrobenzyloxycarbonyl)(propargyl)
amino)piperidin-1-yl)-2-(R,S)-(3-thienyl)butyl)-N-
methylbenzenesulfonamide hydrochloride Mass spectrum (ESI): m/z 625 (M+1, 100%).

EXAMPLE 42

N-(4-(4-(N-(4-Nitrobenzyloxycarbonyl)
(cyanomethyl)amino)piperidin-1-yl)-2-(R,S)-(3-
thienyl)butyl)-N-methylbenzenesulfonamide
hydrochloride Mass spectrum (ESI): m/z 626 (M+1, 100%).

EXAMPLE 43

N-(4-(4-(N-(Benzyloxycarbonyl)(2-hydroxyethyl)amino)piperidin-1-yl)-2-(R,S)-(3-thienyl)butyl)-N-methylbenzenesulfonamide hydrochloride Mass spectrum (ESI): m/z 586 (M+1, 100%).

EXAMPLE 44

N-(4-(4-(N-(4-Nitrobenzyloxycarbonyl)(2-hydroxyethyl)amino)-piperidin-1-yl)-2-(R,S)-(3-thienyl)butyl)-N-methylbenzenesulfonamide hydrochloride Mass spectrum (ESI): m/z 631 (M+1, 100%).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

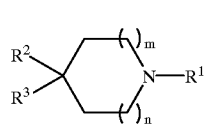

I wherein:
$R^1$ is selected from a group consisting of:
linear or branched $C_{1-8}$ alkyl, linear or branched $C_{2-8}$ alkenyl, wherein the $C_{1-8}$ alkyl or $C_{2-8}$ alkenyl is optionally mono, di, tri or tetra substituted, where the substituents are independently selected from:
(a) hydroxy,
(b) oxo,
(c) cyano,
(d) halogen which is selected from F, Cl, Br, and I,
(e) trifluoromethyl,
(f) phenyl
(g) mono, di or tri-substituted phenyl, where the substituents are independently selected from:
(1') phenyl,
(2') hydroxy,
(3') $C_{1-6}$alkyl,
(4') cyano,
(5') halogen,
(6') trifluoromethyl,
(7') —$NR^6COR^7$,
(8') —$NR^6CO_2R^7$,
(9') —$NR^6CONHR^7$,
(10') —$NR^6S(O)jR^7$, wherein j is 1 or 2,
(11') —$CONR^6R^7$,
(12') —$COR^6$,
(13') —$CO_2R^6$,
(14') —$OR^6$,
(15') —$S(O)_kR^6$, wherein k is 0, 1 or 2,
(h) —$NR^6R^7$,
(i) —$NR^6COR^7$,
(j) —$NR^6CO_2R^7$,
(k) —$NR^6CONHR^7$,
(l) —$NR^6S(O)j-R^7$,
(m) —$CONR^6R^7$,
(n) —$COR^7$,
(o) —$CO_2R^7$,
(p) —$OR^7$,
(q) —$S(O)_kR^7$,
(r) —$NR^6CO$-heteroaryl,
(s) —$NR^6S(O)j$-heteroaryl, and
(t) heteroaryl, wherein heteroaryl is selected from the group consisting of:
(1') benzimidazolyl,
(2') benzofuranyl,
(3') benzoxazolyl,
(4') furanyl,
(5') imidazolyl,
(6') indolyl,
(7') isooxazolyl,
(8') isothiazolyl,
(9') oxadiazolyl,
(10') oxazolyl,
(11') pyrazinyl,
(12') pyrazolyl,
(13') pyridyl,
(14') pyrimidyl,
(15') pyrrolyl,
(16') quinolyl,
(17') tetrazolyl,
(18') thiadiazolyl,
(19') thiazolyl,
(20') thienyl, and
(21') triazolyl,
wherein the heteroaryl is unsubstituted or mono di or tri-substituted,
where the substituents are independently selected from:
(a") phenyl,
(b") hydroxy,
(c") oxo,
(d") cyano,
(e") halogen,
(f") $C_{1-6}$alkyl,and
(g") trifluoromethyl;
with the proviso that $R^1$ bears at least one substituent which is selected from:
—$NR^6S(O)j-R^7$ and —$NR^6S(O)j$-heteroaryl;
$R^2$ is selected from the group consisting of:
(1) hydrogen,
(2) hydroxy,
(3) $C_{1-6}$ alkyl,
(4) substituted $C_{1-6}$ alkyl, where the substituents are independently selected from:
(a) phenyl,
(b) hydroxy,
(c) oxo,
(d) halogen,
(e) trifluoromethyl,
(f) —$N(R^4)(R^5)$, wherein $R^4$ and $R^5$ are independently selected from hydrogen, $C_{1-6}$ alkyl, and $C_{1-6}$ alkyl substituted with $C_{5-8}$ cycloalkyl, (g) —N(R⁴)—CO—O—(R⁵), and
(h) —N(R⁴')—CO—N(R⁴)(R⁵), wherein R⁴' is selected from the definitions of R⁴,
(5) —O—C$_{1-6}$ alkyl, and
(6) phenyl;

R³ is selected from the group consisting of:
(1) —N(R⁸)—CO—O—(C$_{1-6}$ alkyl)-Ar, and
(2) —N(R⁸)—CO—O—R⁷;

Ar is selected from the group consisting of:
(1) phenyl,
(2) pyridyl,
(3) pyrimidyl,
(4) naphthyl,
(5) furyl,
(6) pyrryl,
(7) thienyl,
(8) isothiazolyl,
(9) imidazolyl,
(10) benzimidazolyl,
(11) tetrazolyl,
(12) pyrazinyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) isoxazolyl,
(23) thiazolyl,
(24) oxazolyl,
(25) triazinyl, and
(26) benzthiazolyl,
(27) benzoxazolyl,
(28) imidazopyrazinyl,
(29) triazolopyrazinyl,
(30) naphthyridinyl,
(31) furopyridinyl,
(32) thiopyranopyrimidyl and the 5-oxide and 5-dioxide thereof,
(33) pyridazinyl,
(34) quinazolinyl,
(35) pteridinyl,
(36) triazolopyrimidyl,
(37) triazolopyrazinyl,
(38) thiapurinyl,
(39) oxapurinyl, and
(40) deazapurinyl, wherein Ar items (1) to (40) are unsubstituted or mono or di-substituted, where the substituents are independently selected from:
(a) C$_{1-6}$ alkyl, unsubstituted or substituted with a substituent selected from:
(1') oxo,
(2') hydroxy,
(3') —OR⁷,
(4') phenyl,
(5') trifluoromethyl, and
(6') phenyl or mono, di or tri-substituted phenyl, where the substituents are independently selected from: hydroxy, cyano, halogen, and trifluoromethyl,
(b) halogen,
(c) —OC$_{1-6}$ alkyl,
(d) trifluoromethyl,
(e) hydroxy,
(f) —NO$_2$,
(g) —(CH$_2$)$_p$S(O)$_k$—(C$_{1-6}$ alkyl), wherein p is 0, 1 or 2,
(h) —(CH$_2$)$_p$S(O)j-NH$_2$,
(i) —(CH$_2$)$_p$S(O)j-NH(C$_{1-6}$ alkyl),
(j) —(CH$_2$)$_p$S(O)j-NHR⁶,
(k) —(CH$_2$)$_p$S(O)j-NR⁶—(C$_{1-6}$ alkyl),
(l) —(CH$_2$)$_p$CONH$_2$,
(m) —(CH$_2$)$_p$CONH—(C$_{1-6}$ alkyl),
(n) —(CH$_2$)$_p$CONHR⁶,
(o) —(CH$_2$)$_p$CONR⁶—(C$_{1-6}$ alkyl),
(p) —(CH$_2$)$_p$CO$_2$H,
(q) —(CH$_2$)$_p$CO$_2$—(C$_{1-6}$ alkyl),
(r) —(CH$_2$)$_p$NR⁶R⁷,
(s) —(CH$_2$)$_p$NH—C(O)—C$_{1-6}$alkyl,
(t) —(CH$_2$)$_p$NH—C(O)—NH$_2$,
(u) —(CH$_2$)$_p$NH—C(O)—NHC$_{1-6}$alkyl,
(v) —(CH$_2$)$_p$NH—C(O)—N(C$_{1-6}$ alkyl)$_2$,
(w) —(CH$_2$)$_p$NH—S(O)$_k$—C$_{1-6}$alkyl,
(x) —(CH$_2$)$_p$N(C$_{1-3}$alkyl)—C(O)—N(diC$_{1-6}$ alkyl),
(y) —(CH$_2$)$_p$—heteroaryl, —C(O)-heteroaryl or —(CH$_2$)$_p$—O-heteroaryl, wherein the heteroaryl is selected from the group consisting of:
(1') benzimidazolyl,
(2') benzofuranyl,
(3') benzothiophenyl,
(4') benzoxazolyl,
(5') furanyl,
(6') imidazolyl,
(7') indolyl,
(8') isooxazolyl,
(9') isothiazolyl,
(10') oxadiazolyl,
(11') oxazolyl,
(12') pyrazinyl,
(13') pyrazolyl,
(14') pyridyl,
(15') pyrimidyl,
(16') pyrrolyl,
(17') quinolyl,
(18') tetrazolyl,
(19') thiadiazolyl,
(20') thiazolyl,
(21') thienyl,
(22') triazolyl,
(23') dihydrobenzimidazolyl,
(24') dihydrobenzofuranyl,
(25') dihydrobenzothiophenyl,
(26') dihydrobenzoxazolyl,
(27') dihydrofuranyl
(28') dihydroimidazolyl,
(29') dihydroindolyl,
(30') dihydroisooxazolyl,
(31') dihydroisothiazolyl,
(32') dihydrooxadiazolyl,
(33') dihydropyrazinyl,
(34') dihydropyrazolyl,
(35') dihydropyridinyl,
(36') dihydropyrimidinyl,
(37') dihydroquinolinyl,
wherein the heteroaryl group of items (1') to (37') is unsubstituted, or mono, di or tri-substituted, where the substituents are selected from:

(a') hydrogen,
(b') $C_{1-6}$ alkyl, branched or unbranched, unsubstituted or mono or di-substituted, where the substituents are selected from: hydrogen and hydroxy,
(c') hydroxy,
(d') oxo,
(e') —$OR^6$,
(f') halogen,
(g') trifluoromethyl,
(h') nitro,
(i') cyano,
(j') —$NHR^6$,
(k') —$NR^6R^7$,
(l') —$NHCOR^6$,
(m') —$NR^6COR^7$,
(n') —$NHCO_2R^6$,
(o') —$NR^6CO_2R^7$,
(p') —$NHS(O)jR^6$,
(q') —$NR_6S(O)jR^7$,
(r') —$CONR^6R^7$,
(s') —$COR^6$,
(t') —$CO_2R^6$, and
(u') —$S(O)jR^6$;

$R^6$ is selected from the group consisting of:
(1) hydrogen,
(2) $C_{1-6}$ alkyl,
(3) substituted $C_{1-6}$ alkyl, where the substituents are independently selected from:
  (a) phenyl,
  (b) hydroxy,
  (c) oxo,
  (d) cyano,
  (e) halogen,
  (f) trifluoromethyl, and
  (g) $C_{5-8}$ cycloalkyl,
(4) phenyl,
(5) mono, di or tri-substituted phenyl, where the substituents are independently selected from:
  (a) hydroxy,
  (b) $C_{1-6}$alkyl,
  (c) cyano,
  (d) halogen, and
  (e) trifluoromethyl, $R^7$ is selected from the group consisting of:
(1) hydrogen,
(2) $C_{1-6}$ alkyl or $C_{5-8}$ cycloalkyl,
(3) substituted $C_{1-6}$ alkyl or $C_{5-8}$ cycloalkyl, where the substituents are independently selected from:
  (a) phenyl,
  (b) mono, di or tri-substituted phenyl, where the substituent is independently selected from:
    (1') hydroxy,
    (2') $C_{1-3}$alkyl,
    (3') cyano,
    (4') halogen,
    (5') trifluoromethyl, and
    (6') $C_{1-3}$alkyloxy,
  (c) hydroxy,
  (d) oxo,
  (e) cyano,
  (f) halogen, and
  (g) trifluoromethyl,
(4) phenyl,
(5) mono, di or tri-substituted phenyl, where the substituents are independently selected from:
  (a) hydroxy,
  (b) $C_{1-6}$alkyl,
  (c) $C_{1-6}$alkoxy
  (d) cyano,
  (e) halogen, and
  (f) trifluoromethyl;

or $R^6$ and $R^7$ may be joined together to form a 5-, 6-, or 7-membered monocyclic saturated ring containing 1 or 2 heteroatoms independently selected from nitrogen, oxygen, and sulfur, and in which the ring is unsubstituted or mono or di-substituted, the substituents independently selected from:
(1) hydroxy,
(2) oxo,
(3) cyano,
(4) halogen,
(5) trifluoromethyl, $R^8$ is selected from the group consisting of:
(1) $C_{2-10}$ alkenyl,
(2) $C_{2-10}$ alkynyl,
(3) heteroaryl,
(3) substituted $C_{1-10}$ alkyl, $C_{2-10}$ alkenyl or $C_{2-10}$ alkynyl, where the substituents are independently selected from:
  (a) $C_{3-4}$ cycloalkyl,
  (b) hydroxy,
  (c) $C_{1-6}$ alkyloxy,
  (d) cyano,
  (e) heteroaryl,
  (f) halogen,
  (g) trifluoromethyl,
  (h) —$CO_2H$,
  (i) —$SO_3H$,
  (j) —$CO_2R^6$,
  (k) —$CONR^6R^7$,
  (l) —$NR^4CONR^6R^7$,
  (m) —$NR^4CO_2R^6$,
  (n) —$NR^4COR^6$, and
  (o) —$SR^4$;

m is an integer selected from 0, 1 and 2,
n is an integer selected from 0, 1 and 2,
and pharmaceutically acceptable salts thereof.

2. The compound of claim 1 of formula Ia:

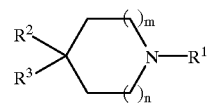

Ia wherein:
$R^1$ is selected from a group consisting of:
  $C_3$, $C_4$, $C_5$, $C_6$, $C_7$, or $C_8$ linear or branched alkyl, which is unsubstituted or mono, di or tri-substituted, where the substituents are independently selected from:
    (a) hydroxy,
    (b) Cl or F,
    (c) phenyl,
    (d) mono, di or tri-substituted phenyl, where the substituents are independently selected from:
      (1') phenyl,
      (2') hydroxy,
      (3') $C_{1-6}$alkyl,
      (4') cyano,
      (5') halogen, and
      (6') tri fluoromethyl,
    (e) —$NR^6CO$—$R^7$, wherein $R^6$ is hydrogen or $C_{1-6}$ alkyl, unsubstituted or substituted with $C_{5-8}$ cycloalkyl, and $R^7$ is $C_{1-6}$ alkyl, benzyl or phenyl which is unsubstituted or substituted with halo, $CF_3$, $C_{1-6}$alkyl, or $C_{1-3}$alkoxy,
- (f) —$COR^7$,
- (g) —$OR^7$,
- (h) —$NR^6S(O)j$-$R^7$, where j is 1 or 2,
- (i) —$NR^6S(O)j$-heteroaryl, wherein heteroaryl is selected from the group consisting of:
  - (1') benzimidazolyl,
  - (2') benzofuranyl,
  - (3') benzothiophenyl,
  - (4') benzoxazolyl,
  - (5') furanyl,
  - (6') imidazolyl,
  - (7') indolyl,
  - (8') isooxazolyl,
  - (9') isothiazolyl,
  - (10') oxadiazolyl,
  - (11') oxazolyl,
  - (12') pyrazinyl,
  - (13') pyrazolyl,
  - (14') pyridyl,
  - (15') pyrimidyl,
  - (16') pyrrolyl,
  - (17') quinolyl,
  - (18') tetrazolyl,
  - (19') thiadiazolyl,
  - (20') thiazolyl,
  - (21') thienyl,
  - (22') triazolyl,
  - (23') dihydrobenzimidazolyl,
  - (24') dihydrobenzofuranyl,
  - (25') dihydrobenzothiophenyl,
  - (26') dihydrobenzoxazolyl,
  - (27') dihydrofuranyl,
  - (28') dihydroimidazolyl,
  - (29') dihydroindolyl,
  - (30') dihydroisooxazolyl,
  - (31') dihydroisothiazolyl,
  - (32') dihydrooxadiazolyl,
  - (33') dihydropyrazinyl,
  - (34') dihydropyrazolyl,
  - (35') dihydropyridinyl,
  - (36') dihydropyrimidinyl,
  - (37') dihydroquinolinyl, wherein the heteroaryl is unsubstituted or mono di or tri-substituted, where the substituents are independently selected from:
- (a') phenyl,
- (b') hydroxy,
- (c') oxo,
- (d') cyano,
- (e') halogen,
- (f') $C_{1-6}$alkyl,and
- (g') trifluoromethyl;
  with the proviso that $R^1$ bears at least one substituent which is selected from:
    —$NR^6S(O)j$-$R^7$ and —$NR^6S(O)j$-heteroaryl;

$R^2$ is selected from the group consisting of:
- (1) hydrogen,
- (2) hydroxy,
- (3) $C_{1-6}$ alkyl,
- (4) —O—$C_{1-6}$ alkyl,
- (5) phenyl,
- (6) —$N(CH_3)$—CO—$N(H)(CH_3)$,
- (7) —$N(H)$—CO—O—$C_{1-3}$, and
- (8) —CO—$CH_3$;

$R^3$ is selected from the group consisting of:
- (1) —$N(R^8)$—CO—O—($C_{1-6}$ alkyl)-Ar, and
- (2) —$N(R^8)$—CO—O—$R^7$;

Ar is selected from the group consisting of:
- (1) phenyl,
- (2) pyrazinyl,
- (3) pyrazolyl,
- (4) pyridyl,
- (5) pyrimidyl, and
- (6) thienyl,
  wherein the Ar is unsubstituted or mono or di-substituted, and the substituents are independently selected from:
  - (a) $C_{1-6}$ alkyl, unsubstituted or substituted with
    - (1') oxo,
    - (2') hydroxy,
    - (3') —$OR^7$,
    - (4') phenyl, and
    - (5') trifluoromethyl,
  - (b) halogen,
  - (c) —$OC_{1-6}$ alkyl,
  - (d) trifluoromethyl,
  - (e) —$NO_2$,
  - (f) $CONR^6$—($C_{1-2}$ alkyl),
  - (g) $CO_2H$,
  - (h) $CO_2$—($C_{1-2}$ alkyl),
  - (i) $CH_2NR^6$—($C_{1-2}$ alkyl),
  - (j) $CH_2NH$—$C(O)$—$C_{1-3}$alkyl,
  - (k) $CH_2NH$—$C(O)NH_2$,
  - (l) $CH_2NH$—$C(O)NHC_{1-3}$alkyl,
  - (m) $CH_2NH$—$C(O)N$-$diC_{1-3}$ alkyl),
  - (l) $CH_2NH$—$S(O)j$-$C_{1-3}$alkyl,
  - (o) $CH_2$-heteroaryl, with the heteroaryl is selected from the group consisting of:
    - (1') imidazolyl,
    - (2') oxazolyl,
    - (3') pyridyl,
    - (4') tetrazolyl,
    - (5') triazolyl,
  and the heteroaryl is unsubstituted, mono, di or tri-substituted, where the substituents selected from:
  - (a') hydrogen,
  - (b') $C_{1-6}$ alkyl, branched or unbranched, unsubstituted or mono or di-substituted, the substituents being selected from hydrogen and hydroxy;

$R^8$ is selected from the group consisting of:
- (1) $C_{2-10}$ alkenyl,
- (2) $C_{2-10}$ alkynyl,
- (3) heteroaryl,
- (4) substituted $C_{1-10}$ alkyl, $C_{2-10}$ alkenyl or $C_{2-10}$ alkynyl, where the substituents are independently selected from:
  - (a) $C_{3-4}$ cycloalkyl,
  - (b) hydroxy,
  - (c) $C_{1-6}$ alkyloxy,
  - (d) cyano,
  - (e) heteroaryl,
  - (f) halogen,
  - (g) trifluoromethyl,
  - (h) —$CO_2H$,
  - (i) —$SO_3H$,
  - (j) —$CO_2R^6$,
  - (k) —$CONR^6R^7$,
  - (l) —$NR^4CONR^6R^7$,
  - (m) —$NR^4CO_2R^6$,
  - (n) —$NR^4COR^6$, and
  - (o) —$SR^4$;

129 m is an integer selected from 0, 1 and 2,
n is an integer selected from 0, 1 and 2, with the proviso that the sum of m+n is 2;
and pharmaceutically acceptable salts thereof.

3. The compound of claim 1 of formula Ib:

Ib wherein:
$R^1$, $R^2$ and $R^3$ are as defined in claim 1;
and pharmaceutically acceptable salts thereof.

4. The compound of claim 1 wherein:
$R^1$ is selected from the group consisting of:
$C_3$, $C_4$, $C_5$, $C_6$, $C_7$, or $C_8$ linear or branched alkyl, which is unsubstituted or mono, di or tri-substituted, where the substituents are independently selected from:
(a) hydroxy,
(b) Cl or F,
(c) phenyl,
(d) mono, di or tri-substituted phenyl, where the substituents are independently selected from:
(1') phenyl,
(2') hydroxy,
(3') $C_{1-6}$alkyl,
(4') cyano,
(5') halogen, and
(6') trifluoromethyl,
(e) —$NR^6CO$—$R^7$, wherein $R^6$ is hydrogen or $C_{1-6}$ alkyl, unsubstituted or substituted with $C_{5-8}$ cycloalkyl, and $R^7$ is $C_{1-6}$ alkyl, benzyl or phenyl which is unsubstituted or substituted with halo, $CF_3$, $C_{1-6}$alkyl, or $C_{1-3}$alkoxy,
(f) —$COR^7$,
(g) —$OR^7$,
(h) —$NR^6S(O)j$-$R^7$, where j is 1 or 2,
(i) —$NR^6S(O)j$-heteroaryl, wherein heteroaryl is selected from the group consisting of:
(1') benzimidazolyl,
(2') benzofuranyl,
(3') benzoxazolyl,
(4') furanyl,
(5') imidazolyl,
(6') indolyl,
(7') isooxazolyl,
(8') isothiazolyl,
(9') oxadiazolyl,
(10') oxazolyl,
(11') pyrazinyl,
(12') pyrazolyl,
(13') pyridyl,
(14') pyrimidyl,
(15') pyrrolyl,
(16') quinolyl,
(17') tetrazolyl,
(18') thiadiazolyl,
(19') thiazolyl,
(20') thienyl, and
(21') triazolyl,
wherein the heteroaryl is unsubstituted or mono di or tri-substituted,
where the substituents are independently selected from:
(a') phenyl,
(b') hydroxy,

130

(c') oxo,
(d') cyano,
(e') halogen,
(f') $C_{1-6}$alkyl, and
(g') trifluoromethyl;
with the proviso that $R^1$ bears at least one substituent which is selected from:
—$NR^6S(O)j$-$R^7$ and —$NR^6S(O)j$-heteroaryl.

5. The compound of claim 1 wherein:
$R^1$ is selected from the croup consisting of:
$C_4$, $C_5$, $C_6$, $C_7$ or $C_8$ linear or branched alkyl, which is mono, di- or tri-substituted, where the substituents are independently selected from:
(a) hydroxy,
(b) Cl or F,
(c) phenyl,
(d) mono, di or tri-substituted phenyl, where the substituents are independently selected from:
(1') hydroxy,
(2') methyl or ethyl,
(3') Cl or F, and
(4') trifluoromethyl,
(e) —$NR^6CO$—$R^7$, wherein $R^6$ is $C_{1-3}$ alkyl, unsubstituted or substituted with cyclohexyl, and $R^7$ is $C_{1-6}$ alkyl, benzyl or phenyl which is unsubstituted or substituted with halo, $CF_3$, $C_{1-3}$alkyl, or $C_{1-3}$alkoxy,
(f) —$NR^6S(O)j$-$R^7$, where j is 1 or 2, and where $R^6$ is $C_{1-3}$ alkyl, unsubstituted or substituted with cyclohexyl, and $R^7$ is $C_{1-6}$ alkyl, benzyl or phenyl which is unsubstituted or substituted with halo, $CF_3$, $C_{1-3}$alkyl, or $C_{1-3}$alkoxy;
with the proviso that $R^1$ bears at least one substituent which is —$NR^6S(O)j$-$R^7$.

6. The compound of claim 1 wherein:
$R^1$ is selected from the group consisting of:
$C_4$, $C_5$, or $C_6$ linear alkyl, which is substituted, where the substituents are independently selected from:
(a) phenyl,
(b) mono, di or tri-substituted phenyl, where the substituents are independently selected from:
(1') hydroxy,
(2') methyl or ethyl,
(3') Cl or F, and
(4') trifluoromethyl,
(c) $C_{1-6}$ alkyl,
(d) —$NR^6CO$—$R^7$, wherein $R^6$ is methyl, unsubstituted or substituted with cyclohexyl, and $R^7$ is phenyl which is unsubstituted or substituted with Cl, F, $CF_3$, $C_{1-3}$alkyl or $C_{1-3}$alkoxy, and
(e) —$NR^6S(O)j$-$R^7$, where is 1 or 2;
with the proviso that $R^1$ bears at least one substituent which is —$NR^6S(O)j$-$R^7$.

7. The compound of claim 1 wherein:
$R^1$ is $C_4$ linear alkyl, which is substituted, where the substituents are independently selected from:
(a) phenyl,
(b) mono, di or tri-substituted phenyl, where the substituents are independently selected from:
(1') hydroxy,
(2') methyl or ethyl,
(3') Cl or F, and
(4') trifluoromethyl,
(c) $C_{1-6}$ alkyl, and
(d) —$NR^6S(O)j$-$R^7$, where $R^6$ is methyl, unsubstituted or substituted with cyclohexyl, and $R^7$ is phenyl which is unsubstituted or substituted with Cl, F, CF$_3$, C$_{1-3}$alkyl or C$_{1-3}$alkoxy, and j is 1 or 2;

with the proviso that R$^1$ bears at least one substituent which is —NR$^6$S(O)j-R$^7$.

8. The compound of claim 1 wherein:

R$^1$ is:

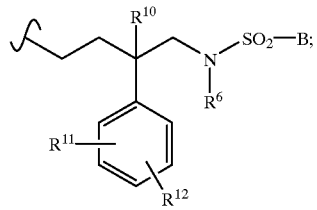

wherein:

B is selected from the group consisting of:
  (a) phenyl, and
  (b) di or tri-substituted phenyl, wherein the substituents on phenyl are independently selected from: chloro, methyl, phenyl, C$_{1-3}$alkoxy, and CF$_3$;

R$^6$ is C$_{1-3}$ alkyl, unsubstituted or substituted with cyclohexyl;

R$^{10}$ is selected from the group consisting of:
  (1) hydrogen, and
  (2) C$_{1-6}$ alkyl;

R$^{11}$ and R$^{12}$ are independently selected from the group consisting of:
  (1) hydrogen,
  (2) hydroxy,
  (3) methyl or ethyl,
  (4) Cl or F, and
  (5) trifluoromethyl.

9. The compound of claim 1 wherein:

R$^1$ is selected from the group consisting of:

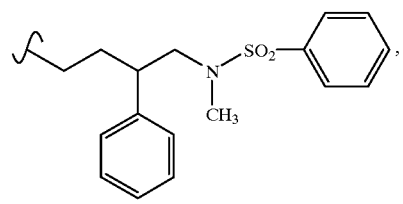

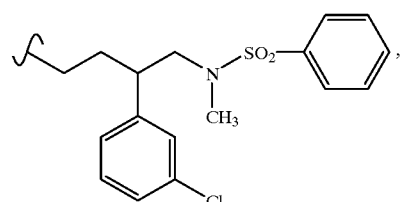

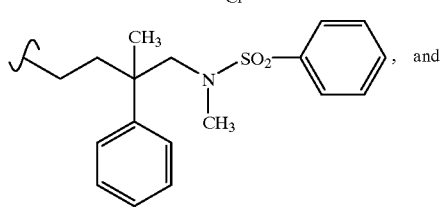

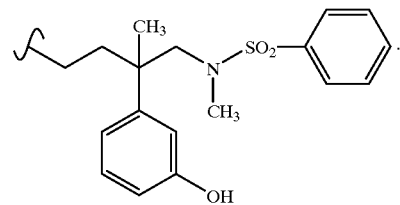

10. The compound of claim 1 wherein:

R$^1$ is selected from the group consisting of:

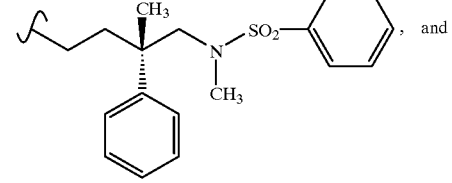

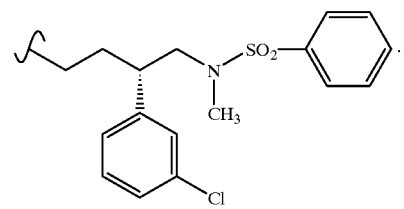

11. The compound of claim 1 wherein:

R$^2$ is selected from the group consisting of:
  (1) hydrogen,
  (2) hydroxy,
  (3) C$_{1-6}$ alkyl,
  (4) —O—C$_{1-6}$ alkyl, and
  (5) phenyl.

12. The compound of claim 1 wherein:

R$^2$ is selected from the group consisting of:
  (1) hydrogen,
  (2) hydroxy, and
  (3) phenyl.

13. The compound of claim 1 wherein:

R$^2$ is hydrogen.

14. The compound of claim 1 where in:

Ar is selected from the group consisting of:
  (1) phenyl,
  (2) pyrazinyl,
  (3) pyrazolyl,
  (4) pyridyl,
  (5) pyrimidyl, and
  (6) thienyl,
    wherein the Ar is unsubstituted or mono or di-substituted, and substituents are independently selected from:
    (a) C$_{1-3}$ alkyl, unsubstituted or substituted with
      (1') oxo,
      (2') hydroxy,
      (3') —OR$^7$,
      (4') phenyl, and
      (5') trifluoromethyl,
    (b) —NO$_2$,
    (c) —CONH$_2$,
    (d) —CONR$^6$—(C$_{1-2}$ alkyl),
    (e) —CO$_2$H,
    (f) —CO$_2$—(C$_{1-2}$ alkyl), (g) —$CH_2NR^6$—($C_{1-2}$ alkyl),
(h) —$CH_2NH$—$C(O)$—$C_{1-3}$alkyl,
(i) —$CH_2NH$—$C(O)NH_2$,
(j) —$CH_2NH$—$C(O)NHC_{1-3}$alkyl,
(k) —$CH_2NH$—$C(O)N$-di$C_{1-3}$ alkyl),
(l) —$CH_2NH$—$S(O)j$-$C_{1-3}$alkyl,
(m) —$CH_2$-heteroaryl, with the heteroaryl is selected from the group consisting of:
(1') imidazolyl,
(2') oxazolyl,
(3') pyridyl,
(4') tetrazolyl,
(5') triazolyl,
and the heteroaryl is unsubstituted, mono, di or tri-substituted, where the substituents selected from:
(a') hydrogen,
(b') $C_{1-6}$ alkyl, branched or unbranched, unsubstituted or mono or di-substituted, the substituents being selected from hydrogen and hydroxy.

15. The compound of claim 1 wherein:
Ar is selected from:
phenyl, mono substituted phenyl or di-substituted phenyl, wherein the substituents are selected from the group consisting
(a) $C_{1-3}$ alkyl, unsubstituted or substituted with
(1') oxo,
(2') hydroxy, or
(3') —$OR^6$, wherein $R^6$ is hydrogen or $C_{1-3}$ alkyl,
(b) —$NO_2$,
(c) —$CONH_2$,
(d) —$CO_2H$,
(e) —$CH_2NR^6$—($C_{1-2}$ alkyl),
(f) —$CH_2NH$—$C(O)$—$C_{1-3}$alkyl,
(g) —$CH_2NH$—$C(O)NH_2$,
(h) —$CH_2NH$—$C(O)NHC_{1-3}$alkyl,
(i) —$CH_2NH$—$C(O)N$-di$C_{1-3}$ alkyl),
(j) —$CH_2NH$—$S(O)j$-$C_{1-3}$alkyl, and
(k) —$CH_2$-heteroaryl, where heteroaryl is selected from the group consisting of:
(1') imidazolyl,
(2') oxazolyl,
(3') pyridyl,
(4') tetrazolyl,
(5') triazolyl,
and where heteroaryl is unsubstituted, mono, di or tri substituted, where the substituents are independently selected from:
(a') hydrogen,
(b') $C_{1-6}$ alkyl, branched or unbranched, unsubstituted or mono or disubstituted, where the substituents are selected from: hydrogen and hydroxy.

16. The compound of claim 1 wherein:
Ar is selected from:
phenyl, or mono substituted phenyl wherein the substituent is selected from: —$NO_2$, —$CONH_2$, and —$CO_2H$.

17. The compound of claim 1 wherein:
$R^3$ is: —N($R^8$)—CO—O—($C_{1-6}$ alkyl)-Ar.

18. The compound of claim 1 wherein:
$R^3$ is: —N($R^8$)—CO—O—($CH_2$)-Ar.

19. The compound of claim 1 wherein:
$R^3$ is selected from:
(1) —N($R^8$)—CO—O—($CH_2$)-phenyl,
(2) —N($R^8$)—CO—O—($CH_2$)-(phenyl-$NO_2$),
(3) —N($R^8$)—CO—O—($CH_2$)-(phenyl-$CONH_2$), and
(4) —N($R^8$)—CO—O—($CH_2$)-(phenyl-$CO_2H$).

20. The compound of claim 1 wherein:
$R^8$ is selected from the group consisting of:
(1) $C_{2-10}$ alkenyl,
(2) $C_{2-10}$ alkynyl,
(3) heteroaryl,
(4) substituted $C_{1-10}$ alkyl, $C_{2-10}$ alkenyl or $C_{2-10}$ alkynyl, where the substituents are independently selected from:
(a) $C_{3-4}$ cycloalkyl,
(b) hydroxy,
(c) $C_{1-6}$ alkyloxy,
(d) cyano,
(e) heteroaryl,
(f) halogen,
(g) —$CO_2H$,
(h) —$CO_2R^6$, and
(i) —$CONR^6R^7$.

21. The compound of claim 1 wherein:
$R^8$ is selected from the group consisting of:
(1) $C_{2-10}$ alkenyl,
(2) $C_{2-10}$ alkynyl,
(3) substituted $C_{1-10}$ alkyl, $C_{2-10}$ alkenyl or $C_{2-10}$ alkynyl, where the substituents are independently selected from:
(a) $C_{3-4}$ cycloalkyl,
(b) hydroxy,
(c) $C_{1-6}$ alkyloxy,
(d) cyano,
(e) tetrazolyl,
(f) fluoro,
(g) —$CO_2H$,
(h) —$CO_2R^6$, and
(i) —$CONR^6R^7$.

22. The compound of claim 1 wherein:
$R^8$ is selected from the group consisting of:
(1) $C_{3-5}$ alkenyl,
(2) $C_{3-4}$ alkynyl,
(3) substituted $C_{1-4}$ alkyl, where the substituents are independently selected from:
(a) cyclopropyl,
(b) cyclobutyl,
(c) cyano,
(d) fluoro,
(e) —$CO_2CH_3$,
(f) —$CONH_2$,
(g) $C_{1-2}$ alkyloxy, and
(h) hydroxy.

23. The compound of claim 1 wherein:
$R^8$ is selected from the group consisting of:
(1) —$CH_2$—CH=$CH_2$,
(2) —($CH_2$)$_2$—CH=$CH_2$,
(3) —($CH_2$)$_3$—CH=$CH_2$,
(4) —$CH_2$—C≡CH,
(5) —$CH_2$—C≡N,
(6) —$CH_2$-cyclopropyl,
(7) —$CH_2$-cyclobutyl,
(8) —($CH_2$)$_2$—F,
(9) —$CH_2$—$CO_2$—$CH_3$,
(10) —$CH_2$—CO—$NH_2$,
(11) —($CH_2$)$_2$—$OCH_3$,
(12) —($CH_2$)$_2$—OH,
(13) —($CH_2$)$_3$—OH, and
(14) —$CH_2$—CH(OH)—$CH_2$—OH.

24. The compound of claim 1 wherein:
m is 1, and n is 1.

25. A compound of the formula:

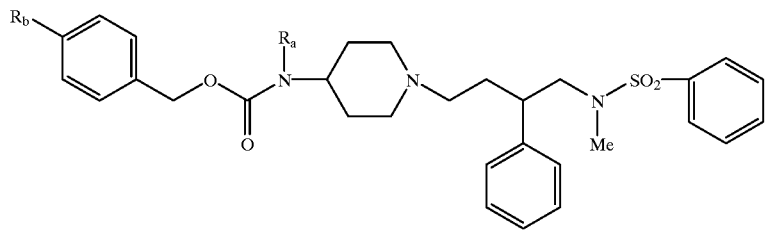

wherein:

| $R_a$ | $R_b$ |
|---|---|
| —$CH_2$—CH=$CH_2$ | hydrogen |
| —$(CH_2)_2$—CH=$CH_2$ | hydrogen |
| —$(CH_2)_3$—CH=$CH_2$ | hydrogen |
| —$CH_2$—C≡CH | hydrogen |
| —$CH_2$—C≡N | hydrogen |
| —$CH_2$-cyclopropyl | hydrogen |
| —$CH_2$-cyclobutyl | hydrogen |
| —$(CH_2)_2$—F | hydrogen |
| —$CH_2$—$CO_2$—$CH_3$ | hydrogen |
| —$CH_2$—$CO_2$—$NH_2$ | hydrogen |
| —$(CH_2)_2$—$OCH_3$ | hydrogen |
| —$(CH_2)_2$—OH | hydrogen |
| —$(CH_2)_3$—OH | hydrogen |
| —$CH_2$—CH(OH)—$CH_2$—OH | hydrogen |
| —$CH_2$—CH=$CH_2$ | —$NO_2$ |
| —$(CH_2)_2$—CH=$CH_2$ | —$NO_2$ |
| —$(CH_2)_3$—CH=$CH_2$ | —$NO_2$ |

-continued

| $R_a$ | $R_b$ |
|---|---|
| —$CH_2$—C≡CH | —$NO_2$ |
| —$CH_2$—C≡N | —$NO_2$ |
| —$CH_2$-cyclopropyl | —$NO_2$ |
| —$CH_2$-cyclobutyl | —$NO_2$ |
| —$(CH_2)_2$—F | —$NO_2$ |
| —$CH_2$—$CO_2$—$CH_3$ | —$NO_2$ |
| —$CH_2$—$CO_2$—$NH_2$ | —$NO_2$ |
| —$(CH_2)_2$—$OCH_3$ | —$NO_2$ |
| —$(CH_2)_2$—OH | —$NO_2$ |
| —$(CH_2)_3$—OH | —$NO_2$ |
| —$CH_2$—CH(OH)—$CH_2$—OH | —$NO_2$ | and pharmaceutically acceptable salts thereof.

26. A compound which is selected from the group consisting of:

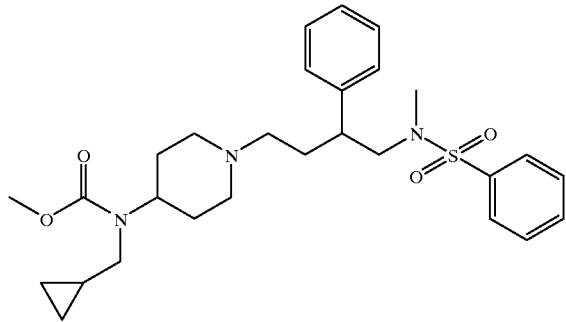

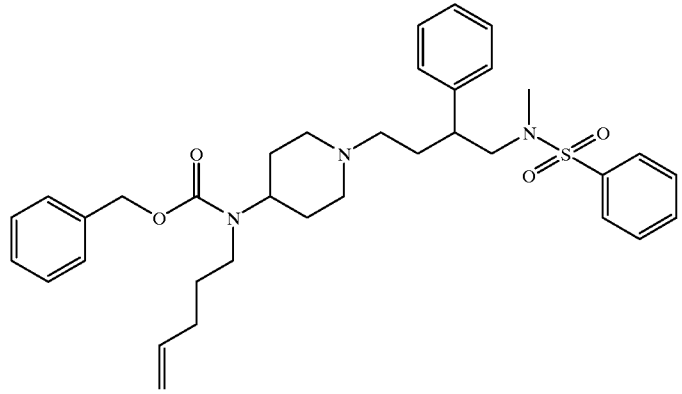

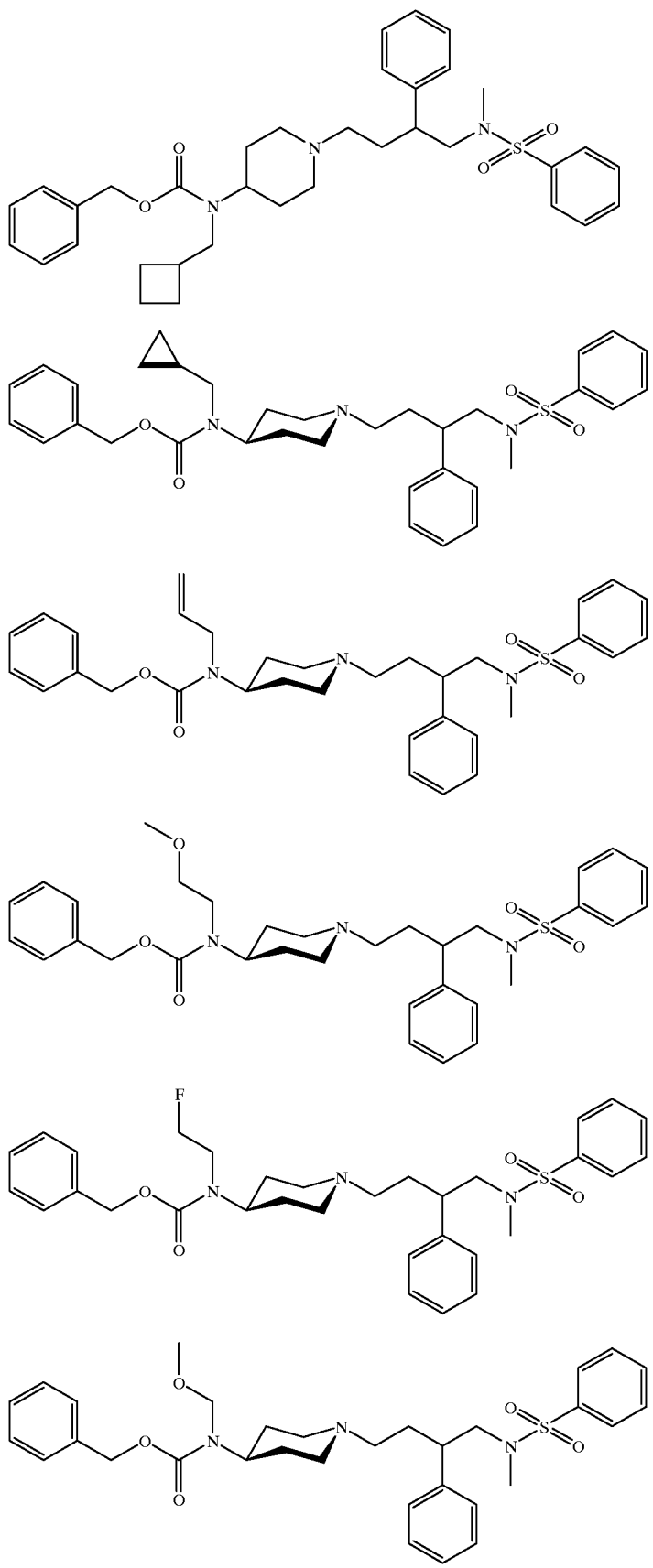

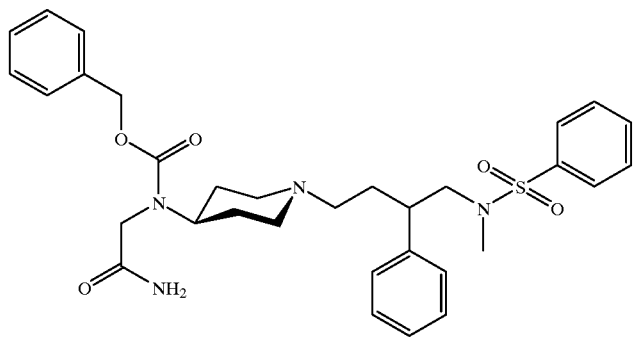
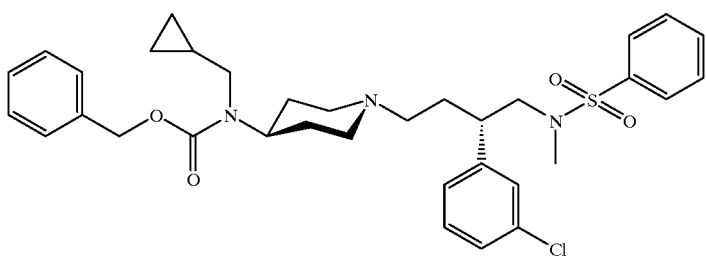
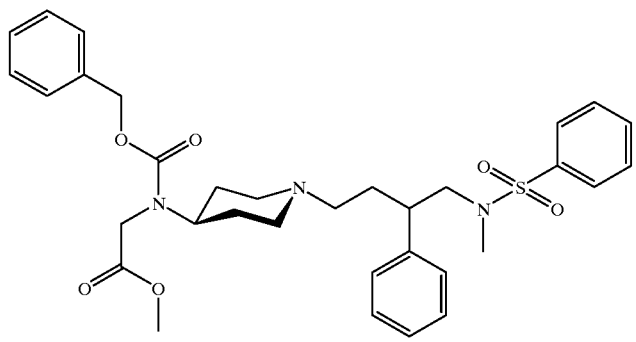
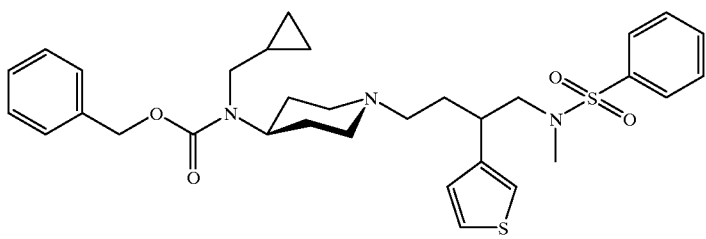
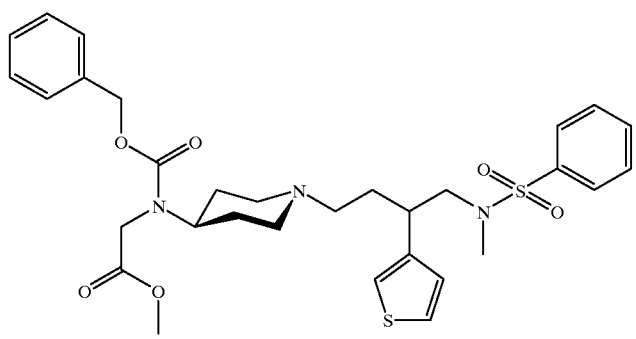

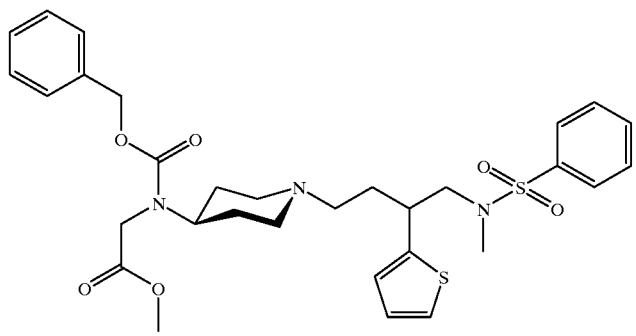
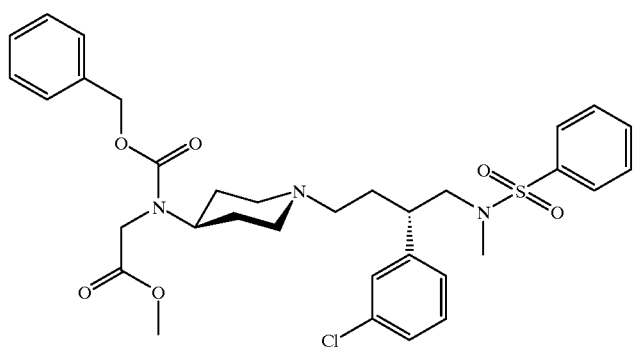
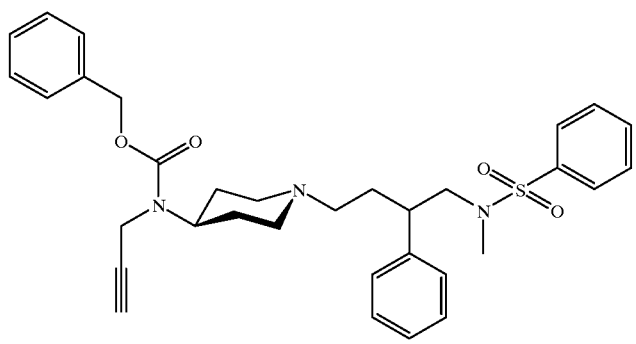
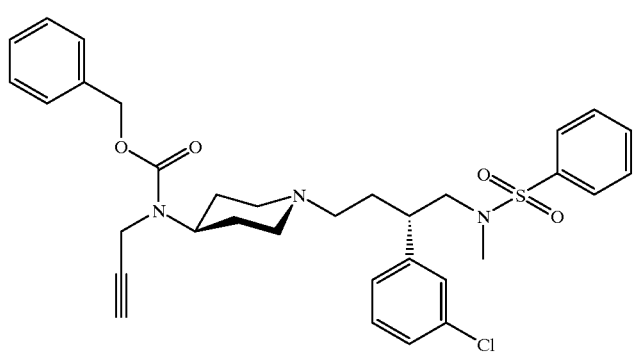

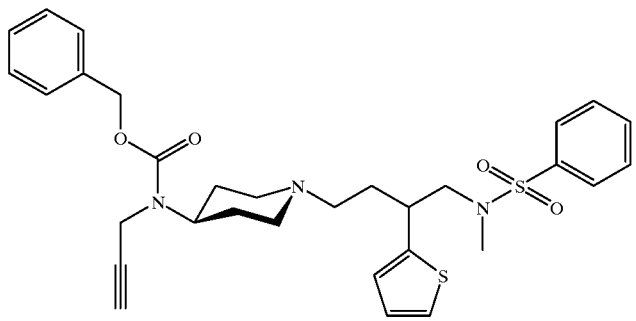
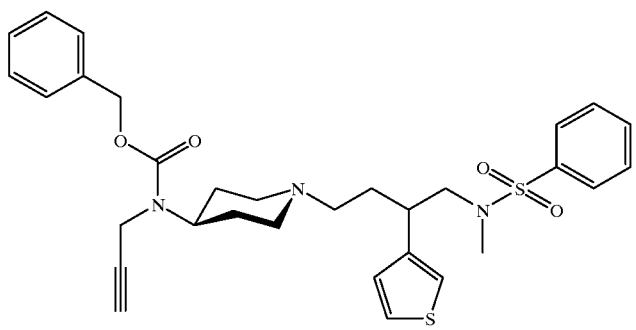
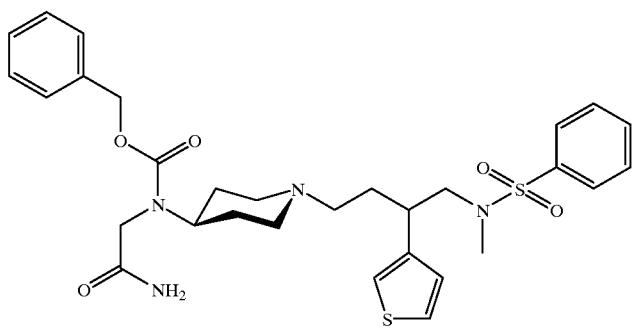
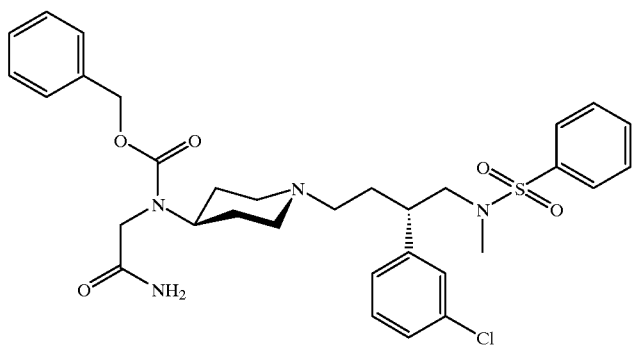

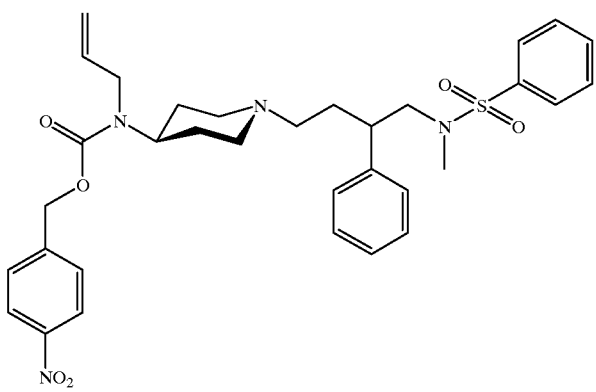
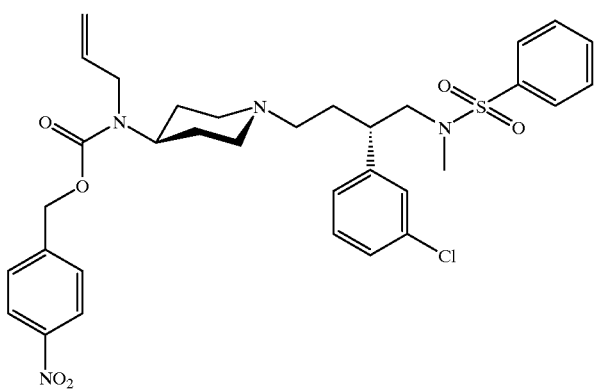
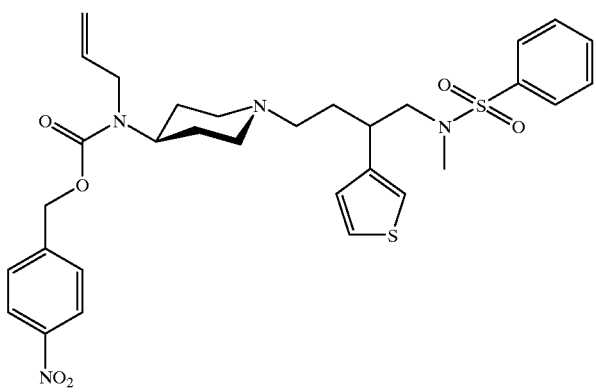
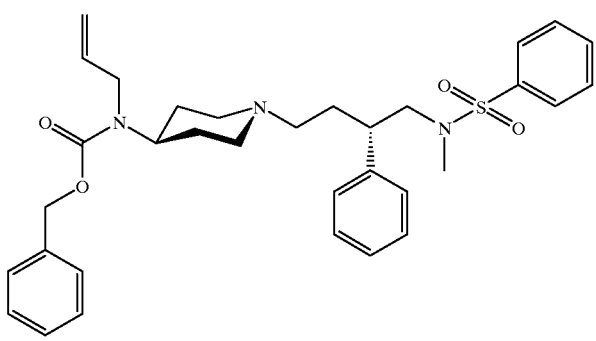

-continued
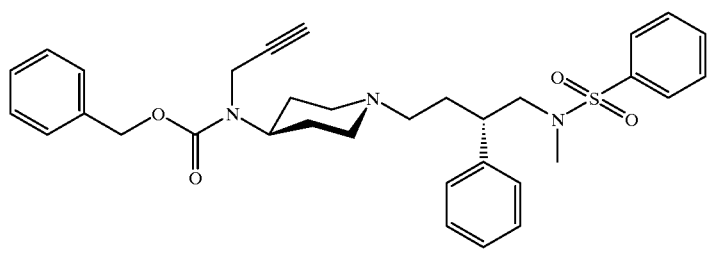
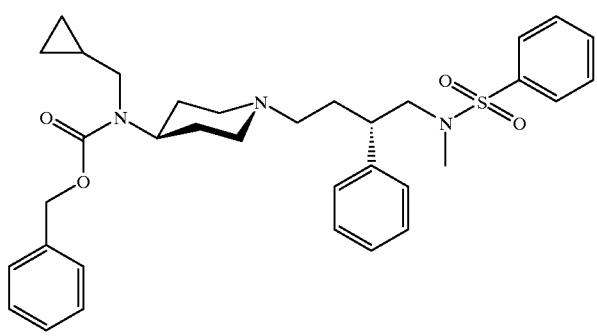
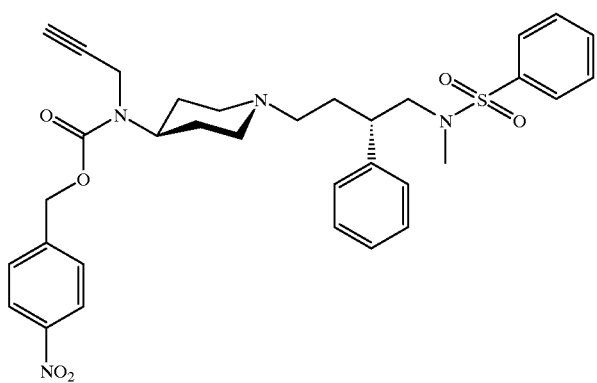
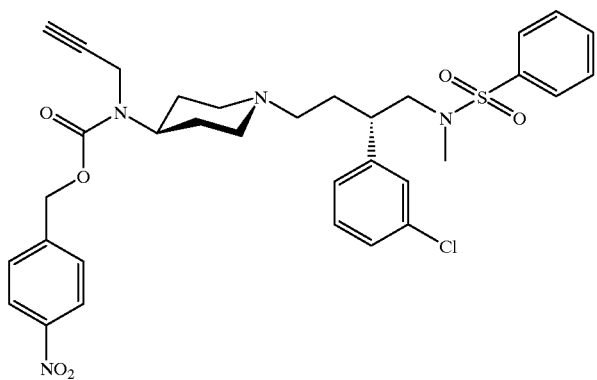

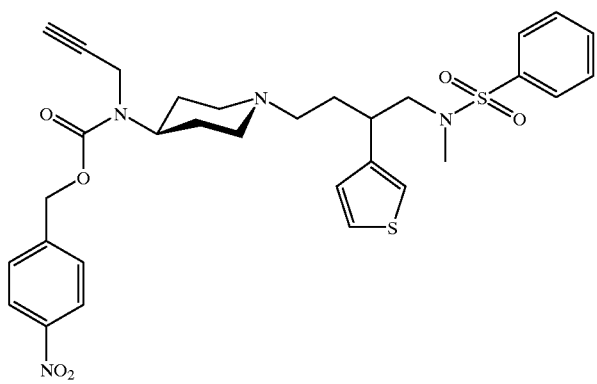
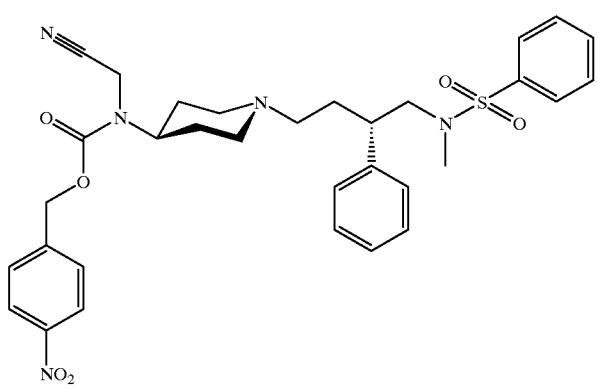
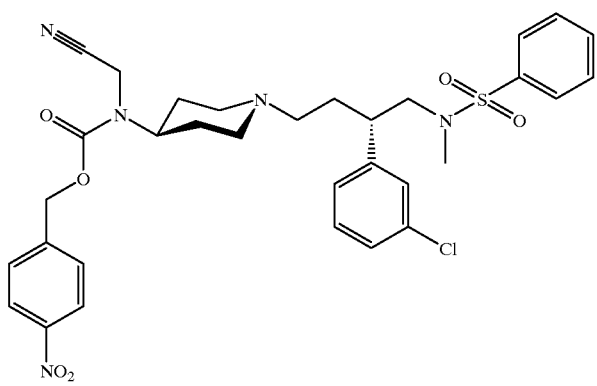
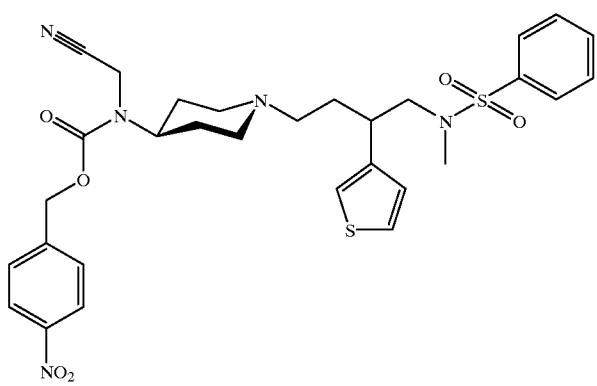

151
-continued
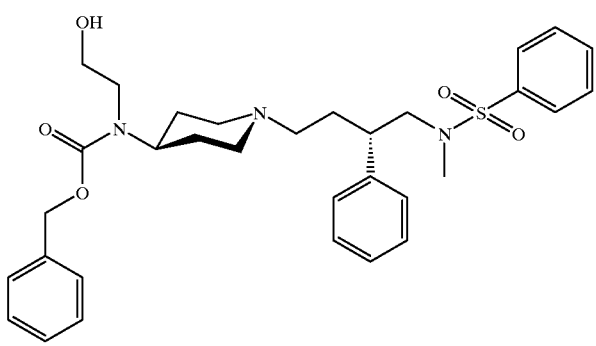
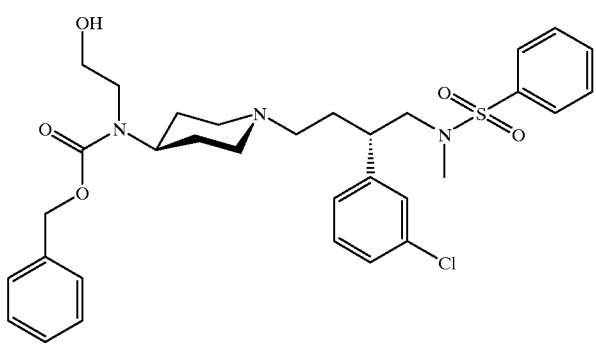
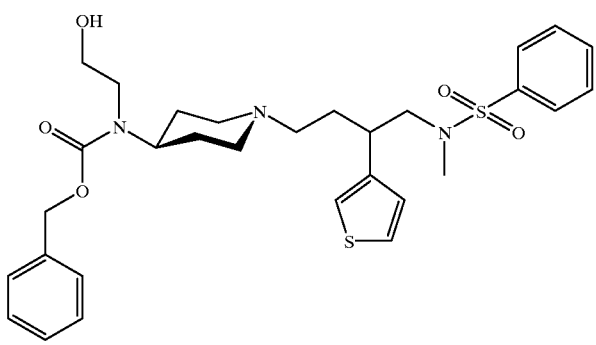
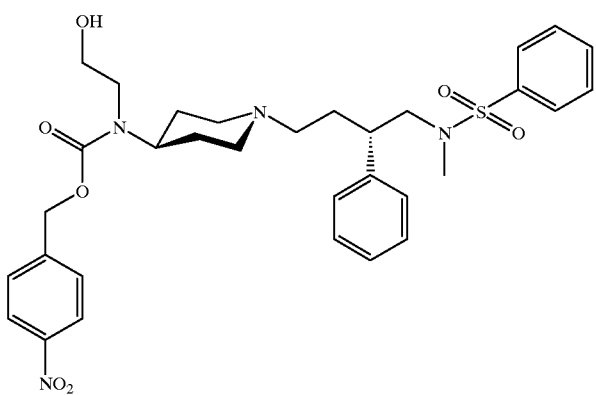
152

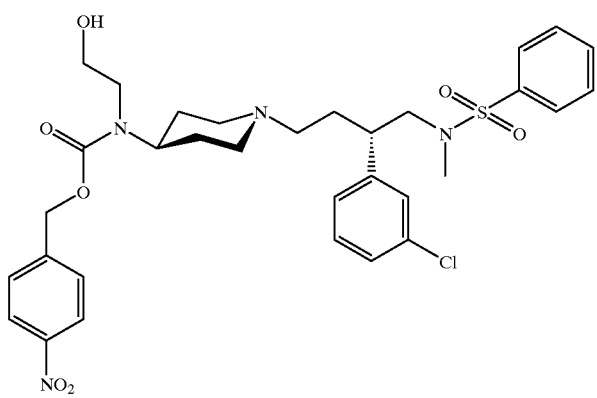
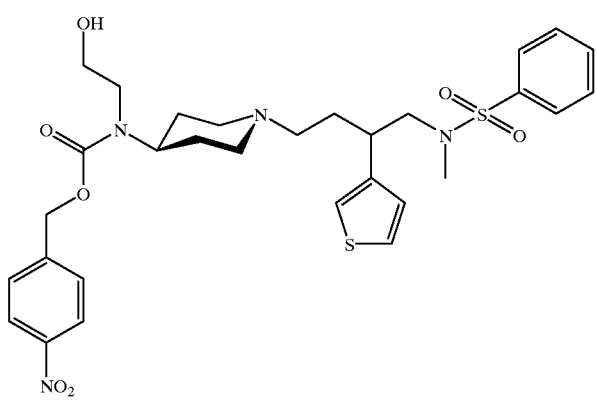
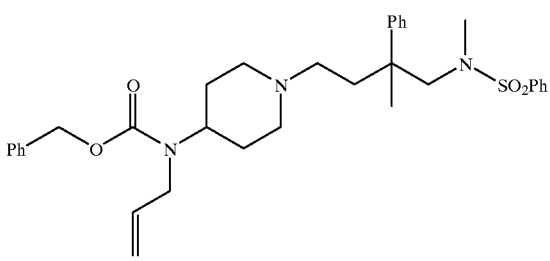
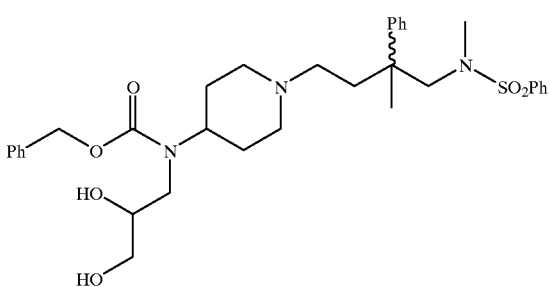
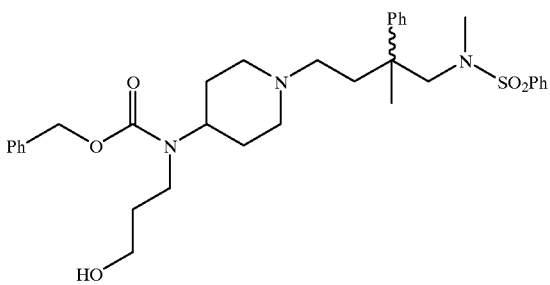

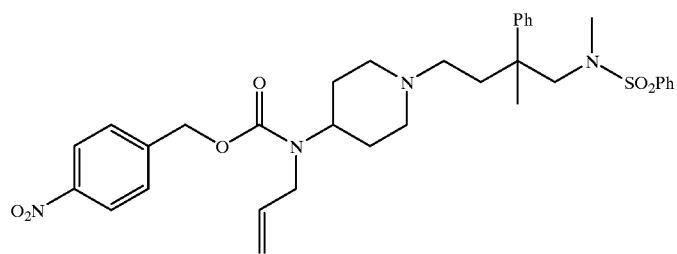
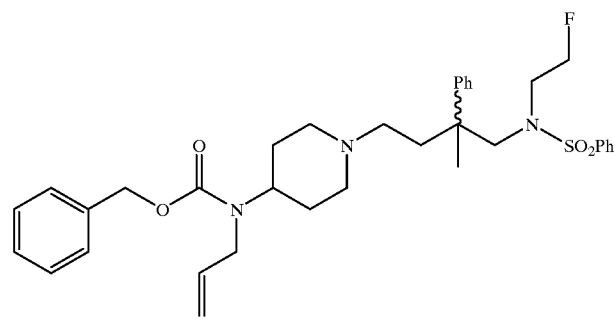
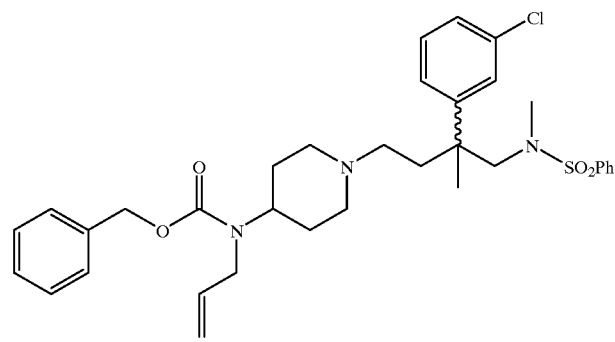
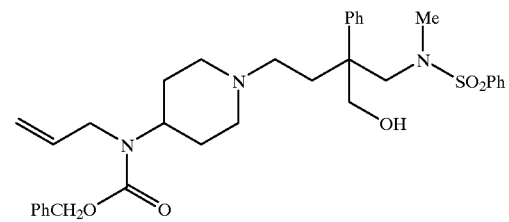
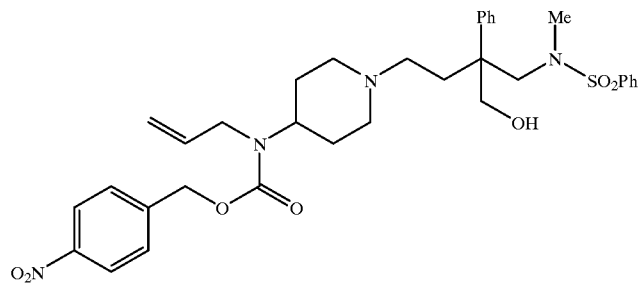

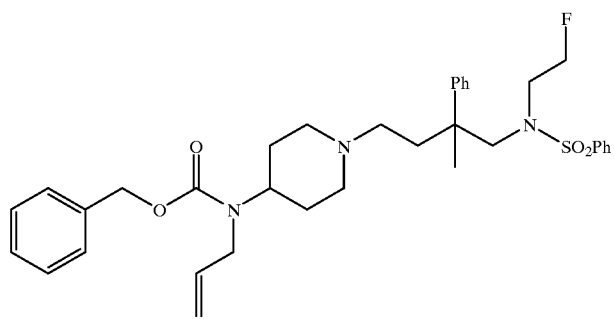
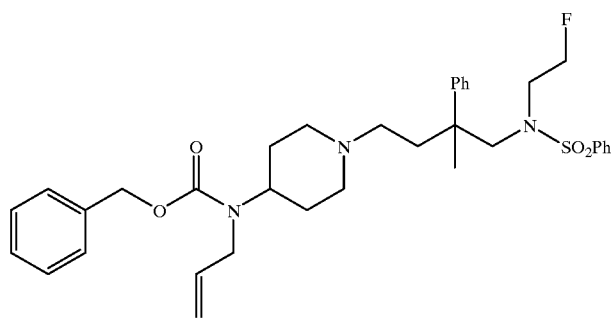
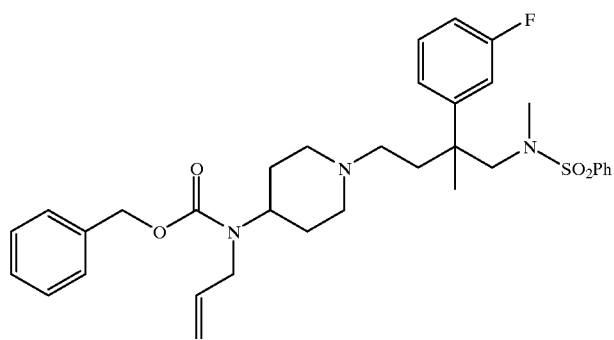
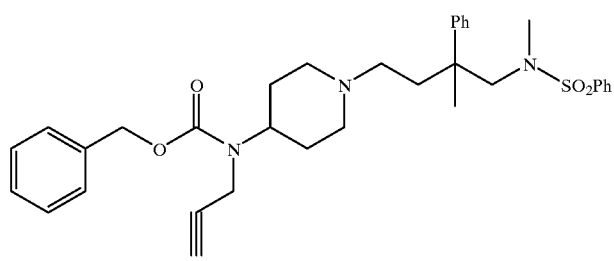
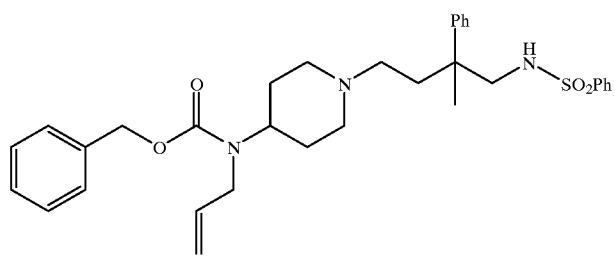

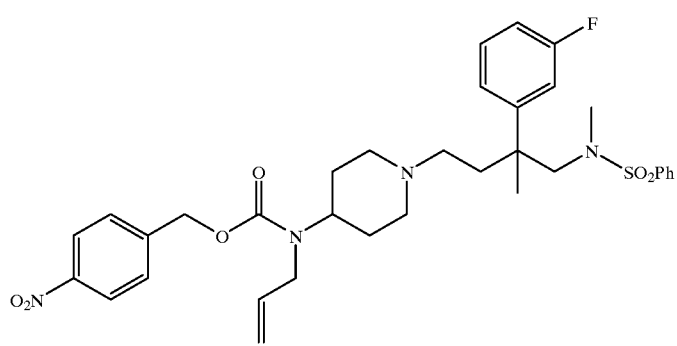
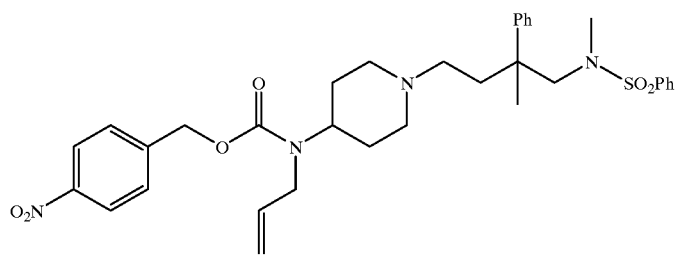
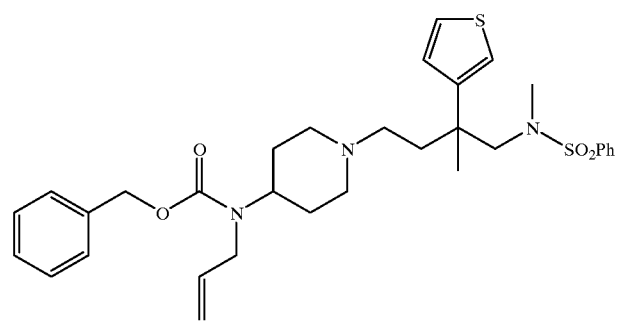
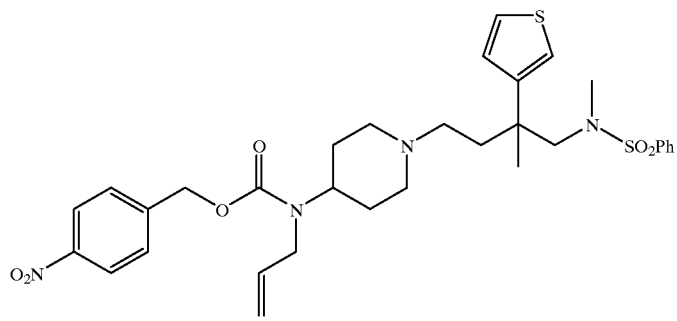
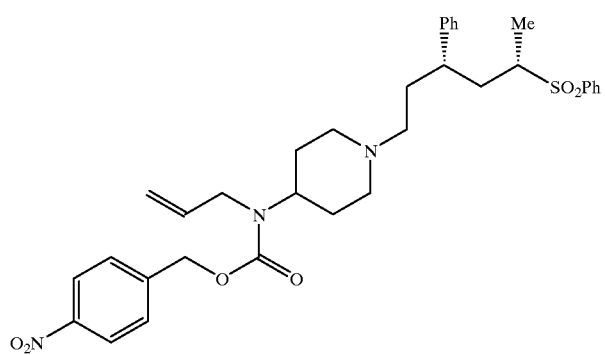

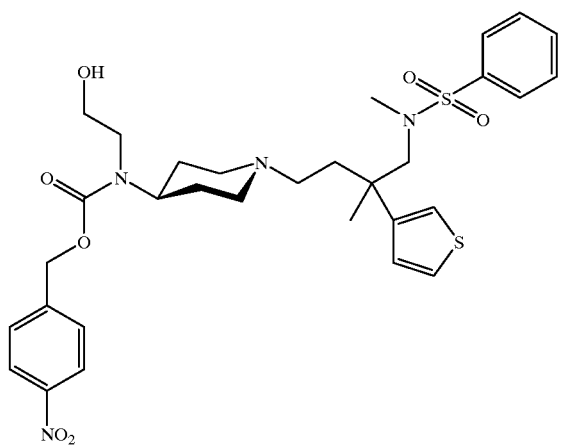
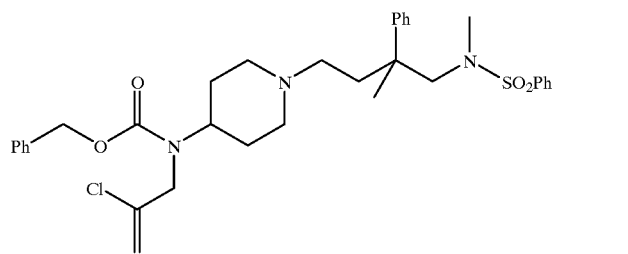
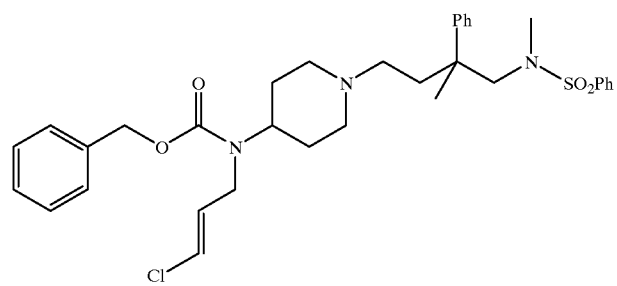
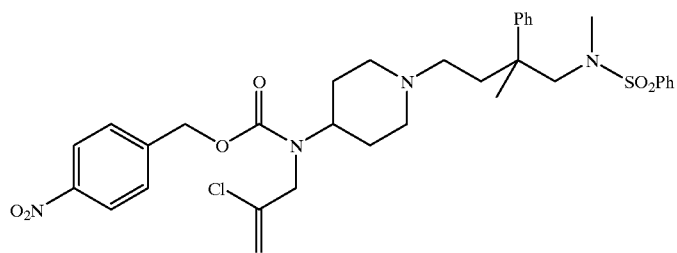
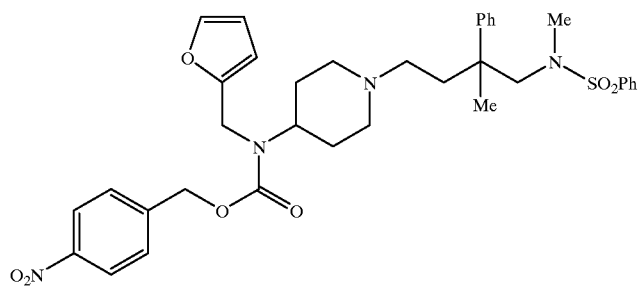

-continued
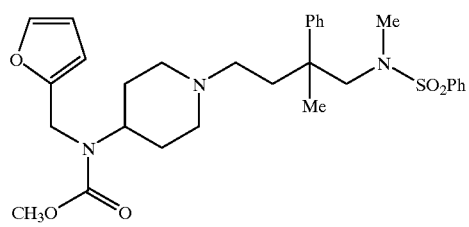
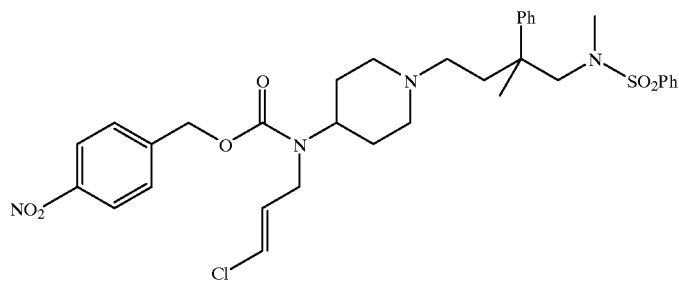
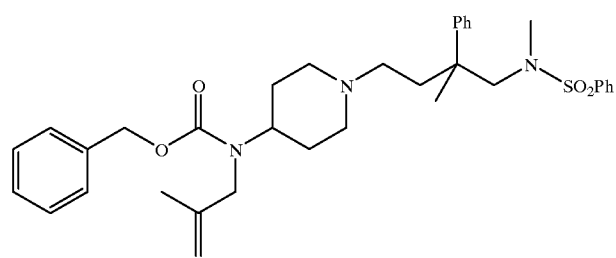
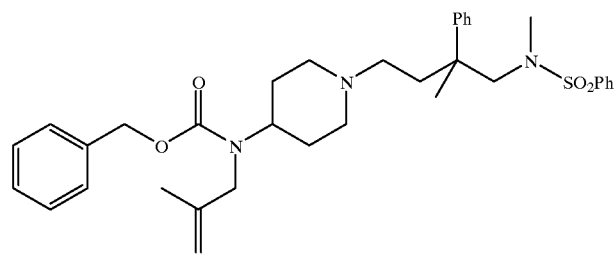
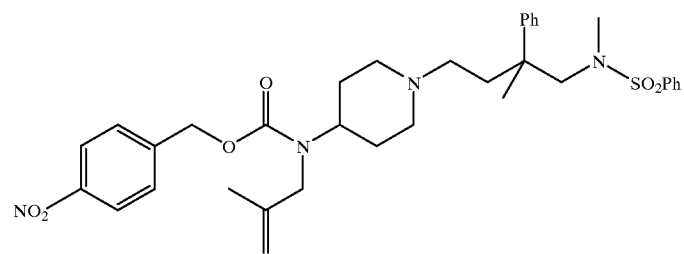
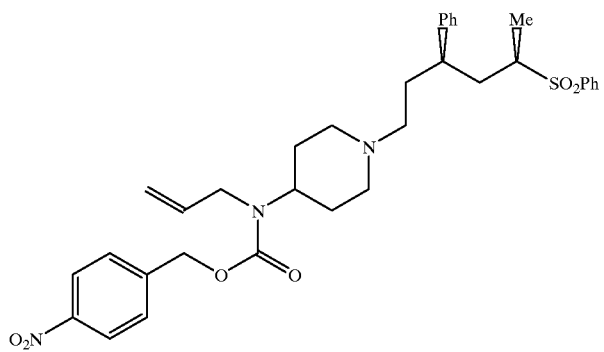

-continued

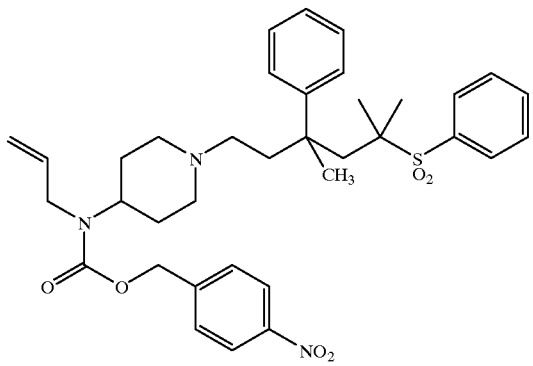

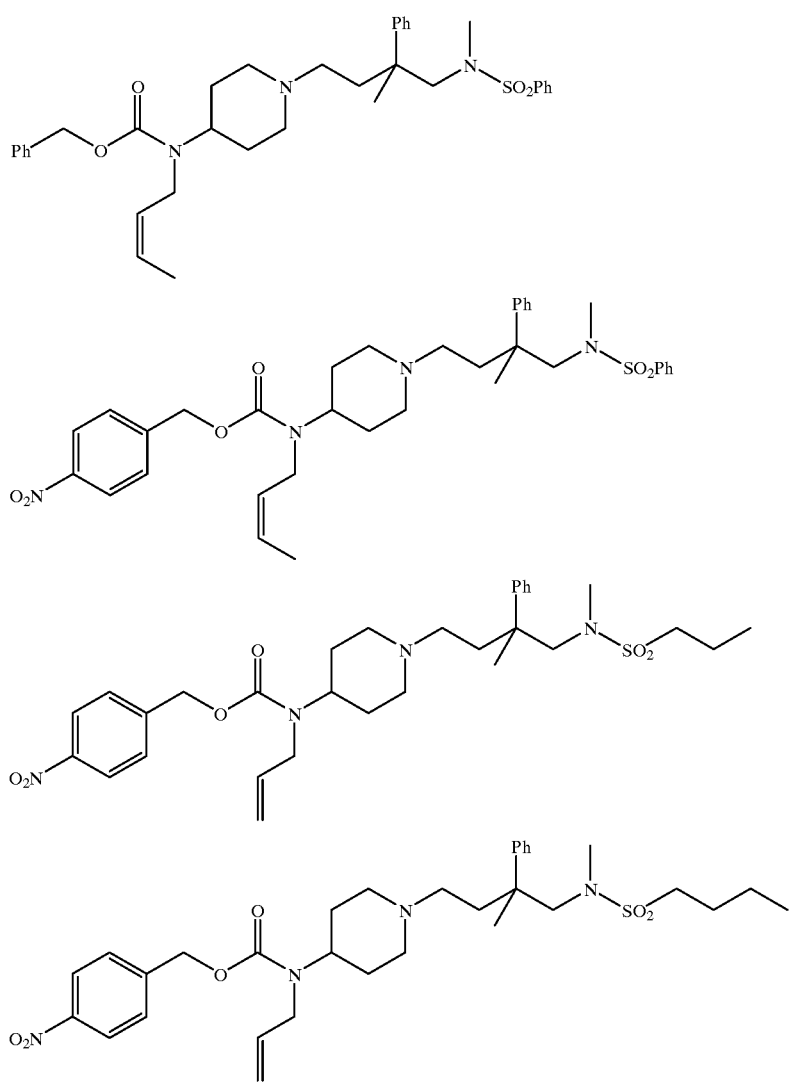

27. A pharmaceutical composition which comprises an inert carrier and a therapeutically effective amount of a compound of claim 1.

28. A method for blocking the entry of HIV into target cells of a patient comprising administering to the patient in need thereof the compound of claim 1 in an amount effective to block HIV from binding to surface receptors of the target cells.

29. The method of claim 28 wherein blocking the entry of HIV into target cells prevents infection of the patient by HIV.

30. The method of claim 28 wherein blocking the entry of HIV into target cells prevents infectious spread of HIV in the patient.

31. The method of claim 28 wherein blocking the entry of HIV into target cells delays the onset of AIDS in the patient.

32. The method of claim 28 wherein blocking the entry of HIV into target cells treats the pathological conditions of AIDS in the patient.

* * * * *